US008314221B2

(12) United States Patent
Faure

(10) Patent No.: US 8,314,221 B2
(45) Date of Patent: Nov. 20, 2012

(54) PHARMACODIAGNOSTIC TEST TARGETING ONCOLOGY AND NEURODEGENERATION

(76) Inventor: Laurence Claude Faure, Paris (FR)

( * ) Notice: Subject to any disclaimer, the term of this patent is extended or adjusted under 35 U.S.C. 154(b) by 151 days.

(21) Appl. No.: 12/282,117

(22) PCT Filed: Sep. 7, 2007

(86) PCT No.: PCT/FR2007/001449
§ 371 (c)(1),
(2), (4) Date: Sep. 8, 2008

(87) PCT Pub. No.: WO2008/029031
PCT Pub. Date: Mar. 13, 2008

(65) Prior Publication Data
US 2009/0311681 A1 Dec. 17, 2009

(30) Foreign Application Priority Data

Sep. 7, 2006 (FR) ..................................... 06 07859

(51) Int. Cl.
*C07H 21/02* (2006.01)
*A61K 31/00* (2006.01)
*C12Q 1/68* (2006.01)
(52) U.S. Cl. .......................... 536/23.1; 530/300; 435/6.1
(58) Field of Classification Search .................. None
See application file for complete search history.

(56) References Cited

U.S. PATENT DOCUMENTS 5,474,796 A * 12/1995 Brennan ....................... 427/2.13

OTHER PUBLICATIONS

Arya R, Kedar V, Hwang J R, McDonough H, Li H H, Taylor J, Patterson C. Muscle ring finger protein-1 inhibits PKC{epsilon} activation and prevents cardiomyocyte hypertrophy. J. Cell Biol. Dec. 20, 2004 ; 167 (6):1147-59. Epub Dec. 13, 2004.
Caroll J S, Prall O W J, Musgrove B A, Sutherland R L. A pure Estrogen Antagonist Inhibits Cyclin E-Cdk2 Activity in MCF-7 Breast Cancer Cells and Induces Accumulation of p130-B2F4 Complexes Characteristic of Quiescence. (2000) J Biol. Chem, 275 (49):38221-38559.
Chau B N, Wang J Y. Coordinated regulation of life and death by RB. (2003) Nat Rev Cancer, 3 (2): 130-8.
Cheng T, Scadden D T. Cell cycle entry of hematopoietic stem and progenitor cells controlled by distinct cyclin-dependent kinase inhibitors. (2002) Int J Hematol, 75 (5):460-5.
Classon M, Harlow E. The retnoblastoma tumour suppressor in development and cancer. (2002) Nat Rev Cancer, 2 (12): 910-7.
Coqueret O. Linking cyclins to transcriptional control. (2002) Gene, 299 (1-2): 35-55.
Crisanti P, Raguenez G, Blancher C, Neron B, Mamoune A, Omri B. Cloning and characterization of a novel transcription factor involved in cellular proliferation arrest: PATF.

Durocher D, Taylor I A, Sarbassova D, Haire L F, Westcott S L, Jackson S P, Smerdon S J, Yaffe M B. The molecular basis of FHA domain: phosphopeptide binding specificity and implications for phospho-dependant signaling mechanisms. (2000) Mol Cell, 6 (5):1169-82.
Durocher D, Jackson S P. The FHA domain. (2002) FEBS Lett, 513 (1): 58-66.
Espanel X, Le Cam L, North S, Sardet C, Brun G, Gillet G. Regulation of E2F-1 gene expression in avian cells. (1998) Oncogene, 17 (5): 585-94.
Regazzi R, Fabbro D, Costa S D, Bomer C, Eppenberger U. Effects of tumor promoters on growth and on cellular redistribution of phospholipid/Ca.sup.2+-dependant protein kinase in human breast cancer cells. (1986) Int J Cancer, 37 (5): 731-737.
Han E K, Begenann M, Sganibato A, Soh T W, Doki Y, Xing W Q, Liu W, Weinstein I B. Increased expression of cyclin D1 in a murine mammary epithelial cell line induces p27kip1, inhibits growth, and enhances apoptosis. Cell Growth Differ. Jun. 1996; 7(6):699-710.
He L Z, Merghoub T, Pandolfi P P. In vivo analysis of the molecular pathogenesis of acute promyelocytic leukemia in the mouse and its therapeutic implications. (1999) Oncogene, 18: 5278-5292.
Helin K. Regulation of cell proliferation by the E2F transcription factors. (1998) Curr Opin Genet Dev, 8 (1): 28-35.
Kohler G, Milstein C. Continuous cultures of fused cells secreting antibody of predefined specificity. Nature. Aug. 7, 1975; 256(5517):495-7.
Mundle S D, Saberwal G. Evolving intricacies and implications of E2F1 regulation. (2003) FASEB J, 17 (6): 569-74.
Opalka B, Dickopp A, Kirch H C. Apoptotic genes in cancer therapy. (2002) Cells Tissues Organs, 172 (2): 126-32.
Schneider S M, Offterdinger M, Huber H, Grunt T W. Involvement of nuclear steroid/thyroid/retinoid receptors and of protein kinases in the regulation of growth and of c-erbB and retinoic acid receptor expression in MCF-7 breast cancer cells. (1999) Breast Cancer Res and Treat, 58: 171-181.
Senderowicz A M. Cyclin-dependent kinases as targets for cancer therapy. (2002) Cancer Chemother Biol Response Modif, 20: 169-96.
Stiegler P, Giordano A. The family of retinoblastoma proteins. (2001) Crit Rev Eukaryot Gene Expr, 11 (1-3): 59-76.
Stevaux O, Dyson N J. A revised picture of the E2F transcriptional network and RB function. (2002) Curr Opin Cell Biol, 14 (6): 684-91.
Toma O, Weber N C, Wolter J I, Obal D, Preckel B, Schlack W. Desflurane preconditioning induces time-dependent activation of protein kinase C epsilon and extracellular signal-regulated kinase 1 and 2 in the rat heart in vivo. Anesthesiology. Dec. 2004; 101(6):1372-80.

(Continued)

Primary Examiner — Christopher M. Babic
(74) Attorney, Agent, or Firm — Jack Schwartz & Associates, PLLC

(57) ABSTRACT

A first objective is to demonstrate a method for the detection and prognosis of cancer and of its metastatic potential. Preferably, the cancer is selected from breast cancer, bladder cancer, ovarian cancer, lung cancer, skin cancer, prostate cancer, colon cancer, liver cancer, a sarcoma and a leukaemia, without being limited thereto. One aspect consists of the use of the LIV21 complex as a prognostic indicator for cancer and in the therapeutic monitoring thereof. The LIV21 complex is defined in terms of the extract of proteins and peptides studied by Maldi and ESI MS/MS or Maldi Tof/Tof mass spectrometry. The extract was obtained by attachment of the LIV21 complex to one of these LIV21 polyclonal antibodies. The LIV21 complex is also defined in terms of its overall mass spectrometry profile and the number and the molecular weight of the bands of protein extracts obtained as a function of the temperature to which the sample is subjected and the migration conditions described. Another aspect is the use of biochips for the pharmacodiagnosis of oncological pathologies and of neurodegeneration.

9 Claims, 49 Drawing Sheets

OTHER PUBLICATIONS

Ward E S, Gussow D, Griffiths A D, Jones P T, Winter G. Binding activities of a repertoire of single immunoglobulin variable domains secreted from *Escherichia coli*. Nature. Oct. 12, 1989; 341(6242):5446.

Wu C L, Zukerberg L R, Ngwu C, Harlow E, Lees J A. In vivo association of E2F and DP family proteins. (1995) Mol Cell Biol, 15 (5) 2536-46.

Yaffe M B. Phosphotyrosine-binding domains in signal transduction. (2002) Nat Rev Mol Cell Biol, 3 (3): 177-86. [0317].

Yamasaki L. Growth regulation by the E2F and DP transcription factor families. (1998) Results Probl Cell Difer, 22: 199-227.

Zee-Yong Park and David H. Russell. Identification of Individual Proteins in Complex Protein Mixtures by High-Resolution, High-Mass-Accuracy MALDI TOF-Mass Spectrometry Analysis of In-Solution Thermal denaturation/ Enzymatic Digestion. (2001) Anal Chem, 73 (11): 2558-2564.

\* cited by examiner

Coloration to the Silver Salts of a 12% polyacrylamide
Gel studied by the laboratory mass spectrometer Rouen (L. Coquet – P. Cossete)

LIV21 Complex

Fig. 1B

Premier mRNA

Genbank

```
  1 gagtctgccc ttgcgagctc agagtgtgcc cgtgcgccgc cgccgtcgta cctgccgccg
 61 ccgccaccgc caccatgccc aacttcgccg gcacctggaa gatgcgcagc agcgagaatt
121 tcgacgagct gctgaaggca ctgggtgtga acgccatgct gaggaaagtg gccgtagcgg
181 ctgcgtccaa gccgcacgtg gagatccgcc aggacgggga tcagttctac atcaagacat
241 ccaccaccgt gcgcaccact gagatcaact tcaaggtcgg agaaggcttt gaggaggaga
301 ccgtggacgg acgcaagtgc aggagtttag ccacttggga gaatgagaac aagatccact
361 gcaccaaac tcttcttgaa ggggacggcc ccaaaaccta ctggacccgt gagctggcca
421 acgatgaact tatcctgacg tttggcgccg atgacgtggt ctgcaccaga atttatgtcc
481 gggaatgaag gcagctggct tgctcctact ttcaggaagg gatgcaggtc ccgaggaat
541 atgtcatagt tctgagctgc cagtggaccg ccctttttcc ctaccaatat taggtgatcc
601 cgttttcccc atgacaatgt tgtagtgtcc cccacccca cccctggc cttggtgcct
661 cttgtatccc tagtgctgca tagcccggca tttgcacggt ttcgaagtca ttaaactggt
721 tagacgtgtc tcaaa (SEQ ID NO:142)
```

// >P29373|RABP2_HUMAN Cellular retinoic acid-binding protein 2 - Homo sapiens (Human).
MPNFSGNWKI IRSENFEELLKVLGVNVMLRKIAVAAASKPAVEIKQEGDTFYIKTSTTVR
TTEINFKVGEEFEEQTVDGRPCKSLVKWESENKMVCEQKLLKGEGPKTSWTRELTNDGEL
ILTMTADDVVCTRVYVRE (SEQ ID NO:163)

The section of the sequence P29373 (RABP2_HUMAN) you have selected corresponds to:
HELIX    16    22

In one-letter code:
```
        1         11         21         31         41
51
   1 MPNFSGNWKI  IRSENFEELL  KVLGVNVMLR  KIAVAAASKP
AVEIKQEGDT  FYIKTSTTVR       60
  61 TTEINFKVGE  EFEEQTVDGR  PCKSLVKWES  ENKMVCEQKL
LKGEGPKTSW  TRELTNDGEL      120
 121 ILTMTADDVV  CTRVYVRE  (SEQ ID NO:163)
```

HELIX    27    37

In one-letter code:
```
        1         11         21         31         41
51
   1 MPNFSGNWKI  IRSENFEELL  KVLGVNVMLR  KIAVAAASKP
AVEIKQEGDT  FYIKTSTTVR       60
  61 TTEINFKVGE  EFEEQTVDGR  PCKSLVKWES  ENKMVCEQKL
LKGEGPKTSW  TRELTNDGEL      120
 121 ILTMTADDVV  CTRVYVRE  (SEQ ID NO:163)
```

```
  1 cctgacgacc cggcgacggc gacgtctctt ttgactaaaa gacagtgtcc agtgctccag
 61 cctaggagtc tacggggacc gcctcccgcg ccgccaccat gccaacttc tctggcaact
121 ggaaaatcat ccgatcggaa aacttcgagg aattgctcaa agtgctgggg gtgaatgtga
181 tgctgaggaa gattgctgtg gctgcagcgt ccaagccagc agtggagatc aaacaggagg
```

Fig. 1B (continued)

```
241 gagacacttt ctacatcaaa acctccacca ccgtgcgcac cacagagatt aacttcaagg
301 ttggggagga gtttgaggag cagactgtgg atgggaggcc ctgtaagagc ctggtgaaat
361 gggagagtga gaataaaatg gtctgtgagc agaagctcct gaagggagag ggccccaaga
421 cctcgtggac cagagaactg accaacgatg gggaactgat cctgaccatg acggcggatg
481 acgttgtgtg caccagggtc tacgtccgag agtgagtggc cacaggtaga accgcggccg
541 aagcccacca ctggccatgc tcaccgccct gcttcactgc ccctccgtc ccaccccctc
601 cttctaggat agcgctcccc ttaccccagt cacttctggg ggtcactggg atgcctcttg
661 cagggtcttg ctttctttga cctcttctct cctcccctac accaacaaag aggaatggct
721 gcaagagccc agatcaccca ttccgggttc actcccgcc tcccaagtc agcagtccta
781 gccccaaacc agcccagagc agggtctctc taaaggggac ttgagggcct gagcaggaaa
841 gactggccct ctagcttcta cctttgtcc ctgtagccta tacagtttag aatatttatt
901 tgttaatttt attaaaatgc ttta (SEQ ID NO:143)
```

CRABP4
Q96R05|RET7_HUMAN Retinoid-binding protein 7 - Homo sapiens (Human)
MPADLSGTWTLLSSDNFEGYMLALGIDFATRKIAKLLKPQKVIEQNGDSFTIHTNSSLRN
YFVKFKVGEEFDEDNRGLDNRKCKSLVIWDNDRLTCIQKGEKKNRGWTHWIEGDKLHLEM
FCEGQVCKQTFQRA (SEQ ID NO:164)

section of the sequence Q96R05 (RET7_HUMAN) you have selected corresponds to:
HELIX 17 24

In one-letter code:
```
        1         11         21         31         41
51
    1 MPADLSGTWT LLSSDNFEGY MLALGIDFAT RKIAKLLKPQ
KVIEQNGDSF TIHTNSSLRN       60
   61 YFVKFKVGEE FDEDNRGLDN RKCKSLVIWD NDRLTCIQKG
EKKNRGWTHW IEGDKLHLEM      120
  121 FCEGQVCKQT FQRA (SEQ ID NO:164)
```

HELIX 28 34

In one-letter code:
```
        1         11         21         31         41
51
    1 MPADLSGTWT LLSSDNFEGY MLALGIDFAT RKIAKLLKPQ
KVIEQNGDSF TIHTNSSLRN       60
   61 YFVKFKVGEE FDEDNRGLDN RKCKSLVIWD NDRLTCIQKG
EKKNRGWTHW IEGDKLHLEM      120
  121 FCEGQVCKQT FQRA (SEQ ID NO:164)
```

TURN 76 79

In one-letter code:
```
        1         11         21         31         41
51
    1 MPADLSGTWT LLSSDNFEGY MLALGIDFAT RKIAKLLKPQ
KVIEQNGDSF TIHTNSSLRN       60
   61 YFVKFKVGEE FDEDNRGLDN RKCKSLVIWD NDRLTCIQKG
EKKNRGWTHW IEGDKLHLEM      120 (SEQ ID NO:164)
```

FIGURE 3 A

| Band 1 | Band 2 | | | | | | | |
|---|---|---|---|---|---|---|---|---|
| m/z | m/z | SN | Res. | intens. | m/z | SN | Res. | intens. |
| 726.3739 | 525.380 | 75.6 | 1903 | 3408.00 | 1748.844 | 4.9 | 16483 | 221.00 |
| 768.5312 | 545.322 | 133.8 | 1436 | 6029.00 | 1763.031 | 5.0 | 12143 | 223.00 |
| 842.5103 | 550.930 | 142.9 | 1612 | 6438.00 | 1794.832 | 17.1 | 15898 | 446.26 |
| 870.5261 | 568.641 | 790.6 | 2123 | 35626.00 | 1836.904 | 3.6 | 15701 | 162.00 |
| 882.5552 | 580.777 | 26.4 | 2516 | 1190.00 | 1856.950 | 4.6 | 12370 | 214.00 |
| 949.5031 | 587.667 | 33.3 | 2795 | 1501.00 | 1873.917 | 15.9 | 17904 | 420.12 |
| 963.5154 | 631.470 | 60.4 | 6569 | 2991.00 | 1878.979 | 15.9 | 16250 | 407.25 |
| 1017.5794 | 659.447 | 30.9 | 6811 | 1394.00 | 1880.935 | 20.1 | 11590 | 516.13 |
| 1051.6872 | 662.431 | 67.2 | 9193 | 3027.00 | 1927.967 | 6.2 | 11723 | 281.00 |
| 1135.5636 | 667.159 | 41.0 | 10067 | 1840.00 | 1928.974 | 6.2 | 14954 | 152.02 |
| 1151.5455 | 711.153 | 34.5 | 10289 | 1553.00 | 1942.020 | 4.7 | 19798 | 211.00 |
| 1167.6043 | 713.175 | 42.7 | 11689 | 1922.00 | 1944.019 | 20.9 | 16714 | 478.21 |
| 1206.5889 | 739.151 | 20.4 | 12971 | 918.00 | 2021.003 | 137.1 | 14814 | 3509.82 |
| 1233.6074 | 757.168 | 13.8 | 13762 | 707.82 | 2037.013 | 8.2 | 10928 | 212.04 |
| 1240.6366 | 790.491 | 14.4 | 12895 | 649.00 | 2045.020 | 7.3 | 15747 | 330.00 |
| 1251.7080 | 842.510 | 19.8 | 11687 | 767.71 | 2059.030 | 4.2 | 14227 | 191.00 |
| 1267.6791 | 870.537 | 8.6 | 11748 | 397.00 | 2125.002 | 5.9 | 14783 | 264.00 |
| 1295.6359 | 881.299 | 23.3 | 13598 | 829.82 | 2211.105 | 151.9 | 13211 | 3373.88 |
| 1324.6345 | 921.541 | 17.0 | 12241 | 600.49 | 2225.106 | 17.2 | 14637 | 773.00 |
| 1336.6586 | 1330.770 | 6.3 | 15012 | 284.00 | 2283.181 | 48.1 | 12236 | 2167.00 |
| 1354.6603 | 1341.706 | 3.3 | 7921 | 149.00 | 2311.205 | 10.0 | 15157 | 207.42 |
| 1369.6215 | 1373.739 | 21.3 | 15547 | 533.87 | 2383.261 | 73.2 | 10466 | 1204.30 |
| 1399.6775 | 1439.840 | 20.1 | 14012 | 522.60 | 2461.196 | 11.1 | 11453 | 196.62 |
| 1410.7223 | 1451.764 | 15.2 | 13759 | 401.95 | 2477.117 | 1.9 | 15432 | 85.00 |
| 1442.6973 | 1467.871 | 4.6 | 16096 | 201.00 | 2511.375 | 9.1 | 9656 | 154.80 |
| 1507.7352 | 1479.823 | 10.1 | 13230 | 266.59 | 2539.329 | 11.0 | 9640 | 180.05 |
| 1586.7312 | 1486.853 | 7.0 | 21505 | 316.00 | 2549.262 | 3.4 | 13928 | 155.00 |
| 1599.8580 | 1534.956 | 17.1 | 14704 | 481.02 | 2587.249 | 3.4 | 11702 | 153.00 |
| 1604.7104 | 1537.826 | 23.5 | 14898 | 675.26 | 2591.295 | 25.7 | 10330 | 388.23 |
| 1687.8247 | 1567.779 | 37.8 | 15022 | 1065.43 | 2650.220 | 8.7 | 10510 | 132.78 |
| 1728.8549 | 1570.816 | 14.6 | 16144 | 408.22 | 2750.500 | 42.2 | 10212 | 933.12 |
| 1746.8813 | 1593.926 | 155.8 | 15098 | 4349.61 | 2766.494 | 9.3 | 8850 | 133.86 |
| 1794.7933 | 1607.944 | 3.5 | 10703 | 157.00 | 2780.508 | 8.7 | 10597 | 391.00 |
| 1800.9407 | 1639.938 | 9.4 | 11769 | 238.84 | 2823.368 | 40.4 | 9128 | 513.24 |
| 1830.9074 | 1684.943 | 21.2 | 6015 | 538.84 | 2837.393 | 13.1 | 6755 | 161.25 |
| 1871.9277 | 1694.843 | 15.6 | 8084 | 407.76 | 3265.843 | 9.2 | 6905 | 58.69 |
| 1937.0540 | 1698.906 | 16.6 | 15134 | 431.33 | 3324.905 | 1.5 | 31230 | 68.00 |
| 1951.0366 | 1721.877 | 4.6 | 17947 | 207.00 | 3338.673 | 2.1 | 6212 | 34.00 |
| 1986.9046 | | | | | | | | |
| 2074.1188 | | | | | | | | |
| 2087.0345 | | | | | | | | |
| 2197.0986 | | | | | | | | |
| 2691.2664 | | | | | | | | |
| 2748.3890 | | | | | | | | |

Figure 5B

| M/Z | SN | RES | INTENS | M/Z | SN | RES | INTENS |
|---|---|---|---|---|---|---|---|
| 523.417 | 11.5 | 1792 | 1772.66 | 875.442 | 10.3 | 6713 | 990.39 |
| 525.367 | 46.8 | 1713 | 7221.40 | 877.033 | 16.7 | 9152 | 1576.0 |
| 527.381 | 17.7 | 1720 | 2557.56 | 881.272 | 61.4 | 8131 | 5819.23 |
| 532.508 | 14.5 | 1373 | 2486.82 | 895.484 | 8.5 | 6941 | 782.09 |
| 535.446 | 14.0 | 1284 | 2445.1167 | 912.467 | 9.0 | 8350 | 760.90 |
| 545.284 | 13.9 | 804 | 2363.94 | 932.507 | 10.8 | 9834 | 864.89 |
| 550.956 | 93.9 | 1288 | 15729.62 | 964.509 | 12.4 | 8936 | 920.20 |
| 552.879 | 11.9 | 1067 | 1979.13 | 1000.523 | 27.5 | 9695 | 1949.46 |
| 559.967 | 5.4 | 1466 | 1366.91 | 1017.604 | 115.1 | 9241 | 8032.50 |
| 568.652 | 361.6 | 1693 | 57586.04 | 1045.586 | 9.9 | 9169 | 688.13 |
| 570.621 | 19.8 | 1996 | 3145.51 | 1050.479 | 13.6 | 6545 | 961.75 |
| 587.589 | 9.2 | 1486 | 1383.14 | 1094.596 | 24.9 | 8900 | 1745.22 |
| 631.482 | 12.4 | 5994 | 1980.11 | 1125.510 | 16.2 | 10233 | 1140.90 |
| 634.077 | 18.9 | 5902 | 3017.82 | 1135.590 | 40.3 | 9680 | 2795.06 |
| 644.030 | 8.8 | 5879 | 1413.40 | 1151.587 | 80.5 | 2953 | 5525.67 |
| 650.033 | 47.7 | 5911 | 7617.98 | 1164.610 | 9.9 | 8657 | 877.93 |
| 656.047 | 11.2 | 6669 | 1752.59 | 1167.640 | 22.8 | 9201 | 1533.21 |
| 659.375 | 12.0 | 4291 | 1845.17 | 1182.651 | 35.4 | 9666 | 2352.98 |
| 665.991 | 20.3 | 7264 | 3113.81 | 1190.88 | 12.8 | 10427 | 1980.89 |
| 667.176 | 10.6 | 10192 | 1613.93 | 1202.647 | 10.1 | 10452 | 675.87 |
| 669.183 | 9.7 | 8995 | 1446.37 | 1206.611 | 14.3 | 5304 | 941.84 |
| 679.491 | 11.0 | 7026 | 1627.96 | 1278.828 | 11.0 | 9536 | 865.13 |
| 711.164 | 13.0 | 8259 | 1689.34 | 1281.682 | 8.3 | 5015 | 462.52 |
| 713.176 | 12.8 | 11331 | 1842.36 | 1289.738 | 10.0 | 11720 | 595.53 |
| 736.401 | 11.0 | 7778 | 1277.67 | 1295.58 | 12.1 | 7068 | 711.73 |
| 811.413 | 12.3 | 8916 | 1250.66 | 1358.782 | 17.7 | 674 | 1257.86 |
| 825.087 | 31.1 | 7897 | 3184.28 | 13 | 9.8 | 99 | 690.08 |
| 828.403 | 36.0 | 7821 | 3747.15 | 1369.561 | 12.4 | 10 | .33 |
| 839.069 | 11.0 | 9636 | 1145.86 | 1399.715 | 167.7 | | |
| 841.064 | 21.4 | 7446 | 2196.74 | 1410.772 | 125.6 | 3515 | 9097.13 |
| 842.510 | 33.0 | 8979 | 3374.68 | 1417.825 | 16.3 | 12075 | 1178.20 |
| 845.080 | 16.0 | 7986 | 1663.96 | 1442.731 | 64.1 | 10024 | 4628.84 |
| 855.046 | 11.4 | 9693 | 1130.01 | 1454.764 | 55.3 | 10005 | 3966.53 |
| 861.061 | 32.7 | 8216 | 3209.79 | 1462.310 | 33.4 | 8702 | 2405.91 |
| 870.547 | 17.1 | 8177 | 1653.62 | 1507.771 | 65.3 | 11136 | 4314.69 |

Figure 5B (continued)

| M/Z | SN | RES | INTENS |
|---|---|---|---|
| 1565.739 | 16.7 | 7567 | 982.33 |
| 1586.765 | 99.2 | 9256 | 6374.99 |
| 1599.902 | 71.2 | 8838 | 733.71 |
| 1604.731 | 147.1 | 9003 | 9804.34 |
| 1606.807 | 25.9 | 7174 | 1713.25 |
| 1669.851 | 7.1 | 7141 | 460.33 |
| 1674.825 | 20.2 | 9827 | 1320.49 |
| 1718.892 | 9.1 | 10573 | 529.69 |
| 1745.265 | 9.8 | 8553 | 539.79 |
| 1759.872 | 10.4 | 8768 | 592.43 |
| 1830.503 | 30.7 | 10237 | 1904.72 |
| 1871.892 | 9.5 | 10343 | 608.44 |
| 1885.918 | 43.5 | 9389 | 2798.03 |
| 1904.844 | 11.1 | 5316 | 720.49 |
| 1936.989 | 36.8 | 9061 | 2317.09 |
| 1951.031 | 3.2 | 7229 | 533.22 |
| 1964.041 | 6.3 | 9803 | 446.31 |
| 1961.263 | 16.1 | 9116 | 532.10 |
| 2038.014 | 64.1 | 8217 | 4151.58 |
| 2071.074 | 12.3 | 7435 | 774.14 |
| 2072.057 | 22.2 | 8049 | 1396.12 |
| 2074.145 | 84.1 | 8029 | 5294.84 |
| 2128.143 | 12.5 | 7165 | 741.03 |
| 2145.088 | 34.5 | 9080 | 2031.68 |
| 2160.936 | 23.1 | 8811 | 1340.50 |
| 2166.016 | 23.7 | 7865 | 1379.11 |
| 2195.027 | 14.1 | 6723 | 808.56 |
| 2211.108 | 128.3 | 7605 | 7445.24 |
| 2225.130 | 16.7 | 8302 | 581.63 |
| 2240.140 | 6.8 | 8575 | 563.54 |
| 2283.176 | 83.4 | 7474 | 4628.04 |
| 2365.235 | 13.7 | 7700 | 529.35 |
| 2401.113 | 8.9 | 7582 | 361.41 |
| 2409.062 | 11.6 | 5419 | 463.14 |
| 2415.117 | 7.5 | 6932 | 295.18 |
| 2429.085 | 38.2 | 6571 | 1462.15 |
| 2431.163 | 31.2 | 5647 | 1192.72 |
| 2585.187 | 13.0 | 8390 | 434.75 |
| 2614.281 | 11.5 | 6400 | 375.80 |
| 2631.339 | 13.2 | 7813 | 423.96 |
| 2716.254 | 10.4 | 5569 | 306.07 |
| 2787.404 | 66.3 | 6250 | 1774.37 |
| 2879.445 | 11.0 | 5408 | 273.63 |
| 3017.371 | 10.7 | 4809 | 229.47 |
| 3053.472 | 119.1 | 5804 | 2541.30 |

| M/Z | SN | RES | INTENS |
|---|---|---|---|
| 3067.576 | 17.7 | 5563 | 373.53 |
| 3343.716 | 29.2 | 5245 | 476.24 |
| 3415.763 | 2.3 | 2219 | 366.00 |

Figure 6

Taxonomy       : Eukaryota (eucaryotes) (150050 sequences)
Timestamp      : 4 Mar 2006 at 20:47:45 GMT
Top Score      : 81 for P15516-00-01-00, (HIS3_HUMAN) Splice isoform Displayed;

Probability Based Mowse Score

Protein score is -10*Log(P), where P is the probability that the observed match is a random event.
Protein scores greater than 64 are significant (p<0.05).

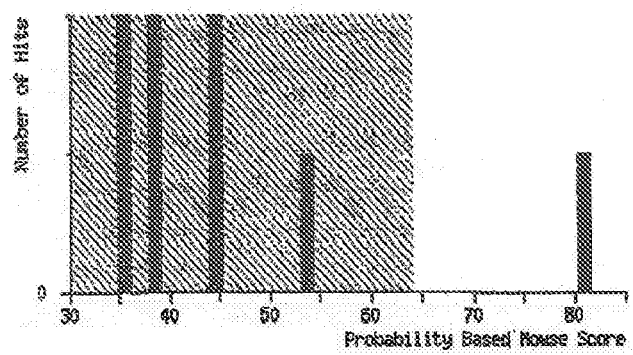

1.   P15516-00-01-00   Mass: 5449    Score: 81   Expect: 0.0012  Queries matc
     (HIS3_HUMAN) Splice isoform Displayed; Variant histatin-3-2; Conflict Displ
     P15516-00-00-00   Mass: 6145    Score: 80   Expect: 0.0017  Queries matc
     (HIS3_HUMAN) Splice isoform Displayed; Variant Displayed; Conflict Displaye Match to: P15516-00-01-00 Score: 81 Expect: 0.0012
(HIS3_HUMAN) Splice isoform Displayed; Variant histatin-3-2; Conflict Displayed;

Nominal mass (M_r): 5449; Calculated pI value: 10.38
NCBI BLAST search of P15516-00-01-00 against nr
Unformatted sequence string for pasting into other applications Taxonomy: Homo sapiens Cleavage by Trypsin: cuts C-term side of KR unless next residue is P
Sequence Coverage: 52%

Matched peptides shown in Bold Red

1 MKFFVTALIL AIMLSMTGAD SHAKRHHGYK RKFHEKHHSH QGYRSN    SEQ N°189

Show predicted peptides also

Sort Peptides By    ⦿ Residue Number  ○ Increasing Mass  ○ Decreasing Mass    SEQ N° 190

| Start - End | Observed | Mr(expt) | Mr(calc) | Delta | Miss | Sequence | SEQ N° 191 |
|---|---|---|---|---|---|---|---|
| 2 - 24 | 2511.3740 | 2510.3667 | 2510.3428 | 0.0239 | 1 | M.KFFVFALILAIML | |
| 3 - 24 | 2383.2600 | 2382.2527 | 2382.2479 | 0.0048 | 0 | K.FFVFALILAMLS | |
| 3 - 25 | 2539.3280 | 2538.3207 | 2538.3490 | -0.0283 | 1 | K.FFVFALILAMLS | |

Figure 7

```
User            : laur
Email           : laurence.faure4@wanadoo.fr
Search title    :
Database        : SwissProt 49.1 (269880 sequences; 124153953 residues)
Timestamp       : 4 Mar 2006 at 20:43:12 GMT
Top Score       : 72 for P15516-00-01-00, (HIS3_HUMAN) Splice isoform Displayed;
```

Probability Based Mowse Score

Protein score is $-10*Log(P)$, where P is the probability that the observed match is a random event. Protein scores greater than 67 are significant ($p<0.05$).

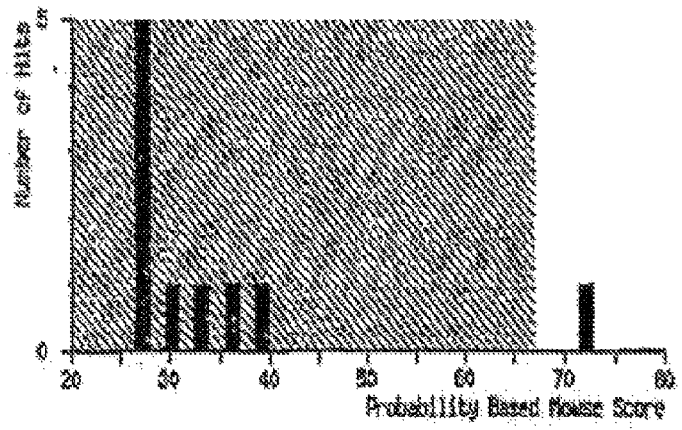

Search Parameters

```
Type of search        : Sequence Query
Enzyme                : Trypsin
Variable modifications: Carboxymethyl (C),Oxidation (M)
Mass values           : Monoisotopic
Protein Mass          : Unrestricted
Peptide Mass Tolerance: ± 20 ppm
Fragment Mass Tolerance: ± 0.8 Da
Max Missed Cleavages  : 1
Instrument type       : Default
Query1 (2021.0030,1+) : <no title>
Query2 (2037.0134,1+) : <no title>
Query3 (2125.0010,1+) : <no title>
Query4 (2383.2608,1+) : <no title>
Query5 (2511.3749,1+) : <no title>
Query6 (2539.3286,1+) : <no title>
```

Figure 9A
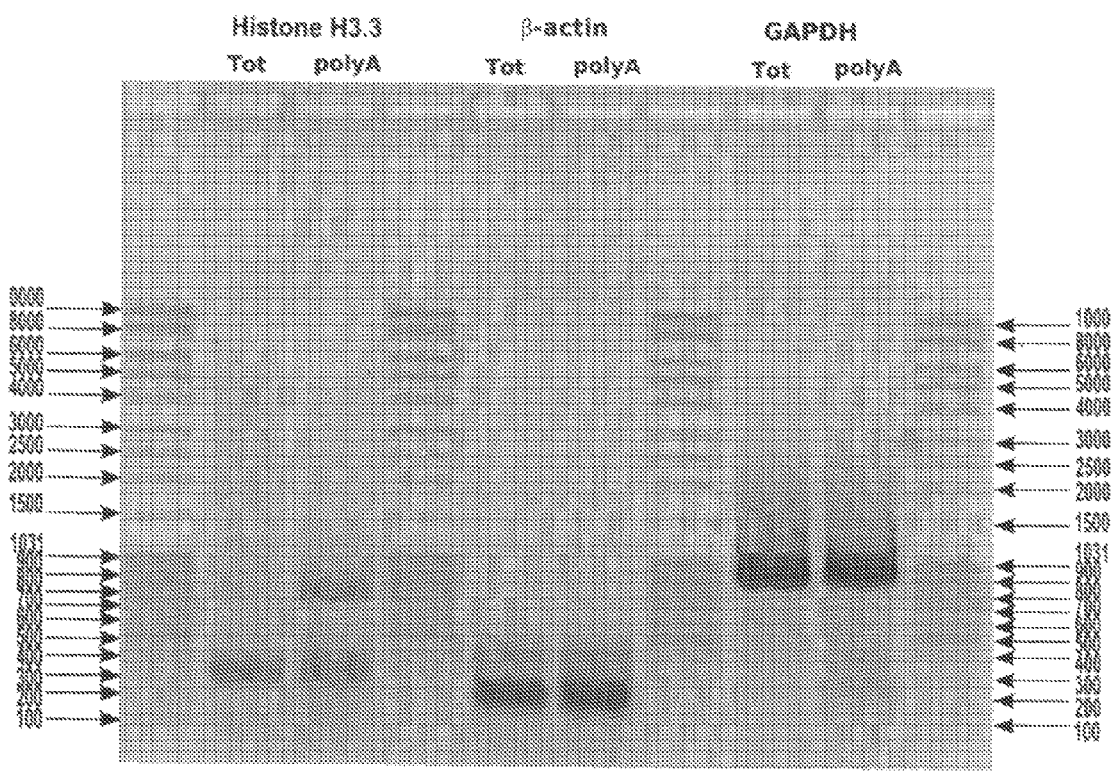
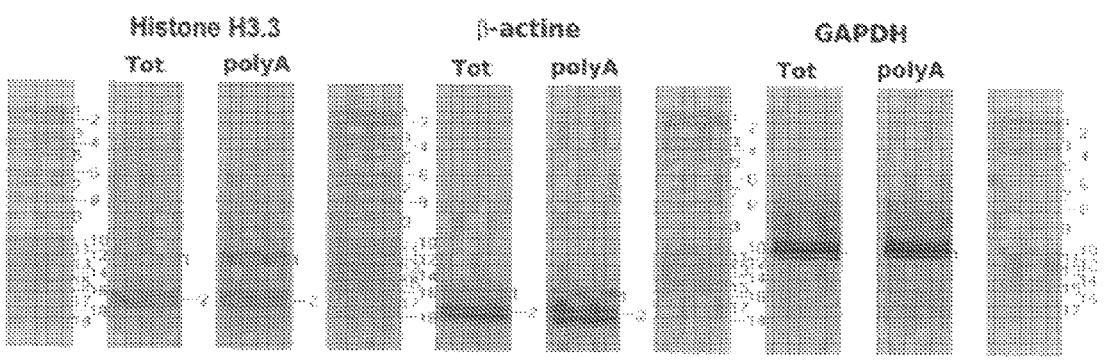

Track 2: Ligation G45T

Track 4: Ligation S45T

Track 6: Ligation G55T

Track 7: Ligation S55M

Track 8: Ligation S55T

Analysis of Molecular Mass

Screening of clones by Eco RI shows that on the nine clones S45T, three have inserts of 100 pb, 216 pb and 410 pb.

On the clones G45T, on the six clones tested, three have inserts of 57, 71 and 148 pb.

Figure 17

PGEMT Easy cloning of fragments were PCR S55T (ATG splice on RT 55°C in total RNAs and fragments S55 M (ATG splice RT on RT 55°C mRNA)
Screening minipreps by EcoR1

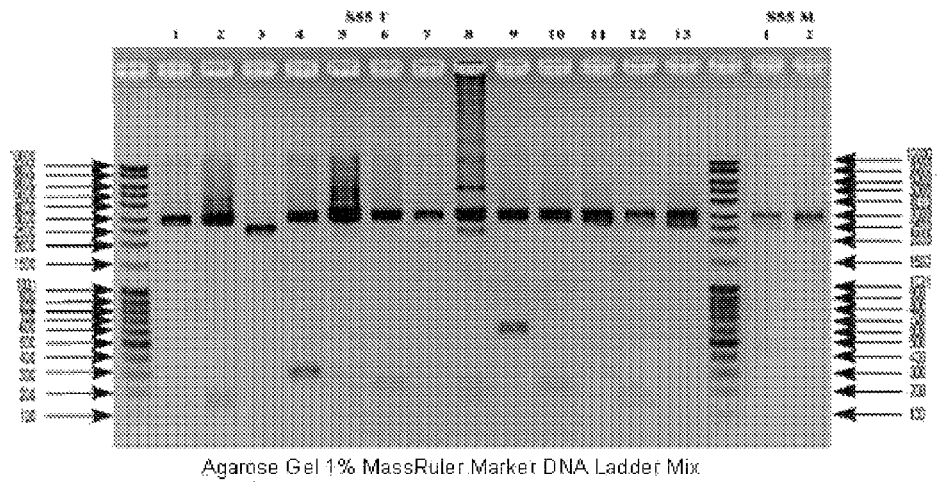

Agarose Gel 1% MassRuler Marker DNA Ladder Mix

Analysis of molecular masses:

PGEMT Easy cloning of fragments were PCR S55T (ATG splice on RT 55°C in total RNAs and fragments S55 M (ATG splice RT on RT 55°C mRNA)
Screening minipreps by EcoR1

The clones of G45T5(148bp), S45T9(410bp), S45T3(100bp), S55M1(491bp) S55T6 (251bp) & S55T9(637bp)

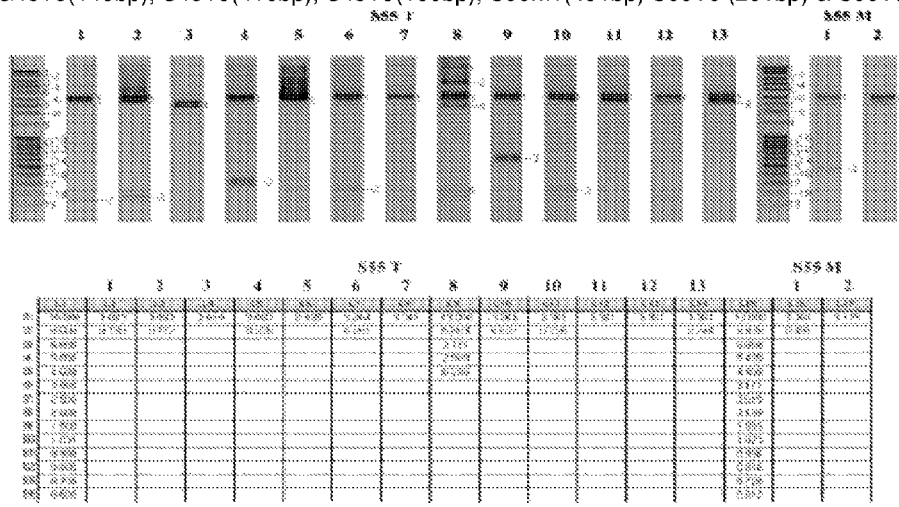

Figure 18A

```
              20         30         40         50         60         70
s45T9  GNNCBNGCCGCCBGGCGGCCGCGGGAATTCGATTAAATATAAGCAATCCCAACACTTTG
       ::  :  :::::   ::::::::::: ::::::::::::::::::::::::::::::::
s55M1  GNTCCGGCCGCCATGGCGGCCGCGGG-ATTCGATTAAATATAAGCAATCCCAACACTTTG
            10         20         30         40         50         60

80         90        100        110        120        130
s45T9  CNNNGCCGAGGCTGGCGGATCACGAGGTCAGGAGATGGAGACCATCCTGGCTAACACAGT
       :   ::: ::::: :::: :::::::::::::::::::::::::::::::::::::::::
s55M1  CGAGGCCGAGGCCGGGCGGATCACGAGGTCAGGAGATGGAGACCATCCTGGCTAACACAGT
            70         80         90        100        110        120

140        150        160        170        180        190
s45T9  GAAACCCTGTCTCTACTGAAAATACAAAAAATTAGCCGGGCGTGGCGGCAGTGGCTGTA
       :::::::: :::::: ::::::::::::::: ::::::::: ::::::::: ::::::
s55M1  GAAACCCTGTCTCTACCGGAAAATACAAAAAAGTAGCCGGGCGTGGCGGCAGGCGCCTGTA
            130        140        150        160        170        180

200        210        220        230        240        250
s45T9  GCCCCAGCTACTCAGGAGGCTGAGGCAGGAGAATGGCATGAACCCAGGAGGCAGAGCTTG
       :  ::: :::::::::::::::::::::::::::::::::::::::::::: ::::::::
s55M1  GTCCCAGCTACTCAGGAGGCTGAGGCAGGAGAATGGCATGAACCCAGGAGGCAGAGCTTG
            190        200        210        220        230        240

260        270        280        290        300        310
s45T9  CAGTGAGCCGAGATTGTGCCACTGCACTCCAGCCTGGGCAACAGAGCGAGACTCCATCTC
       :::::::::::::::::::::::::::::::::::::::::::::::::::::::::::
s55M1  CAGTGAGCCGAGATTGTGCCACTGCACTCCAGCCTGGGCAACAGAGCGAGACTCCATCTC
            250        260        270        280        290        300

320        330        340        350        360        370
s45T9  AAAAAAAAAAAAAAAATCACCCCAAAGCAATAAGGAGAACTAGAACAGGACATACACTCC
        :::::::::::::::::::::::::::::::::::::::::::::::::::::::::::
s55M1  -AAAAAAAAAAAAAAATCACCCCAAAGCAATAAGGAGAACTAGAACAGGACATACACTCC
            310        320        330        340        350        360

380        390        400        410        420        430
s45T9  AACACTGGTGAAACTAGGAAAACATATGTAACCCCAAACCACAATATATACACACAAAAC
       ::::::::::::::::::::::::::::::::::::::::::::::::::::::::::::
s55M1  AACACTGGTGAAACTAGGAAAACATATGTAACCCCAAACCACAATATATACACACAAAAC
            370        380        390        400        410        420

440        450        460        470        480
s45T9  TATACGAGATGTTGGGATTGC------TTAAT  (SEQ ID NO:171)
       ::::::::                  :::::
s55M1  TATACGAGA░░░░░░░░░░░░░░░░░AAT   (SEQ ID NO:172)
``` s55T9 M13 REVERSE 700 pb

Comparison of:

(A) ./wwwtmp/lalign/.26200.1.seq s45T9
(B) ./wwwtmp/lalign/.26200.2.seq s55T9
using matrix file: DNA, gap penalties: -14/-4

70.9% identity in 891 nt overlap; score: 1973 E(10,000): 4.9e-156

```
              30         40         50         60         70         80
s45T9  CCNNGCCGGCCGCGGGAATTCGATTAAATATAAGCAATCCCAACACTTTGGNNNGCCGAG
       :::  :::::::::: ::::::::::::::::::::::::::::::::::::  :  :::
s55T9  CCNTGGCGGCCGCGGGA-TTCGATTAAATATAAGCAATCCCAACACTTTGGGGGGGTGAG
            30         40         50         60         70         80

90        100        110        120        130
s45T9  GCGGGCGGATCAC--GAGGTCAGGAGATGGAGACCATCCTGGCTAACACAGTGAAACCCT
       :::: : ::::::  :::: :::  :::  ::::::: ::: ::: ::: ::::  :
s55T9  GCGGACAGATCACTTGAGGTCAGGGGTTTGAGACCAGCATGGCCAACGTGGTGAAAAC--
            90        100        110        120        130        140
```

310       320       330       340       350       360
B2         TGAGCCGAGATTGTGCCACTGCACTCCAGCCTGGGCAACAGAGCGAGACTCCATCTCAAA
           ::::::::::::::::::::::::::::::::::::::::::::::::::::::::::::
s55M1      TGAGCCGAGATTGTGCCACTGCACTCCAGCCTGGGCAACAGAGCGAGACTCCATCTCAAA
           250       260       270       280       290       300

370       380       390       400       410       420
B2         AAAAAAAAAAAAATCACCCCAAAGCAATAAGGAGAACTAGAACAGGACATACACTCCAACA
           ::::::::::::::::::::::::::::::::::::::::::::::::::::::::::::
s55M1      AAAAAAAAAAAAATCACCCCAAAGCAATAAGGAGAACTAGAACAGGACATACACTCCAACA
           310       320       330       340       350       360

430       440       450       460       470       480
B2         CTGGTGAAACTAGGAAAACATATGTAACCCCAAACCACAATATATACACACAAAACTATA
           ::::::::::::::::::::::::::::::::::::::::::::::::::::::::::::
s55M1      CTGGTGAAACTAGGAAAACATATGTAACCCCAAACCACAATATATACACACAAAACTATA
           370       380       390       400       410       420

490       500       510       520       530       540
B2         CGAGATGTGGGATCCTATATAAT  (SEQ ID NO:174)
           :::::::::::::::::::::::
s55M1      CGAGATGTGGGATCCTATATAAT  (SEQ ID NO:175)
```

Figure 19

UUGGUAACGACCAUGCCAC (SEQ ID NO:176)

GUGGCAUGGUCGUUACCAA dTdT (SEQ ID NO:180)
dTdT CACCGUACCAGCAAUGGUU (SEQ ID NO:181)

UUCACUUAGAAUAAUGUCC (SEQ ID NO:177)

GGACAUUAUUCUAAGUGAA dTdT (SEQ ID NO:182)
dTdT CCUGUAAUAAGAUUCACUU (SEQ ID NO:183)

UCUUUGUGUGAAUUUGACAAAC (SEQ ID NO:178)

GUUGUCAAAUUCACAAAGA dTdT (SEQ ID NO:184)
dTdT CAACAGUUUAAGUGUUUCU (SEQ ID NO:185)

UCAAGGUCCAGGCUACAAC (SEQ ID NO:179)

GUUGUAGCCUGGACCUUGA dTdT (SEQ ID NO:186)
dTdT CAACAUCGGACCUGGAACU (SEQ ID NO:187)

Study of the overexpression of genes of the Liv21 complex in cytoplasmic and nuclear fractions of MCF7 cells "equivalent" of breast cancer cells. Comparing these surexpressions or expressions of genes or sequences nucleotide tissue proliferation versus healthy tissues or cells quiescent.

Example biochip.

TGFBetarecept meaavaaprp rlllivlsas aaaaaallpg stalqcfchi ctkdnfrcvt dqlcfvsvte
 61 ttdkvihnsm ciseidllpr drpfvcapss ktgsvtrtyc cnqdhcnkie lpttvksspg
121 lgpvelaavi agpvcfvcis lm (SEQ ID NO:160)

Catalytic Moiety lqesigkgrf gevwrgkwrg esvavkifss rearswfres eiyqtvmlrh enilgflaad
 61 nkdngtwtql wlvsdyhehg slfdylaryt vtvegmikla lstasglahl hmeivgtqgk
121 paiahrdlks knilvkkngt cciadlglav rhdsatdtid iapnhcvgtk rymapevldd
181 sinmkhfesf kradiyamgl vfwelarrcs iggihsdyql pyydlvpsdp svaemrkvvc
241 egklrpnipn rwqscsalrv makimrecwy angaarltai nikk (SEQ ID NO:161)

E2F2

// leucine zipper :
lnwaaevldv qkrriyditn vl (SEQ ID NO:188)

Dimerization Region

1 mfedptrpgk qqqigqelke lmategaldq liqscslsfk hltsdkankr layvtyqdir
 61 avgnfkeqtv iavkappqtr levpdrteda lql (SEQ ID NO:155)
transactivation region
  1 appppslvpl eatcsllelp hpllqqtedq flspriacss pliefspsld qddylwglsa
 61 gegisdlfds ydigdllin (SEQ ID NO:156)
retinobastome region :
  1 ddylwgleag egisdlfd (SEQ ID NO:157)
region binding domain :
  1 gkcirvdglp spktpkspgs ktrydtslgl ltkkfiylls assdgvldln waaevldvqk
 61 rriyditnvl egiqlirkka knniqwvgrg (SEQ ID NO:158)
// region tdp : domain helice
rydtslgllt kkfiyllses edgvldlnwa aevldvqkrr iydinnvleg iqlirkkakn
 61 niqwvg (SEQ ID NO:159)
PKC
mvvfngllki kiceavslkp tawslrhavg prpqtflldp yialnvddsr igqtetkqkt
 61 nspawhdefv tdvcngrkie lavfhdapig yddfvancri qfeellqngs rhfedwidle
121 pegrvyviid lsgasgsaspk dneervfrer mrprkrqgav rrrvhqvsgh kfmatylrqp
181 tyashsrdfi wgviqkgyq cqvctcvvhk rchsliitkc aglkkqstpd qvgsqrfsvn
241 mphkfgihny kvptfcdhcg sliwqllrqg lqckvckmav hrrcetnvap ncgvdargia
301 kvladlgvtp dkitnsgqrr kkliaqaesp qpasgsspse edraksapts pcdqeikele
361 snirkalsfd nrgeahraas spdgqlmspg angevrqgqa krlgldefnf ikvigkgsfg
421 kvmlaelkgk devyavkvlk kdvilqdddv dctmtekril alarkhpylt qlyccfqtkd
481 rlffvmeyvn ggdlmfqiqr srkfdeprsr fyaaevtsal mflhqhgviy rdlkldnill
541 daeghchkiad fgmckegiln gvttttfcgt pdyiapeilq eleygpsvdw walgvlayem
601 magqppfead neddlfesil hddvlypvwl skeavsilka fmtknphkrl gcvasqnged
661 aikqhpffke idwvlleqkk ikppfkprik tkrdvnnfdq dftrsepvlt lvdeaivkqi
721 nqeefkgfsy fgedlmp (SEQ ID NO:162)

Mass Spectroscopy (Fig. 5); Interaction Scheme (Fig. 2)
RAB1-Human (normal) P29762

Figure 22B

Ost6 DNA Genome

```
  1 gatcacctga ggccaggagt ttgagaccag cctggccaac atggcaaaac cccatctcta
    ctaaaaatac aaaaattagc ctgcgtggtg acgagtgcct gtaatcccag ctattcggga
121 ggctgaggca ggagaatcaa ttgaacccgg gaggtggagg ttgcagtgag ccaagatcgt
181 gccactgcac cccagcctgg gcaacagagc gagactctgt ctcaaaaaaa gaaaatgaaa
241 aagacatgct taaattttag cttccatttc tcatcttcta aagccatgct tctcaaacat
301 gagtgagcag acccaggaat cttgttaaaa tgggattcc gatcaagggg cctggagg
361 agcctgaggt cctgccttc aaaccagctc ccagatgggc ctgatgctga caccagtaaa
421 ctccctttgc acacaagcct gtttaggctg ggtcttctcc aatttgcaca cacagtatcc
481 cagcatgac atttcagaaac atcaagcttg ttcttttcctg cccttgatt ctgcttttttg
541 ttctgtgtct tctcttgagc cccttggtg tgcttttttgt tctgtgcctt ctcttaagcc
601 ctgccctctg cttggaatgc tctctgccac ctcttcactc ctcctccagg aaacccttcct
661 tgactgcctg ctctctgccc tgcgaggact ctgggagca gactttgagg agcaggctcc
```
(SEQ ID NO:149)

Acnm
```
  1 agcctgagcc gatggtaacg agtggtactg tttccgtttc ttttccatct attgaacctt
 61 tctcaagcat tttcagctct gaactttaat tccagactgt attttctgtg agtcctgatc
121 aagtgataca aatgagctgc aatggtgaca taaactcttg acagagattg aaaagtagc
181 tggaacaccca tctttttctt taactttttca tggtgcttct gttggcatag ttggggaaag
241 cacctacaca atgagttta tcatgaagct tcacagacac ttccaagaa cagtcattct
301 gcttgcaact ttttgtatgg tgagcattat catttctgct tactacctgt acagtggcta
361 caaacaggaa aatgaactct ctgagacggc ttcagaagtt gactgtgcg acctccaaca
421 cctaccatat caactaatgg aagtgaaagc aatgaatctt ttgatgcct caaggacaga
481 ccccacagtc ctagtatttg tagagagcca gtactcatct cttggtcaag acatcattat
541 gatctagaa tcaagtagat tcaagtatca cattgaaatt gccctggaa agggagatct
601 cccagtgctt atagacaaaa tgaaaggcaa atacattctc attatttatg agaatatttt
661 aaagtatata aatatgatt cctggaatcg aagccttcta gataaatact gtgtagaatc
721 tggtgtgggt gtcattggat tccacaaaac tagtgagaag agtgtacaga gctttcagtt
781 aaaaggtttc ccttttttcca tatatggaaa tcttgcagta aaagattgtt gtattaactgc
841 tcattctcca ttgattcgta tgaccagact tccaagctt gaaaaaaggtt cttttacctgg
901 aactgactgg acagttttttc agattaatca ttcagcctat caaccagtaa tatttgccaa
961 agtaaagacc ccagaaaacc tttctccttc catctctaaa ggtgcttttt atgccactat
1021 tatacatgac ctggggcttc atgatggaat tcaaagggtt cttttggca acaacttgaa
1081 cttttggctg cacaagctca tcttcataga tgccatctcc ttattatcag ggaagaggct
1141 gacactgtcc ttggacaggt acattcttgt ggatattgat gatacattg cggaaaaga
1201 gggaacaaga atgaacacca atgatgtaaa ggcctgctt gatactcaga atctttgcg
1261 tgacaaatc acaaattta catcaacct gggatttca gggaaatttt cctatcagg
1321 aactgaagag gaagatgaag gagatgactg tctgttgggg tctgtggatg agtcctggtg
1381 gtttcctcac atgtggagcc atatgcagcc ccacctcttc cacaatgagt catctttggt
1441 ggacagatg attctcaaca aaagatttgc cttagagcac ggcattccaa cggacgtggg
1501 ctacgctgtg gccccctcacc attcgggc ctaccctgta catgttcagc tttatgaggc
1561 ctggaagaag gtctggaata ttaaaatcac cagcactgaa gaatatcacc atctgaagcc
1621 agctagatac cggaggggtt ttatccaaaa aaacatcatg gttctccaaa gacaaaactg
1681 tggcttttc actcacacca ttttctacaa agaatatcca ggggtcccta aagagctgga
1741 taagagtatc caaggaggga aactttttctt cactgtcgtc ctcaaacccta tcagcatttc
1801 catgacccat ttgtccaact atgggaatga ccgactggga ttatatacat ctgttaatct
1861 ggccaacttt gtgaagagct ggaccaacct gcgacttcag actctgcctc cagtacaact
1921 ggccacaaag tattttgagc tgtttcctga tcagaaagac cctctctggc agaatccttg
1981 cgatgacaaa cgccacagag acatttggtc taagaaaaaa acttgtgatc gcttaccaaa
2041 attcttggta ataggacccc agaaaactgg taccactgct ttgtatttgt tctgttat
2101 gcaccttcc atccttagta actcccccag cccaaaaacc tttgaggagg tacagttcttt
2161 taatagaaat aactaccaca gggggattga ttggtatatg gattccttcc cagtcccaca
```
(SEQ ID NO:148)

```
                      /gene="SUMO1"
                      /note="polyA tail: 15 bases do not align to the human
                       genome."
ORIGIN
  1 gaagttactg cagccgcggt gttgtgctgt gggaaggga gaaggatttg taaacccgg
```

Figure 22C

```
  61 agcgaggttc tgcttacccg aggccgctgc tgtgcggaga ccccgggtg aagccaccgt
 121 catcatgtct gaccaggagg caaaaccttc aactgaggac ttggggata agaaggaagg
 181 tgaatatatt aaactcaaag tcattggaca ggacagcagt gagattcact tcaaagtgaa
 241 aatgacaaca catctcaaga aactcaaaga atcatactgt caaagacagg gtgttccaat
 301 gaattcactc aggtttctct ttgagggtca gagaattgct gataataata ctccaaaaga
 361 actgggaatg gaggaagaag atgtgattga agtttatcag gaacaaacgg ggggtcattc
 421 aacagtttag atattctttt tattttttt cttttccctc aatccttttt tattttaaa
 481 aatagttctt ttgtaatgtg gtgttcaaaa cggaattgaa aactggcacc ccatctcttt
 541 gaaacatctg gtaatttgaa ttctagtgct cattattcat tattgtttgt tttcattgtg
 601 ctgattttg gtgatcaagc ctcagtcccc ttcatattac cctctcctt ttaaaatca
 661 cgtgtgcaca gagaggtcac cttttcagg acattgcatt ttcaggcttg tggtgataaa
 721 taagatcgac caatgcaagt gttcataatg aactttccaat tggccctgat gctctagcat
 781 gtgattactt cactcctgga ctgtgacttt cagtgggaga tggaagtttt tcagagaact
 841 gaactgtgga aaatgacct ttccttaact tgaagctact tttaaaattt gagggtctgg
 901 accaaagaa gaggaatatc aggttgaagt caagatgaca gataaggtga gagtaatgac
 961 taactccaaa gatggcttca ctgaagaaaa ggcattttaa gatcttttaa aaatcttgtc
1021 agaagatccc agaaaagttc taattttcat tagcaattaa taaagtctata catgcagaaa
1081 tgaatacaac agaacactgc (SEQ ID NO:145)
```

>P63165|SUMO1_HUMAN Small ubiquitin-related modifier 1 - Homo sapiens (Human)

MSDQEAKPSTEDLGDKKEGEYIKLKVIGQDSSEIHFKVKMTTHLKKLKESYCQRQGVPMN
SLRFLFEGQRIADNHTPKELGMEEEDVIEVYQEQTGGHSTV (SEQ ID NO:165)

25kD
>P09497|CLCB_HUMAN Clathrin light chain B - Homo sapiens (Human)
MAUDFGFFSSSESGAPEAAEEDPAAAFLAQQESEIAGIENDEGFGAPAGSHAAPAQPGPT
SGACSEDHGTTVNGDVFQEANGPADGYAAIAQADRLTQEPESTRKWRSEQRKRLQELDAA
SKVTEQEWREKAKKDLEEWNQRQSEQVEKNKINNRIAOKAFYQQPDADIIGYVASEEAFV
KESKEETPGTEHEKVAQLCDFNPKSSKQCKDVSRLRSVLMSLKQTPLSR (SEQ ID NO:166)

On ARNM sur 6

```
  1 cgcgggagc cggcgtcggc gaggacgggc ttggcgcgga ccgcacttcc tctccgccac
 61 cgggcccagc tccccgcggc tcgggtgaca gcgtcgcggc cgccggacgc agcgcgggc
121 aggcgcgggc agagccgagc gcagcggagg ctccggccgga ggcgcgggga aaatggctga
181 tgactttggc ttcttctcgt cgtcggagag cggtgccccg gaggcggccg aggaggaccc
241 ggcggccgcc ttcctggccc agcaggagag cgagattgca ggcatagaga acgacgaggg
301 cttcggggca cctgccggca gcatgcggc cccgcgcag cggcccca cgagtggggc
361 tggttctgag gacatgggga ccacagtcaa tggagatgtg tttcaggagg ccaacggtcc
421 tgctgatggc tacgcagcca ttgccaggc tgacaggctg acccaggagc ctgagagcat
481 ccgcaagtgg cgagaggayc agaggaaacg gctgcaagag ctggatgctg catctaaggt
541 cacggaacag gaatggcggg agaaggccaa gaaygacctg gaggagtgga accagcgcca
601 gagtgaacaa gtagagaaga acaagatcaa caaccggatc gctgacaaag cattctacca
661 gcagccagat gctyatatca tcggctacgt ggcatccgag gaggctttcg tgaaggaatc
721 caaggaggag accccaggca cagagtggga gaaggtggcc cagctatgtg acttcaacco
731 caagagcagc (SEQ ID NO:146)
```

>Q8N6B3|Q8N6B3_HUMAN Myeloid/lymphoid or mixed-lineage leukemia/clathrin assembly protein fusion protein (Fragment) - Homo sapiens (Human).

EKPPPVNKQENAGTLNILSTLSNGNSSKQKIPADGVHRIRVDFKQVGIDRGDIPDLSQ (SEQ ID NO:167)

DEFINITION  Homo sapiens mRNA for vacuolar-type H(+)-ATPase 115 kDa
subunit.
ACCESSION   Z71460 U73006
VERSION     Z71460.1  GI:1638834
SVKSLAGGLVLFFFFTAFATLTVAILLIMEGLSAFLHALR
LHHVEFQNKFYSGTGFKFLPFSFEHIREGKFEE" (SEQ ID NO:168)

```
2641 tcgggaaggg aagtttgaag agtgagtccc tgtgagggcc gtgtgcccat gctacoctcc
2701 ctgcctccct ccacagtgat cagctgttga cctctctgcc tgttggttgt gatctgtggg
2761 caccagctca ttcgtgtcac cctgtctgtg agtcatttag atagaatagt cctccttggg
2821 tctcccacca cccctagctt tgtgtgtagt gtagtgattt tctggctgtc accatactc
2881 actgggcacc agccttgccc tcttagcctc catccatcca gacagcgctt cccacctcct
2941 ggtggtgagc cagtctgcat tccacgcca tcccaaagcc ctttcatctt cccgtgcat
```

Figure 22D

```
3001 tgtagatgga aggagcaccc atgccattca ccc (SEQ ID NO:147)
Heavy chain 2 CLH22
```

RNA on 6

```
   1 attcctgccg ctgccgccgc cgccgccgag gtcccgcacc agccatggcg cagatcctcc
  61 ctgttcgctt tcaggagcac ttccagctcc aaaaccttgg aattaatcca gctaacattg
 121 gattcagcac actgaccatg gaatctgaca agttcatatg tatccgagag aaagttggtg
 181 agcaggcaca ggtcacgatc attgacatga gtgacccaat ggctccgatc cgacggccta
 241 tctctgcaga gagtgccatc atgaatccag cctctaaggt gatagctctg aaagctggga
 301 agacacttca gatctttaat attgagatga agagtaaaat gaaggctcat actatggcag
 361 aagaagtgat tttctggaaa tgggttttctg tgaatactgt tgccttggtg accgagaccg
 421 cggtctacca ctggagcatg gaaggtgact cccagcccat gaagatgttt gatagacata
 481 ccagtctggt gggctgccag gtgattcact accggactga tgagtaccag aagtggctgc
 541 tgctcgtagg catctcggct cagcaaaacc gtgtggttgg agcaatgcag ctctactctg
 601 tggataggaa ggtttcacaa cccatagaag gccatgctgc ggcttttgca gagttcaaga
 661 tggaggggaa tgccaagcct gccacccttt tctgctttgc tgtacgtaat cccacaggag
 721 gcaagttgca catcattgaa gttggacagc ctgcagcggg aaaccaacct tttgtaaaga
 781 aagcagtaga tgtgtttttt cctccagagg cacagaatga ttttccagtg gctatgcaga
 841 ttggagctaa acatggtgtt atttacttga tcacaaagta tggctatctt catctgtacg
 901 acctagagtc tggcgtgtgc atctgcatga accgtattag tgctgacaca atatttgtca
 961 ctgctccaca caaaccaacc tctggaatta ttggtgtcaa caaaaaagga caggtactgt
1021 cagtttgtgt tgaggaagat aacattgtga attatgcaac caacgtgctt cagaatccag
1081 accttggtct gcgtttggcc gttcgtagta acctggctgg ggcagagaag ttgtttgtga
1141 gaaaattcaa taccctcttt gcacagggca gctatgctga agccgccaaa gttgcagcgt
     (SEQ ID NO:144)
```

RIKEN Craab

Nuclear localization signal
RRMKWKK (SEQ ID NO:169)

Transactivation Domain
LYKDPCAFQR (SEQ ID NO:170)

E2F4

P4 Add the Clatherine and Functions

PHARMACODIAGNOSTIC TEST TARGETING ONCOLOGY AND NEURODEGENERATION

FIELD OF THE INVENTION

The present invention relates to the field of medicine and biology. It concerns a novel test for screening and for therapeutic follow-up in oncology. More particularly, it relates to diagnostic and/or therapeutic tests in oncology and on neurodegenerative diseases. Molecular targeting by peptide vectors and antibodies or by small interfering RNAs (siRNAs) opens a new concept of interdependence for diagnostic and therapeutic tools. Indeed, they now go hand in hand, thus opening the path to pharmacodiagnosis. Proper understanding of the balance between over and under expression of genes according to their location in different cellular compartments and as a function of the proliferation state opens new perspectives for a more accurate differential analysis.

DESCRIPTION OF THE STATE OF THE ART

Age-related neurodegenerative diseases and cancers both involve a modification of the physiological process of programmed cell death or apoptosis. Neuronal death is abnormally accelerated during neurodegenerative diseases such as Alzheimer's disease, Huntington's disease, Parkinson's disease, etc. On the other hand, the cancerization process corresponds to a blocking of apoptosis, which results in an uncontrolled multiplication of cells. The link between these two processes has currently become a major field of investigation in research on aging.

The control of the balance between cell division (mitosis), differentiation and programmed cell death (apoptosis) is fundamental during normal physiological processes, including embryonic development, tissue regeneration and aging. An impairment of this balance can lead to major pathological situations such as the formation of tumors or some neurodegenerative diseases.

Cancer is one of the principal causes of mortality throughout the world. Over the course of the last generation, while the percentages of deaths related to cardiac and cardiovascular diseases and a large number of other diseases has decreased, the number of deaths related to the various forms of cancer has increased.

Despite the rapid advance in our understanding of the various forms of cancer, the low survival rates can generally be attributed to inadequate diagnosis and inadequate treatment. Most tumors can only be detected when they reach a size of approximately 1 cm. Since a continuously developing tumor takes a relatively short period of time to evolve to a stage which is incompatible with survival, this leaves little time for a therapeutic intervention. Early diagnosis therefore becomes the key to success for the treatment of cancer.

For a multitude of reasons, early diagnosis remains illusory for most forms of cancer. For certain forms of cancer, disease-specific markers are not available or are only available at an advanced stage of the disease, making diagnosis difficult. In other forms of cancer, the markers are available but are not always specific for the disease or they may be associated with its benign form.

Skin cancer, for example, is the most widespread cancer in Canada. In 1992 alone, 50 300 new cases of skin cancer were reported, compared with 19 300 cases of lung cancer, 16 200 cases of colorectal cancer and 15 700 cases of breast cancer. In other words, skin cancer is as common as the three main types of cancer combined. Its incidence continues to increase, with 64 200 new cases thereof in 1997, corresponding to an increase of 14 000 cases in 5 years. In particular, the incidence of malignant melanoma is increasing at a rate of 2% per year. Early diagnosis remains the key to an effective treatment. A malignant tumor is readily accessible and can be removed with minor surgery. In fact, recovery is 100% if skin cancer is detected early enough. Early diagnosis of skin cancer remains, however, difficult. This type of cancer is not just a single disease but an entire range of conditions related to one another, which appear similar in many cases upon visual inspection. A diagnosis on the basis of such an inspection is therefore subjective. A basocellular epithelioma or a spinocellular epithelioma have very different clinical developments. A basocellular epithelioma spreads out laterally over the surface of the skin, without penetrating into the deeper skin layers. Thus, although it can be disfiguring, a basocellular epithelioma rarely develops metastases and is rarely fatal. However, a spinocellular epithelioma causes metastases and is often fatal. Therefore it becomes important to be able to distinguish between these two types of skin cancer and to be able to locally treat them by molecular targeting such as small interfering RNA (siRNA). A definitive diagnosis of skin cancer requires a biopsy and histological analysis.

Colon cancer is the third most common cause of cancer-related mortality in men and women in North America (16 200 cases per year). Early detection, leading to an early intervention, has demonstrated that treatment success and survival rate can be improved. For example, the 5-year survival rate is 92% for a patient whose disease was detected at an early stage, whereas the rate drops to approximately 60% in patients with a localized cancer, and to approximately 6% in those with metastases. However, only a third of colon cancers are detected at an early stage. One of the reasons for this delay in diagnosis is the absence of a sensitive, relatively inexpensive, non-invasive screening test.

Breast cancer is one of the most common cancers in women, together with colon cancer. The mortality rate is the highest among cancers affecting women.

There are very few diagnostic markers allowing the detection of breast cancer and they only have a predictive value of 20%. There are no markers, either, which can detect or determine the invasiveness or the aggressiveness of metastatic cancer cells or which permit therapeutic monitoring. Given its heterogeneity, breast cancer has the greatest interest in being studied by biochips, which would allow therapeutic adjustments depending on the under and over expression of genes of the Liv21 complex.

Over the last few years, considerable progress has been made in understanding how oncogenes and tumor suppressor genes regulate cell proliferation and apoptosis. One of the main targets of these regulators is the family of E2F-type transcription factors (E2F1, E2F2, E2F3, E2F4 etc. . . . ) in the E2F and RB protein signalling pathway. These proteins play a central role in controlling cell division by coupling the regulation of the genes required for progression of the cell cycle with extracellular signals (mitogens, proliferation inhibitors). They behave as oncogenes by stimulating tumor cell proliferation.

Among the expressed genes are found:
overexpression of the E2F4 transcription factor and the c-myc oncogene which induce apoptosis of post-mitotic cells by accumulation of oxygenated reactants (Tanaka, 2002);
the gene p53, which belongs to the tumor suppressor gene family, blocks the cell cycle in the case of DNA lesion. It has now been demonstrated that this gene is also involved in the progression of apoptosis (Oren, 1994; Yonish-Rouach, 1996);

the cyclin D1, one of the proteins constituting the regulatory subunits of cell cycle kinases, which is essential for cell cycle progression. This protein is also expressed during apoptosis in various cell types (Han et al, 1996; Pardo et al, 1996).

chk1 and 2, crb2, p21 and other oncogenes and cytokines such as TNF alpha etc....

It would be of great interest to have novel diagnostic methods detecting the presence of cancer with greater specificity and making it possible to distinguish between aggressive cancer cells with the tendency to metastasize and those which are more localized and have a lower probability of metastasizing. A marker capable of revealing cell proliferation would therefore be of great use. ki 67 and Caf1 are nuclear markers indicating the proliferation state of many cancers (Almouzny; Curie Institut). LIV21 complex genes will be the cytoplasmic markers at least equal and complementary to the previously identified nuclear ones.

SUMMARY OF THE INVENTION

The present invention concerns a novel test for screening for reinduction of the cell cycle targeting oncology. It is a diagnostic test and a prognostic test for various cancers (breast cancer, bladder cancer, ovarian cancer, lung cancer, skin cancer, prostate cancer, colon cancer, liver cancer, glioblastoma, sarcoma, leukemia, etc.). More particularly, the invention concerns the use of the genes or proteins of the Liv21 complex and of their derivatives as therapeutic tools or as diagnostic and prognostic markers for cancers. The invention therefore concerns the detection of the LIV21 gene or LIV21 protein with a kit comprising LIV21-specific antibodies or LIV21 specific probes. The present invention also consist in using all the proliferation markers and transcription factors which play a role in the cancerization and—in some cases—neurodegeneration process.

Thus, the invention lies in the fabrication of diagnostic DNA, proteins and antibody arrays including known antibodies directed against various proteins of the LIV21-associated complex according to the phases of the cell cycle, that is, without restriction thereto, antibodies specific for RBP2, E2F4, E2F1, SUMO, HDAC1, crb2, Int2, cmd2, cycE/cdk2, cdk1, CREB1 and p300, Rb, p107 and p130 of the pocket protein family. In addition, antibodies specific for NFkB, cdc2A, mdm2, p21, p53, p65, Ki67 CAF1, cyclins A and D1.

The protein arrays will make it possible to study protein interactions and post-translational modifications, more particularly phosphorylations and methylations of certain proteins, which signal a characteristic state of the diseased cell different to protein interactions and metabolism in normal cell. The state of expression and of silencing of certain genes is different in diseased cells and in normal cells. The DNA arrays will permit to study in the nuclear cells extracts and in addition cytoplasmic or membrane cell extracts the under expressions or over expressions of genes and the ratio between genes and between proteins of the Liv21 complex and associated partners.

A first objective of the present invention is to demonstrate a method for the detection and prognosis of cancer and of its metastatic potential. Preferably, the cancer is selected from breast cancer, bladder cancer, ovarian cancer, lung cancer, skin cancer, prostate cancer, colon cancer, liver cancer, a sarcoma, a leukemia and glyoblastoma, without being limited thereto.

One aspect of the present invention consists of the use of LIV21 complex as a prognostic indicator for cancer and his therapeutic monitoring. We define the Liv21 complex by the protein extract and peptides studied by mass spectrometry such as Maldi and ESIMSMS or Maldi TofTof. The said extract has been obtaining by binding of the Liv21 complex to one of its polyclonal antibodies described in the patent (PCT/FR2006/000510). The complex is defined by its mass spectrometry global profile (FIG. 5) and the number and the molecular weight of protein extracts bands obtained on the acrylamide gels of FIGS. 1A and 1B as a function of temperature at which the sample is submitted and of described migration conditions.

In fact, when for example Liv21F peptide is located in the cytoplasm and we reveal directly for example by in situ hybridization or by biochip analysis its higher expression in the cytoplasm, the cancer cells in the tissues are aggressive. Conversely, when the LIV21 gene expression product or the expression of Liv21F peptide is preferentially located in the cell nucleus, this is a prognostic indicator that the cells of the tissue are differentiated and quiescent and therefore non-invasive. The effectiveness of a cancer treatment can also be monitored by the traceability of this Liv21 protein complex, and of its derivatives and ratios with the associated proteins but also by Diagmicroarray or biochip including among others this protein and its Liv21 associated complex (FIG. 20 and FIG. 21).

Moreover, detection of protein kinase C epsilon (PKCϵ) is also advantageous since it has been determined that PKCϵ phosphorylates the LIV21 protein in order to maintain it in the cytoplasm. Thus, a significant increase in PKCϵ is indicative of the presence of cancer cells. Moreover, the LIV21/PKCϵ ratio increases in the cytoplasmic fraction of cancer cells. The same is true of the detection of HDAC1, which has been shown to be involved in PML/SUMO/Rb/HDAC1. More generally, the HDACs family plays a key role in the regulation of gene expression. When the HDACs are overexpressed, they induce tumor suppressor gene silencing, hence the advantage of using HDAC inhibitors in therapy, combined with other inhibitors which regulate the metabolic pathway involving the Liv21 protein complex which contains the proteins: Liv21, E2F4, Histones H4, H3, SUMO, PML, Rb, E2F1 etc....

In addition, the detection of the E2F1 and/or E2F4 proteins is advantageous. In fact, the LIV21 protein forms a complex with E2F4, which is capable of inhibiting the expression of the E2F1 gene in the nucleus, E2F1 gene expression being a sign of cell proliferation. Thus, a decrease in the association of LIV21 with the E2F4 protein is indicative of the presence of cancer cells. Similarly, the presence of the E2F1 protein in the nucleus is indicative of the presence of cancer cells.

Consequently, the present invention concerns a method for the detection of cancer cells in a biological tissue sample (for example, breast, ovary, endometrium, bladder, melanoma, prostate, glioblastoma, etc.) from patients, this method comprising the detection of the products of expression of the LIV21 complex genes in the nucleus comparatively to the same products in the cytoplasm of the cells in the biological tissue sample from said patient. A localization of said products of expression of the LIV21 gene in the cytoplasm is indicative of the presence of cancer cells. A localization of said products of expression of the LIV21 complex genes in the nucleus is indicative of the presence of noncancer cells. Preferably, localization of said products of expression of the LIV21 complex genes in the cytoplasm are indicative of the presence of invasive and/or metastatic cancer cells.

Optionally, the method according to the present invention also comprises the detection of the product of expression of at least one gene selected from the group consisting of the protein kinase C epsilon (PKCε) gene, the E2F1 gene and the E2F4 gene. The method can in particular comprise the detection of the product of expression of two of these genes or of the three genes. Moreover, at least one of the ratios LIV21/PKCε, LIV21/E2F4 and LIV21/E2F1 can be determined in the present method. This ratio can be determined in the cytoplasm and/or in the nucleus preferably separated. Preferably, these ratios are determined in the nucleus. Preferably, these ratios are compared with those obtained in a normal cell.

The level of expression of each enzyme or polypeptide of the SUMO/Rb/HDAC complex or, for certain cell types, of the PML/SUMO/Rb/HDAC complex is an additional indicator of the proliferative state of the cell.

These ratios of expression or silencing can be detected via the protein expression or inhibition level themselves in the protein arrays (biochips) fabricated according to conventional methods described (Lubman David M, QIAO TIECH-ENG Alex, Mathew A B Y J etc. . . . ) or novel tools for the automation of hybridization and of reading, US2004152212 and Yu Xinglong US 2005019828 and novel supports which attach polypeptides, Klages Claus Peter.

Before describing the principle of these biochips, which are well known by man skilled in the art, we will give the following definitions:

The biological sample can be in particular sample of blood, serum, saliva, tissue, tumor, bone marrow, circling cells from the patient. The biological sample can be recovered by any type of sampling know by those skilled in the art. According to the present invention, we consider a biological sample any material allowing the detection of expression of a target gene. The biological material can include in particular proteins, or nucleic acids such as deoxyribonucleic acid (DNA) and ribonucleic acid (RNA). The nucleic acid can in particular be an RNA (ribonucleic acid). According to a preferred embodiment of the invention, the biological material comprises nucleic acids, in particular RNAs and even more specifically total RNAs. Total RNAs include transfer RNAs, messenger RNAs (mRNAs), such as mRNAs transcribed from the target gene, but also transcribed from any other gene, and ribosomal RNAs. This biological material includes specific material of the target gene, such as in particular mRNAs transcribed from the target gene or proteins issued from these RNAs, but it can also include material unspecific to the target gene, such as in particular mRNAs transcribed from a gene different from the target gene, tRNAs, rRNAs issued from other genes than the target gene. When the extracts to be studied consist of cell cultures, they will preferably be analyzed on fresh cultures (with or without previous treatment) that underwent an extraction protocol separating cellular compartments. This type of kit know by those skilled in the art allows the specific extraction of membranes or of solely the cytoplasmic or nuclear or cytoskeletal content in a differential fashion by using different solutions. For instance, the kit Proteo extract (ref 539790) from Calbiochem can be used.

The other aspect of the present invention is the use of the genes and the proteins mentioned above as markers for the invasiveness and the metastatic aggressiveness of cancer cells of the prostate, colon, bladder, melanoma, ovary, endometrium and cervix, and cancers in neurobiology or in ORL etc. . . . In fact, sequential pharmacodiagnostic tests during treatment monitoring will permit to observe, by comparing at different time points, variations of the expression level or of their silencing and therefore to better evaluate the treatment efficiency, to readjust these treatments in the case of a suitable multitherapy in such a way that the physiological equilibrium of the different products of genes involved in metabolic complexes are maintained. The plasticity of these equilibriums justifies the use of diagnostic biochips and for the therapeutic monitoring with the most pertinent genes of metabolic complexes involved in the physiology of anarchic proliferation in the case of breast cancer, which is highly heterogeneous. Therefore each individual or each phenotypic subgroup of individuals will show an under or over expression profile of genes of the metabolic complexes which is specific to him.

In one embodiment, the expression product of the genes is detected at the mRNA level. mRNA can de detected by RT-PCR analysis (cf following examples). It can also be detected by Northern blotting analysis.

In one alternative embodiment, the expression product of the genes is detected at the protein level or at the peptide level characterising the Liv21 complex and its interacting partners. Preferably, the protein and/or the Liv21 Protein complex is detected using a specific antibody. For example, the protein can be detected by Western blotting analysis and by SPR. In a preferred embodiment, it is detected by immunohistochemistry, immunocytochemistry, microfluidic or radiography, or by peroxidase labeling.

In one specific embodiment of the method comprising the detection of the expression product of the PKCε gene, a significant increase in PKCε is indicative of the presence of cancer cells. Moreover, the method can also comprise the determination of the LIV21/PKCε ratio in the nucleus, the membranes and the cytoplasm. This ratio can be compared with the one observed in a normal cell. An increase in the LIV21/PKCε ratio in the cytoplasmic fraction is indicative of cancer cells.

In another specific embodiment of the method comprising the detection of the expression product of the E2F4 gene, the method comprises the detection of the association of LIV21 with the E2F4 protein, a decrease in this association in the cell nucleus being indicative of the presence of cancer cells. Moreover, the method can also comprise the determination of the LIV21/E2F4 ratio in the nucleus and/or the cytoplasm. This ratio can be compared with the one observed in a normal cell.

In an additional embodiment of the method comprising the detection of the expression product of the E2F1 gene, the presence of the E2F1 protein in the nucleus is indicative of the presence of cancer cells. Moreover, the method can also comprise the determination of the LIV21/E2F1 ratio in the nucleus and/or the cytoplasm. This ratio can be compared with that observed in a normal cell.

In a specific embodiment, the method comprises the detection of a labelled small interfering RNA in order to target its specific sequence and therefore signal the locus of messenger RNA expression of the gene of interest. In this way, the specific small interfering RNA can be used as a diagnosis marker similarly to an antibody. The specific siRNA would allow to locate in a specific case such as in extemporaneous tissues or any kind of sample from a patient, such as cancer tissue sample, the fluorescence signal or any other marker used on the siRNA is found in a cellular compartment on the sample. An siRNA targeting the E2F1, E2F4 and PKC epsilon would allow a complementary diagnosis.

The method according to the present invention allows in particular the detection of metastasized cancer, therapeutic monitoring and/or recurrences following treatment.

A second aspect of the invention concerns the human LIV21 protein and also the fragments thereof. More particularly, the present invention concerns a purified or recombinant isolated human LIV21 protein. It concerns in particular an isolated polypeptide comprising a peptide sequence selected among SEQ ID Nos 1 to 5 and more broadly selected among the peptide sequences characterizing it and obtained by MALDI (FIGS. 3, 4 and 5) and NanoLC-ESI-MS.

In a preferred embodiment, the polypeptide comprises the three peptide sequences SEQ ID Nos 1 and 2 and 3. Preferably, the LIV21 complex comprises proteins with a leucine zipper motif, a basic domain characteristic of DNA binding domains, and a nuclearization sequence.

In an even more preferred embodiment, the present invention concerns the polypeptides with peptide sequences characterized by spectrograms of FIGS. 3, 4, 5 of gel bands 1, 2 and 3, selected among SEQ ID Nos 1 and 2 and 3 and 4 and 5 and a hundred additional non ordered sequences supplement (i.e. listing sequences in annex), the unmatched fragments identified in the Maldi T of analysis (cf. FIGS. 3, 4, 5), these unmatched fragments corresponding to the masses M (H+) untagged characterized in part the Liv21 protein and some elements of the Liv21 protein complex.

A third aspect of the invention concerns an antibody, which binds specifically to a polypeptide according to the present invention. More particularly, the antibody can bind specifically to a polypeptide comprising a peptide sequence selected from SEQ ID Nos 1-120, preferably from SEQ ID Nos 1 and 2 or 3 and/or 15 or 51, or a sequence having more than 80% identity to said sequences. The present invention concerns in particular an anti-LIV21 serum produced by immunizing an animal or a human with a polypeptide according to the present invention, in particular a polypeptide comprising a peptide sequence selected from SEQ ID Nos 1-120, preferably from SEQ ID Nos 1-5 and 51, or a sequence having 70%, 80% or 90% identity to said sequences.

A fourth aspect of the invention concerns a kit for the detection of cancer cells in a biological sample from a patient, this kit comprising one or more elements selected from the group consisting of an antibody which binds specifically to human LIV21 according to the present invention and an anti-LIV21 serum according to the present invention, a specific oligonucleotide mRNA probe of Liv21 and a pair of primers specific of mRNA. In a specific embodiment of the invention, the kit also comprises means for detecting the product of expression of a gene or a specific oligonucleotide mRNA probe of factors selected from the group consisting of the protein kinase C epsilon (PKCε) gene, the E2F1 gene and the E2F4 gene. But also the antibodies in a specific antibodies microarray from the antibodies group consisting of RBP2, SUMO, HDAC, TNFalpha, crb2, cycE/cdk2, cdk1, CREB1, p300, Rb, p107, p130, NFkB, cdc2A, mdm2, p21, p53, p65. It also comprises Microarray with said proteins above and specific peptides known by a person skilled in the art, their antigens being referenced. The combination of these different peptides corresponding to the specific interactions of protein complexes acting in metabolic deregulation, induces anarchical proliferation, which is a specific feature of cancer or neurodegeneration.

The invention concerns the use of an antibody specific for human LIV21 for the diagnosis of cancer, and antibodies specific for its protein complex, but also specific antibodies for RBP2, SUMO, HDAC, TNFalpha, crb2, cycE/cdk2, cdk1, CREB1, p300, Rb, PML, p107 and p130 NFKB, cdc2A, mdm2, p21, p53, p65.* Preferably, the diagnosis is performed ex vivo on samples from a patient (puncture, biopsy, ground cellular material, bronchial aspirations, DNA/protein/anti- bodies arrays, hydrophobic or ion metal supports, etc).

*Also, the invention concerns the used of primers pair or LIV21 specific probe for de cancer diagnosis.

DESCRIPTION OF THE FIGURES

FIG. 1B: Listing of sequences of LIV21 complex.

FIG. 3 A: The listing of monoisotopic peaks of the band 1 at 50 kD and the band 2 between 49 and 50 kD.

FIG. 5 bis is a table of the monoisotopic peaks of the third spectrogram corresponding to the one-dimensional acrylamide gel band migrating at 52 kD and revealed with coomassie blue and the LIV21 antibody. The monoisotopic peaks with a value M H+. The masses are give with three numbers after the decimal point by the proteomic platforms since they estimate that this is the acquisition precision limit of MALDI TOF machines.

Figure 4:
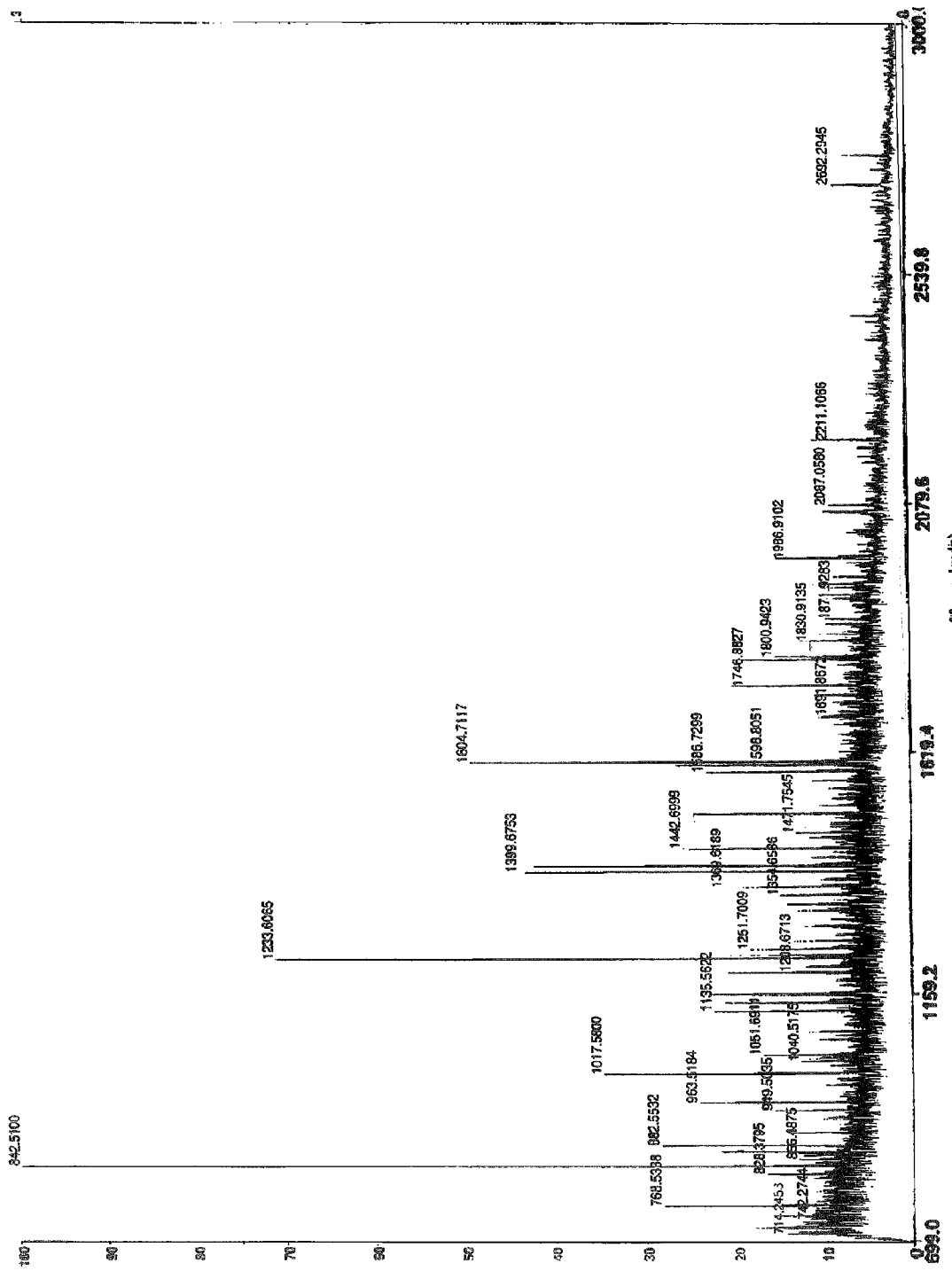
FIG. 4 is a profile of the spectrogram of the band 1.
Figure 5:
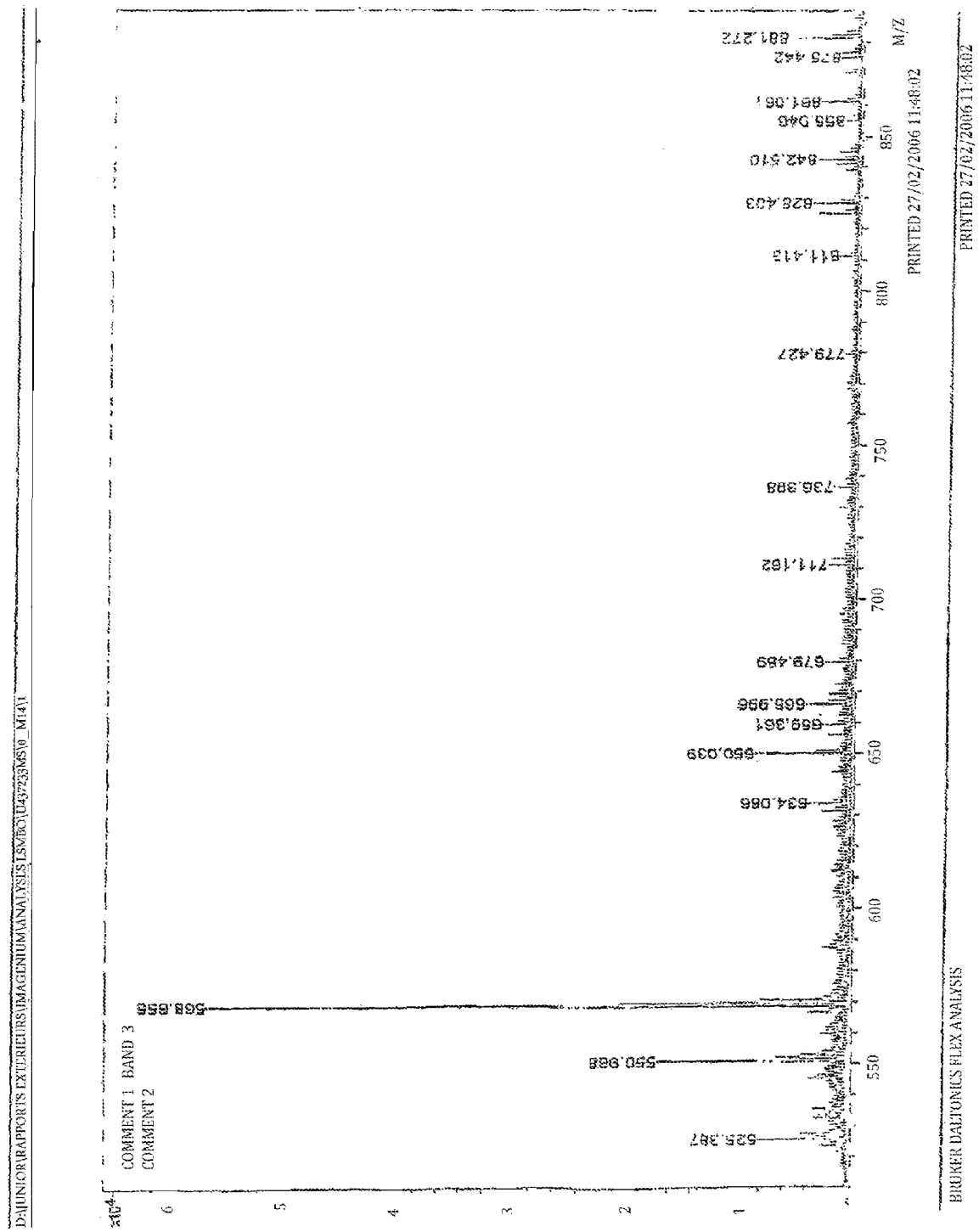
FIG. 5 is the third spectrogram corresponding to the one-dimensional 12% acrylamide gel band migrating at 51-52 kD and revealed with coomassie blue and the LIV21 antibody.
Figure 5:
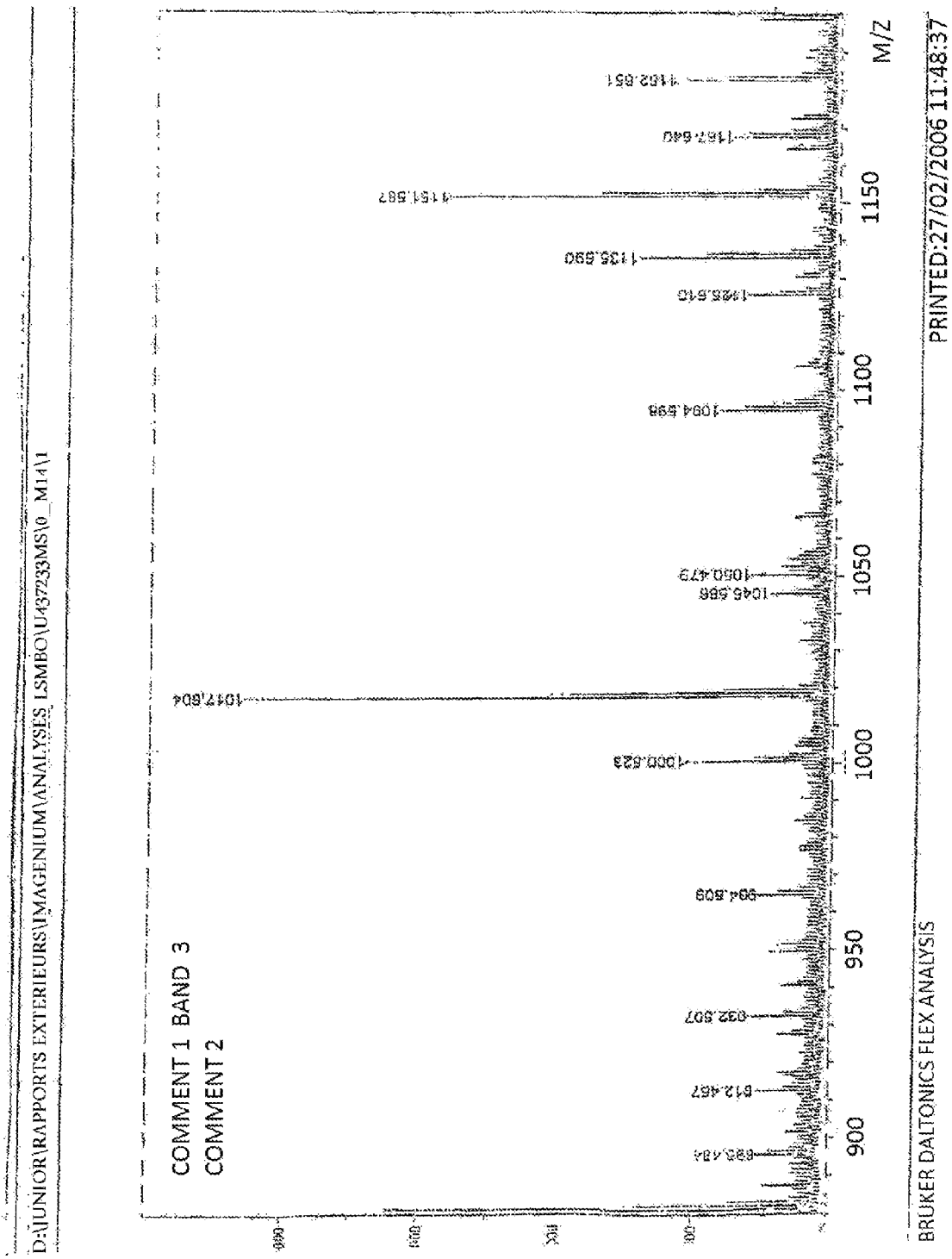
Figure 5:
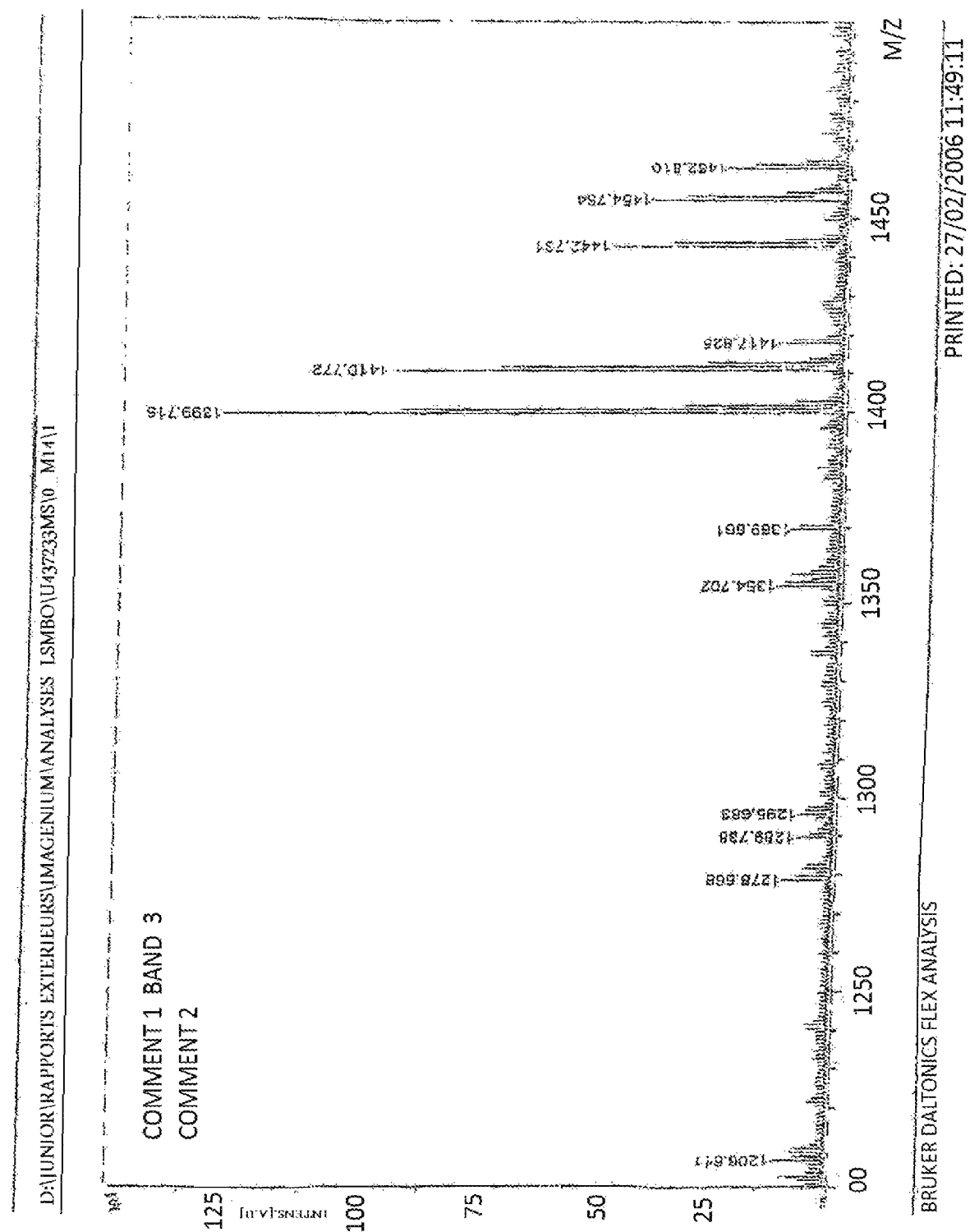
Figure 5:
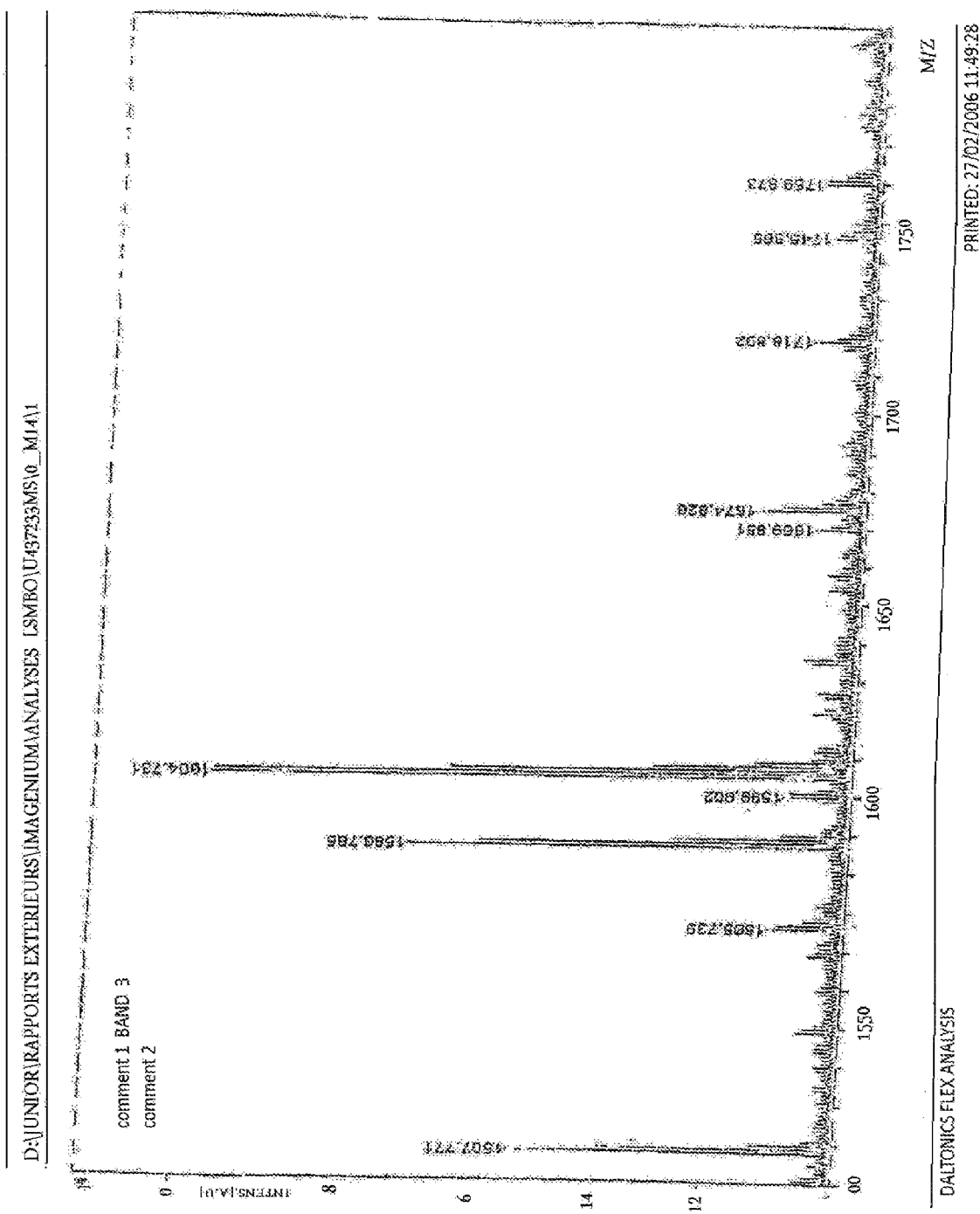
Figure 5:
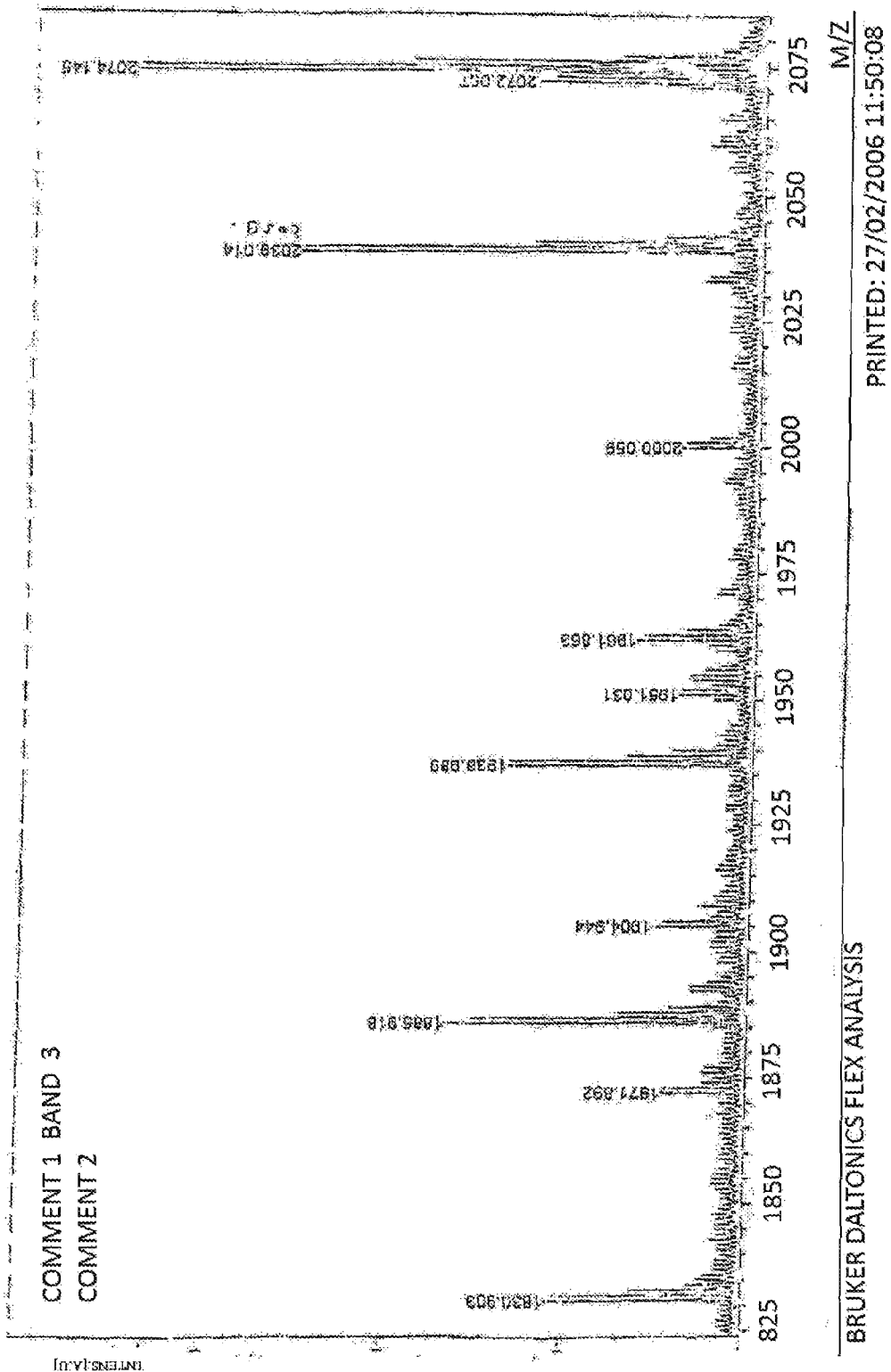
Figure 5:
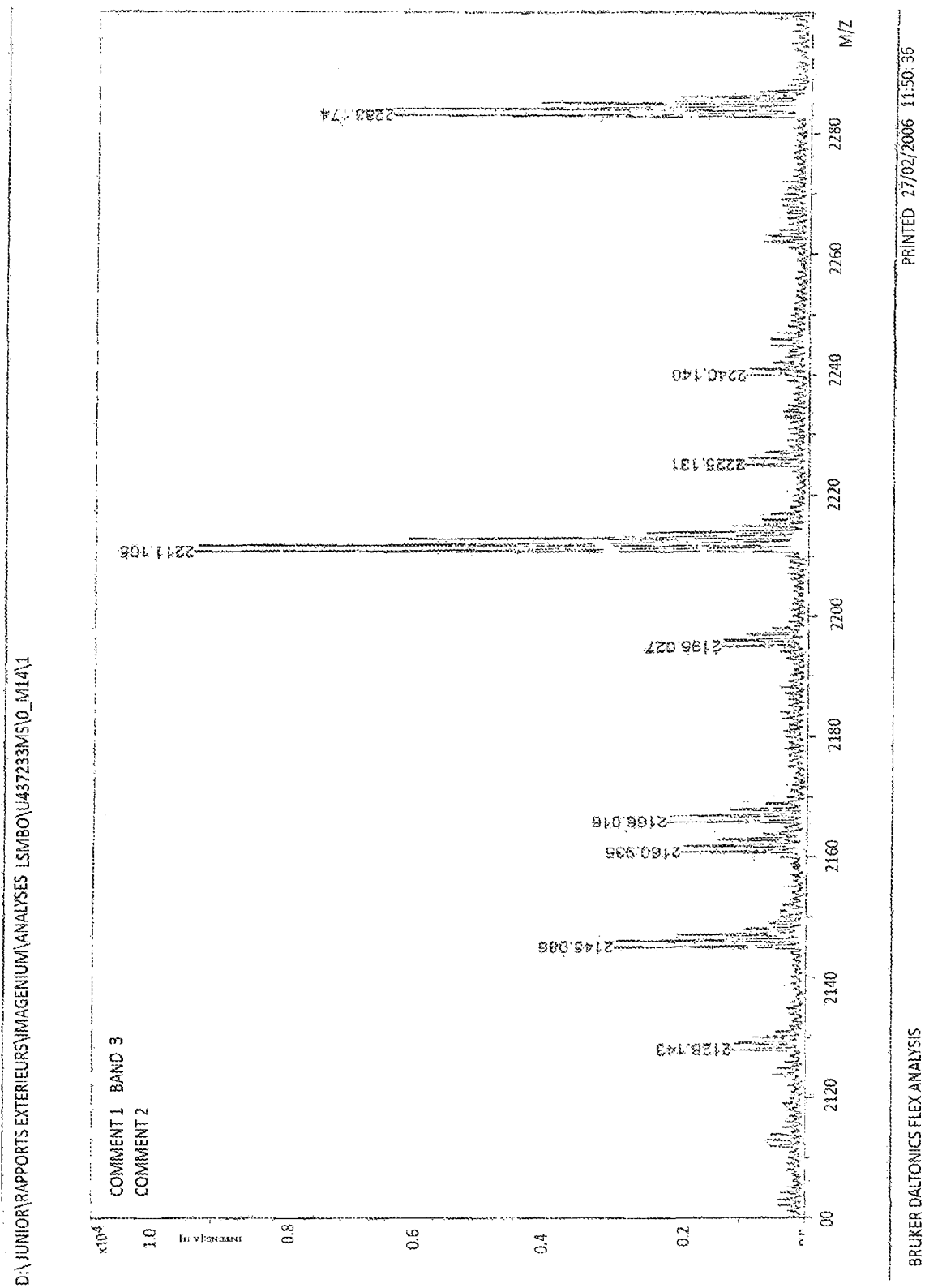
Figure 5:
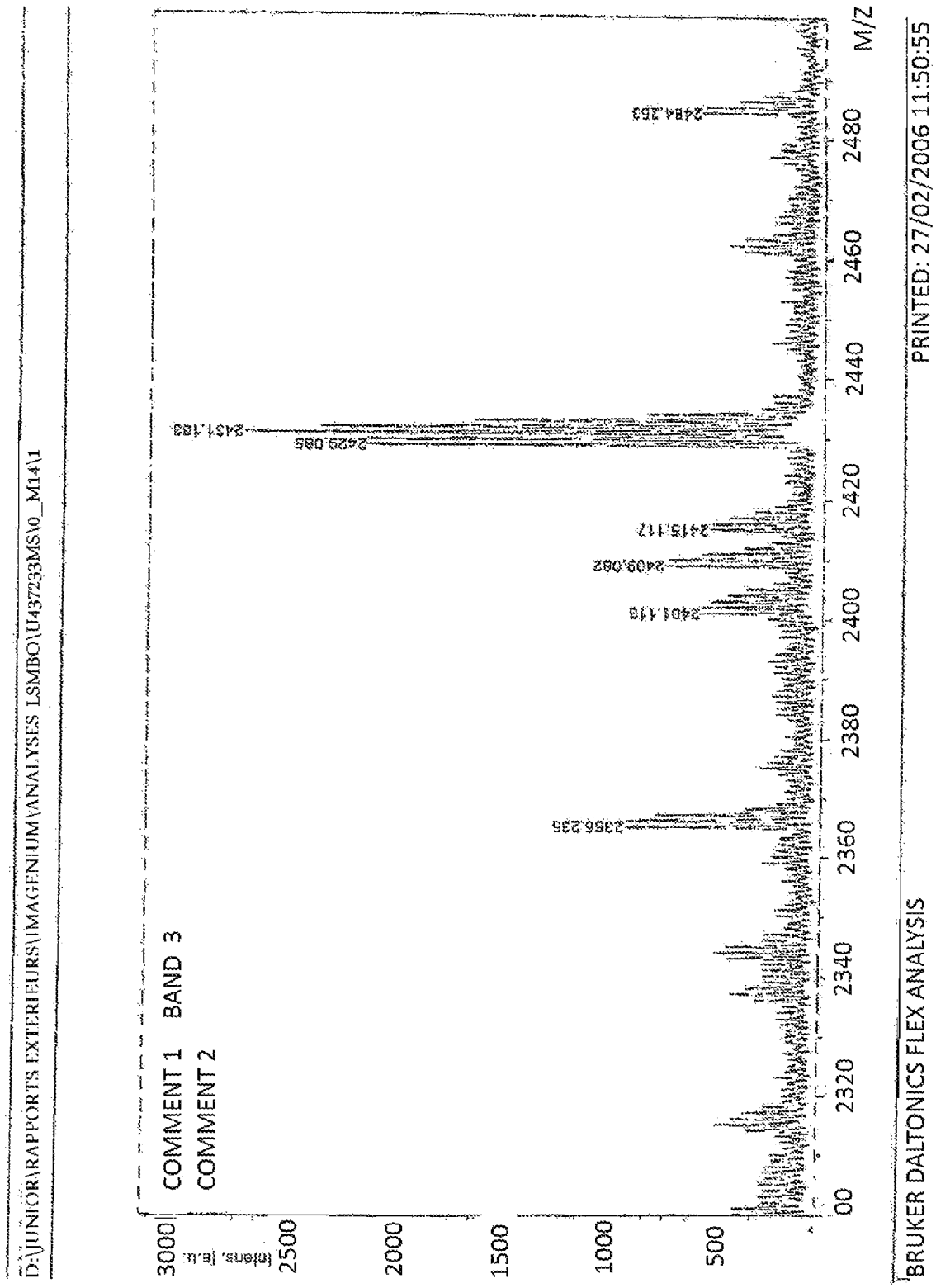
Figure 5:
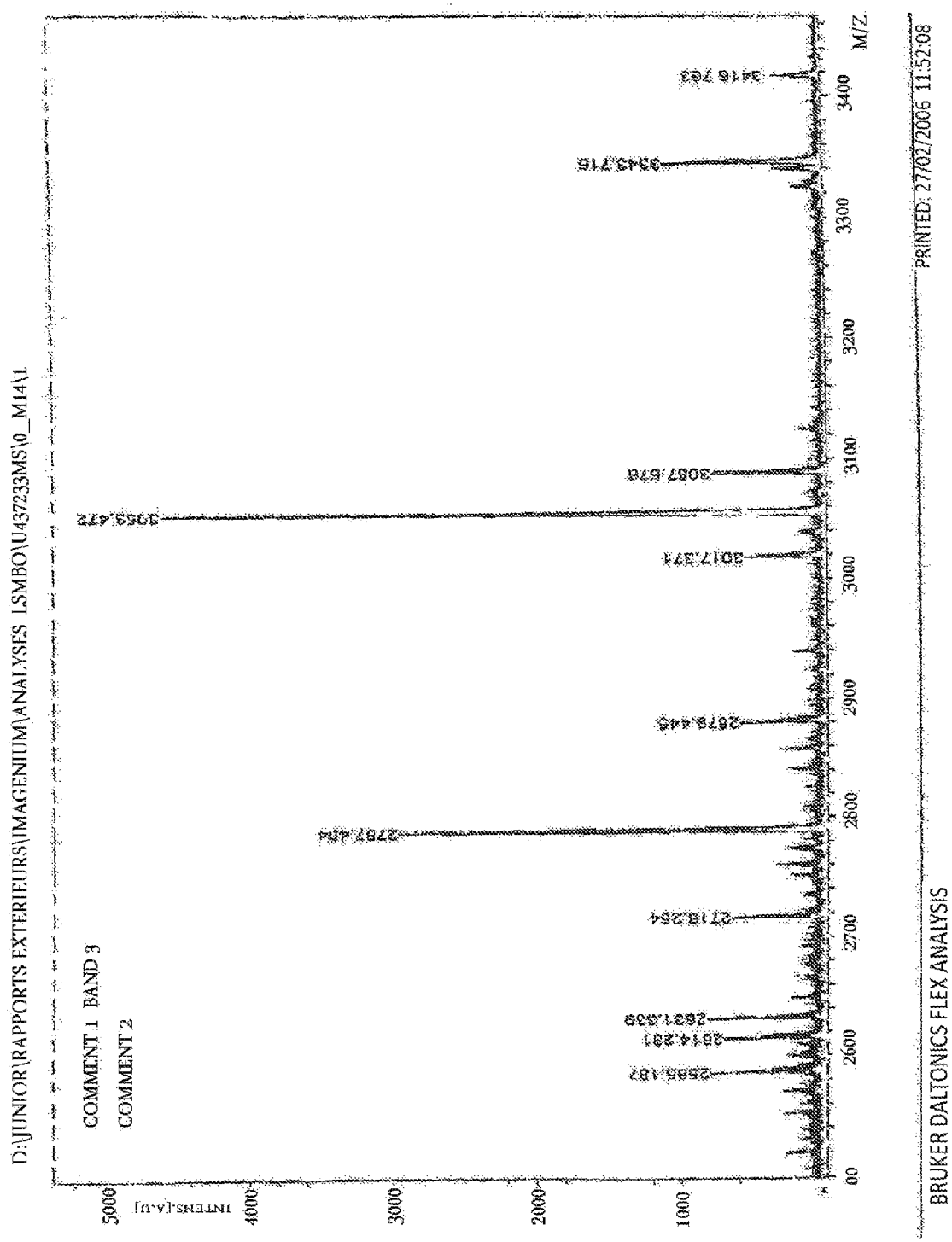

The FIGS. 3-5 describe the MALDI analyses giving a set of polypeptides that can be assigned to the LIV21 protein and its complex.

FIG. 6: analysis on the data banks the listings of monoisotopic peaks. Example of the clathrine CLH22. The Mascot search parameters are: trypsin enzyme, variable modifications: carbamethylation and oxidation of methionins, without molecular mass limit, without isoelectric point restriction.

FIG. 7 idem but the second example:

Type of mass: monoisotopic. Mass error (MS): according to the observer 50 ppm or 100 ppm. Non-cleavage with trypsin: 1 The masses captured are M (H+)/real masses. For spectrogram 1, the cysteins are blocked with iodoacetamide. The possibility of digestion with Promega bovine trypsin may be incomplete with cleavage oversight.

Sequences common with Gallus gallus (gi 50732569), the Mouse Syntaxin, the histatin variant HIS3-2 (P15516-00-01-00), the ZN575-Human, the G6P translocase, the HSP60 chaperonin, the deiminase, ferrodoxin–NADP(+)reductase, pseudomonas polyribonucleotide nucleotidyltransferase, the clathrin, the dehydrolipoamide dehydrogenase.

FIG. 8: RNA pool

Figure 9B:
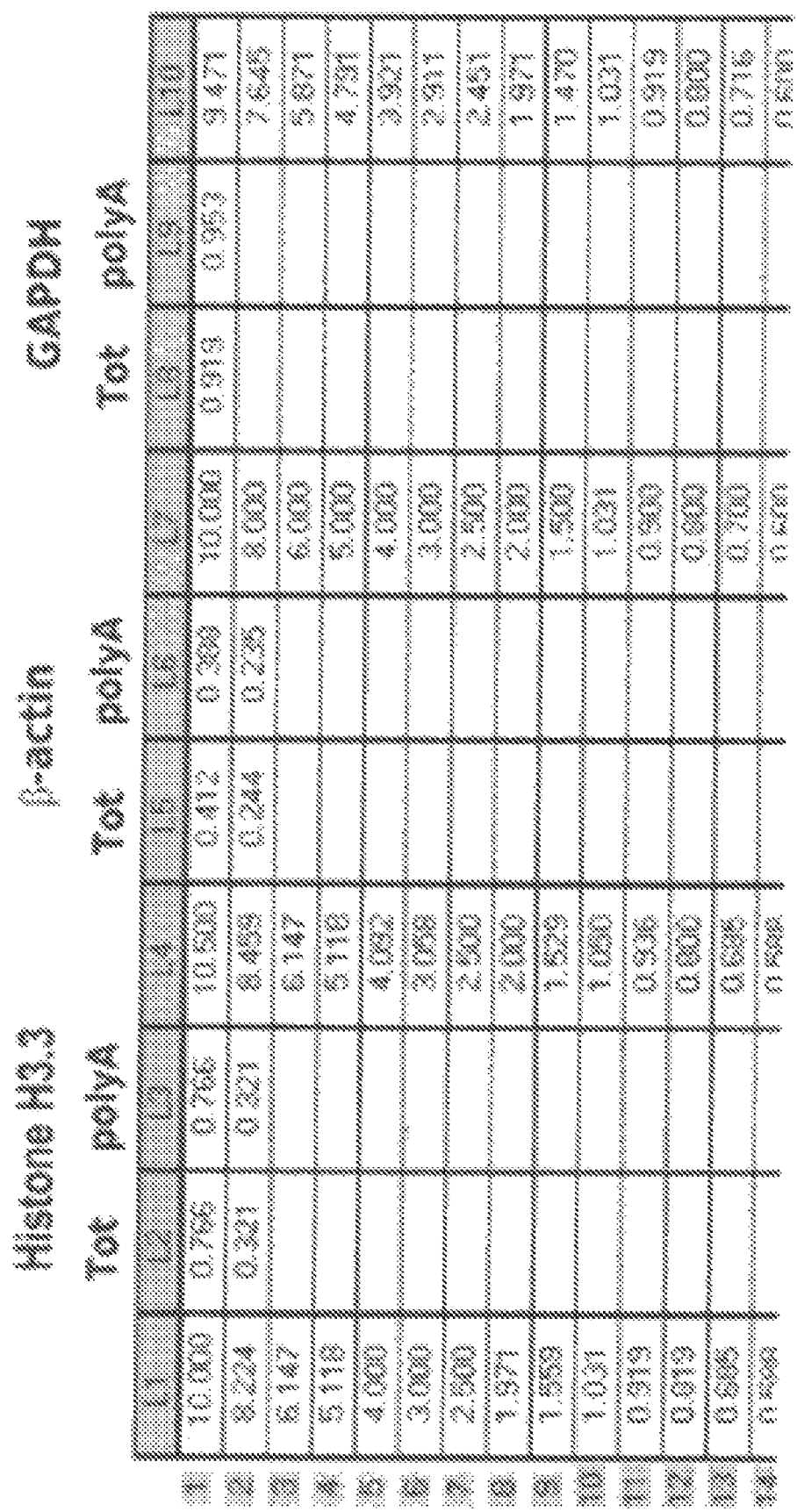

FIG. 9: PCR with housekeeping genes and analysis of molecular masses.

Figure 10:
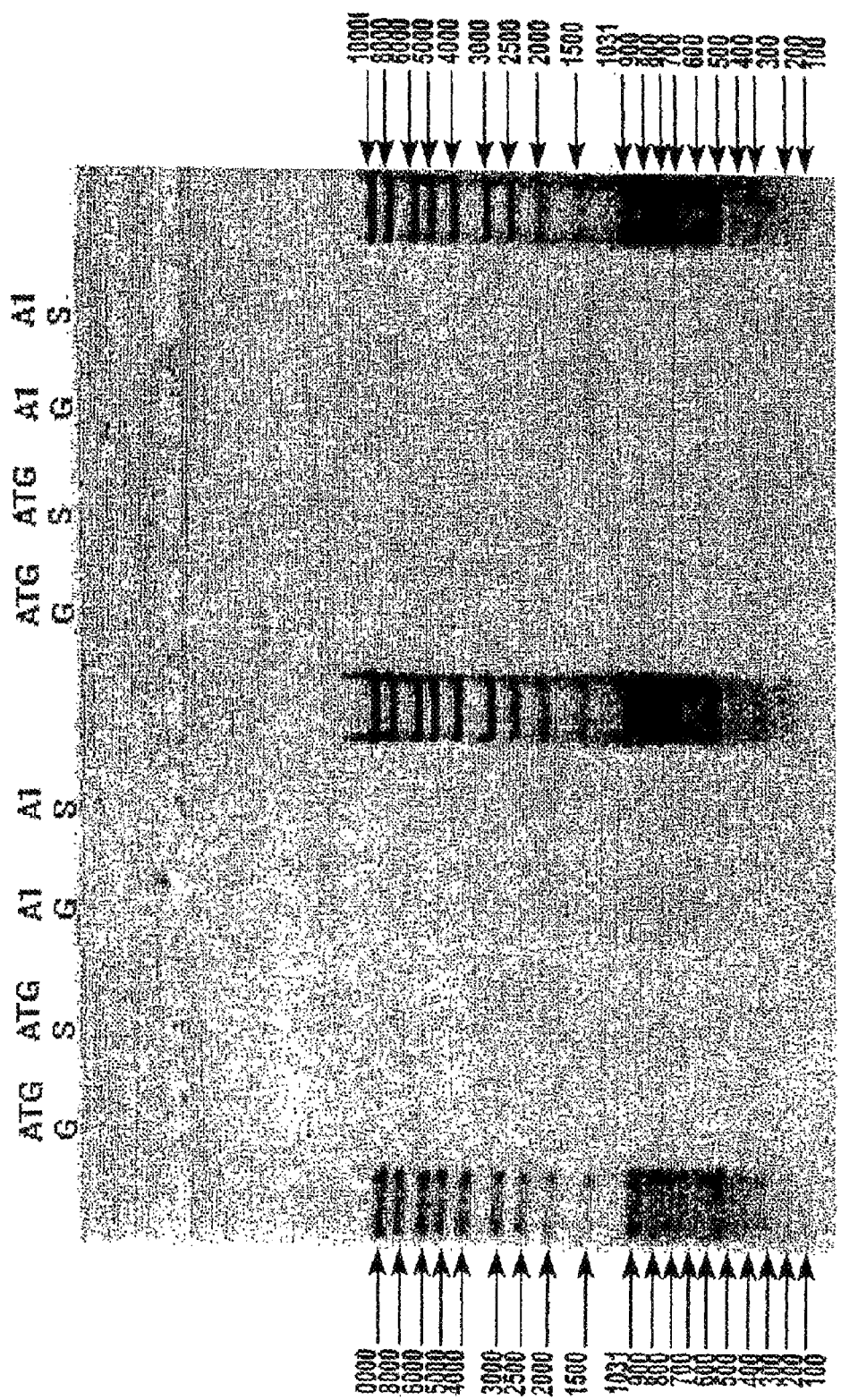

FIG. 10: PCR with the primers showing a band of 1400 bp.

Figure 11:
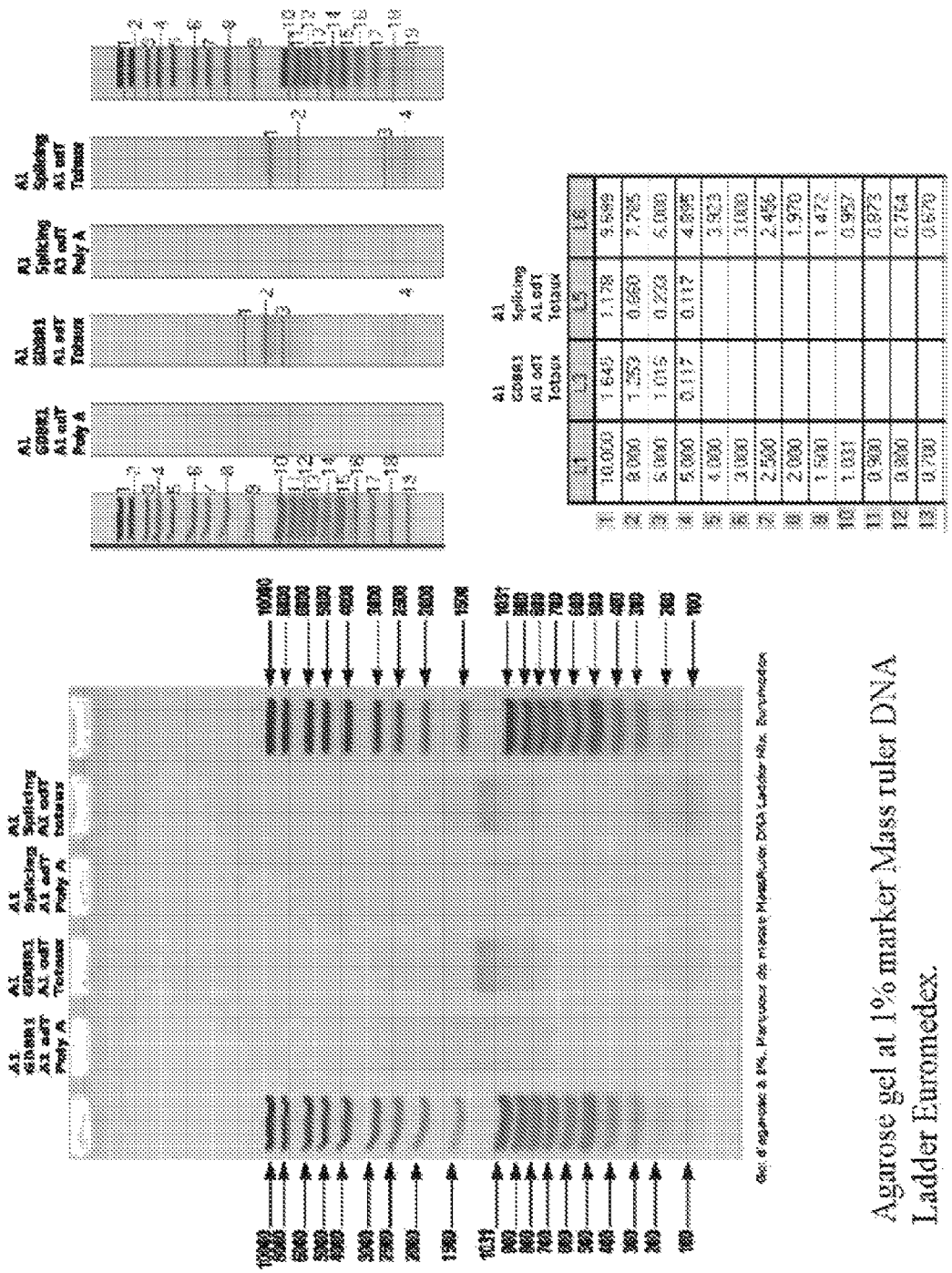

FIG. 11: Gel 2 with analysis of molecular masses

Figure 12:
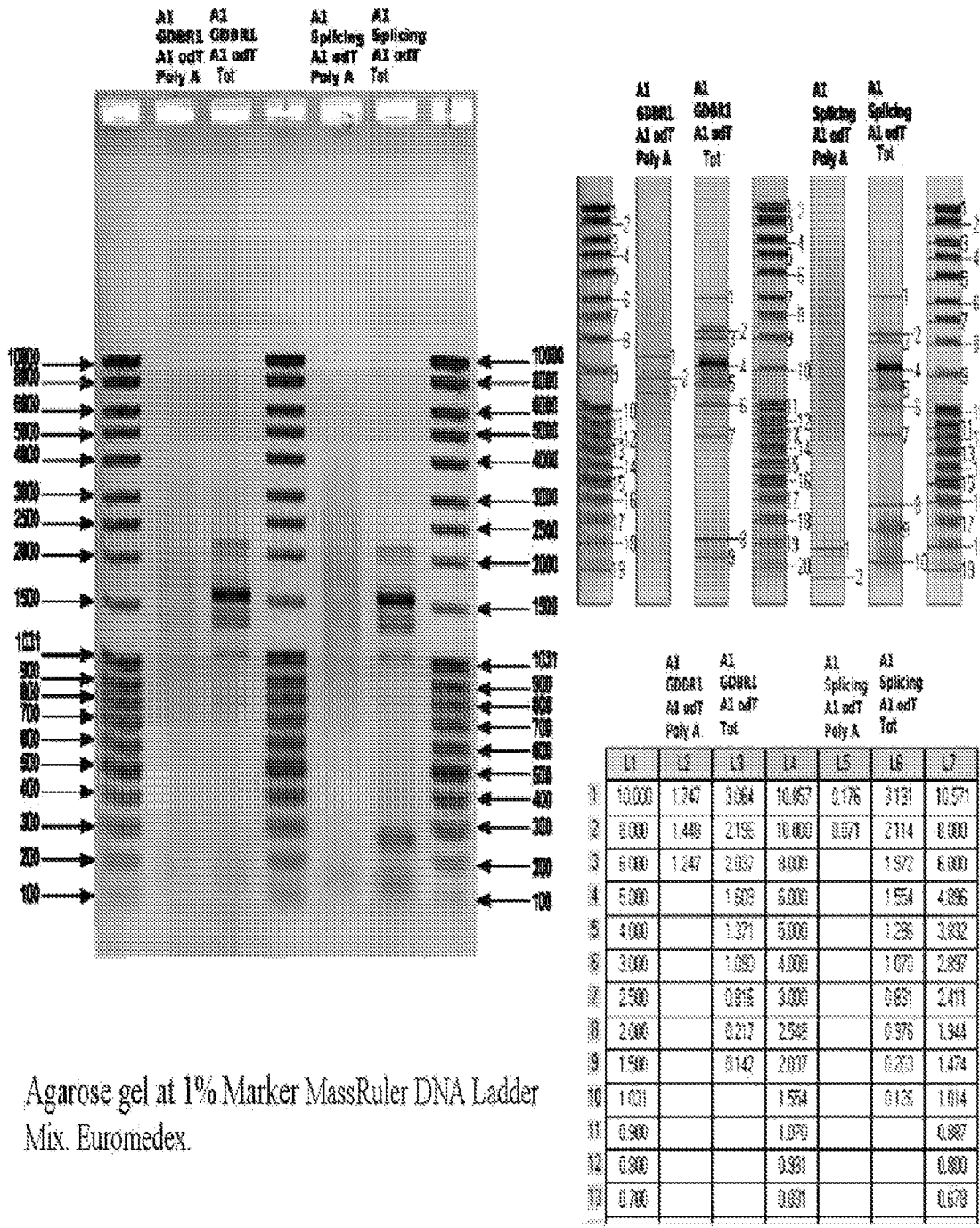

FIG. 12: Gel 3 at 55° and analysis of molecular masses

Figure 13:
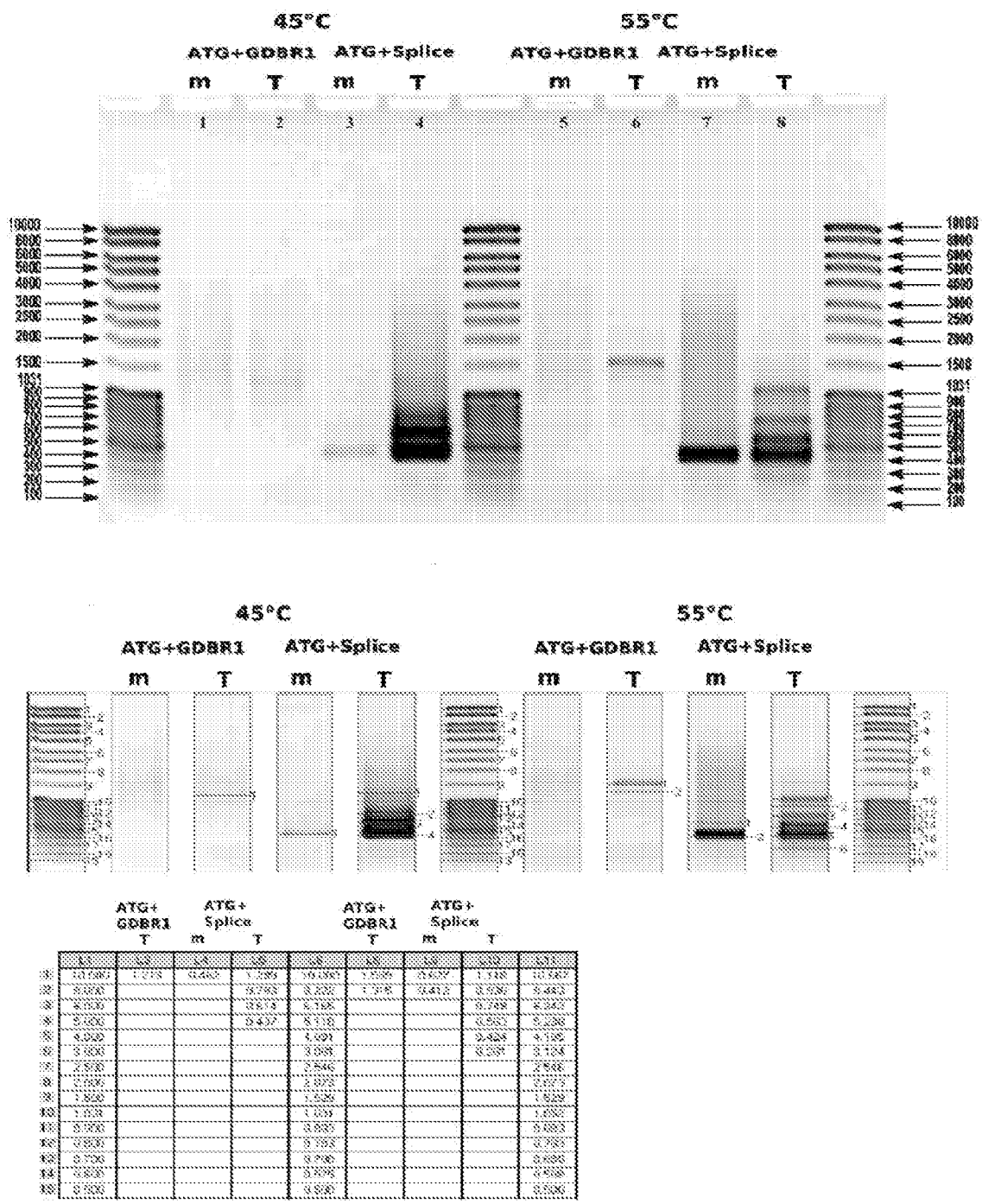

FIG. 13: Gel 4 at 45° and at 55° and analysis of molecular masses.

Figure 14:
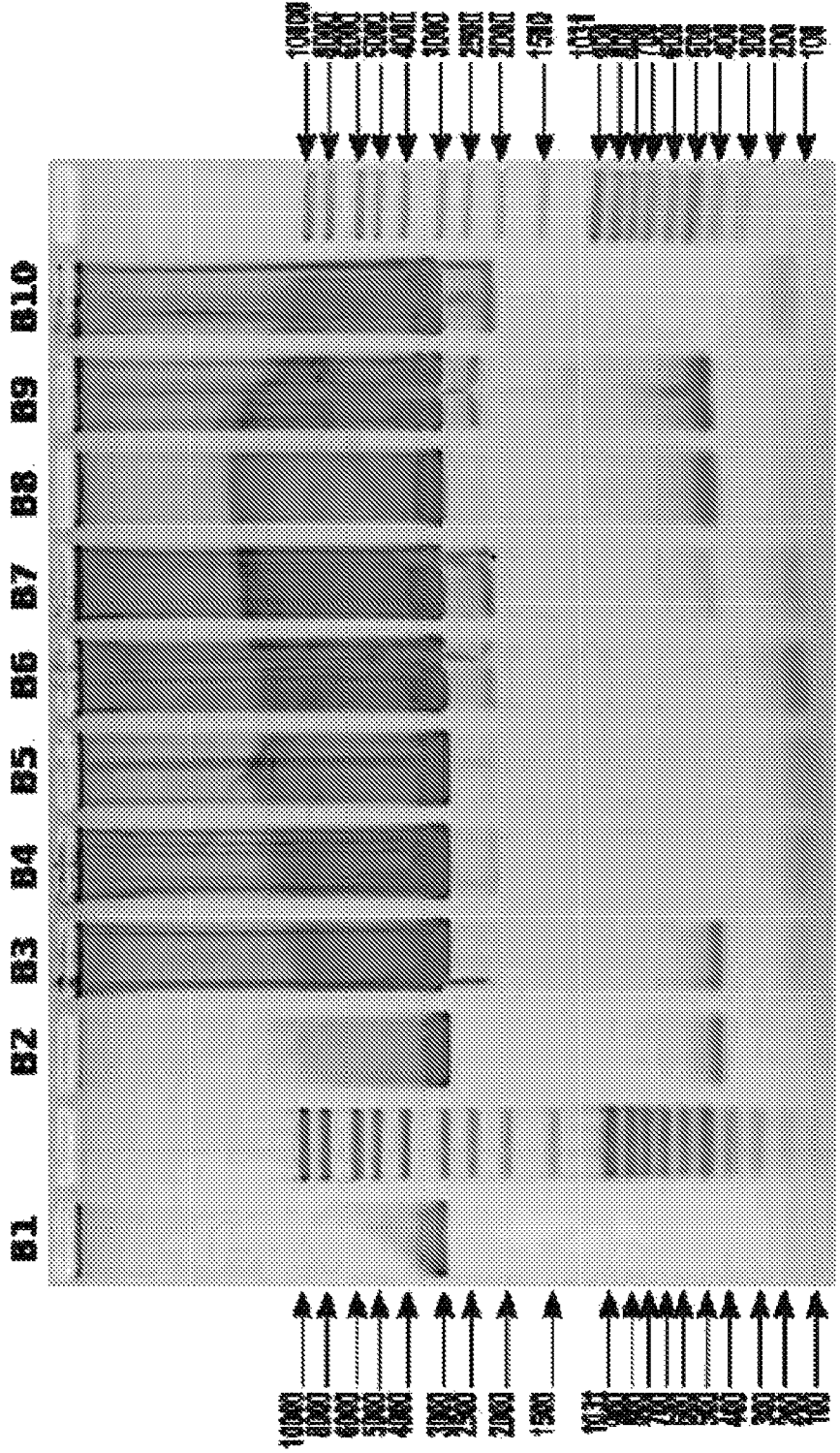

FIG. 14: screening ligation of 400 pb band, clones B1 to B10.

Figure 15:
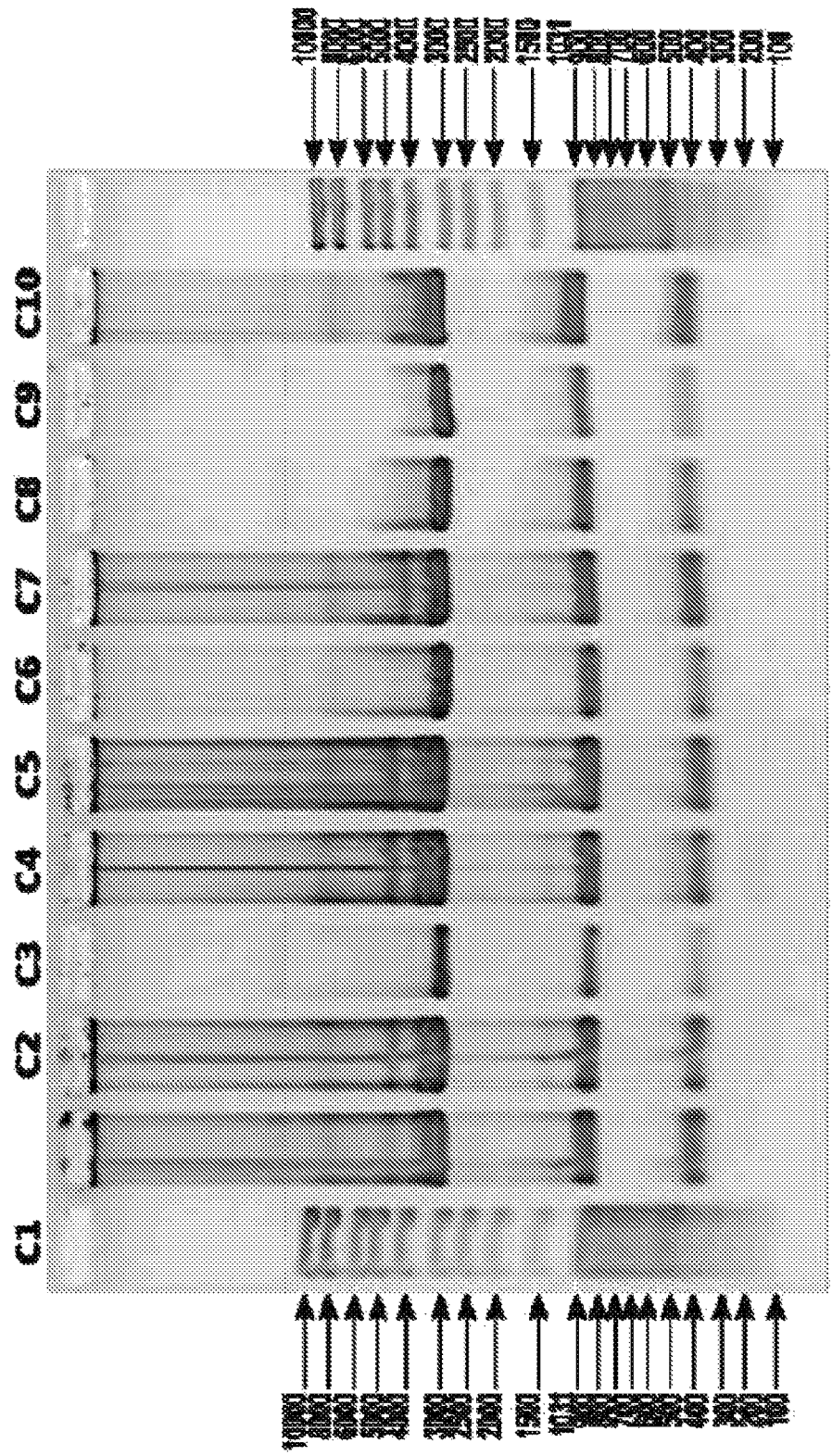

FIG. 15: screening ligation of 1400 pb band, clones C1 to C10.

Figure 16A:
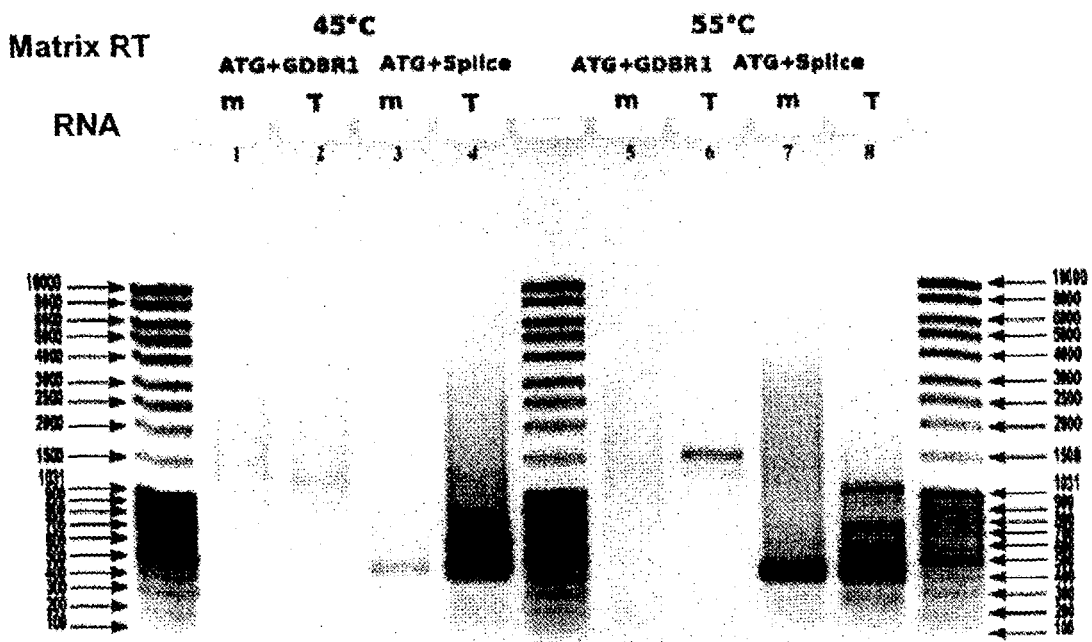
Figure 16B:
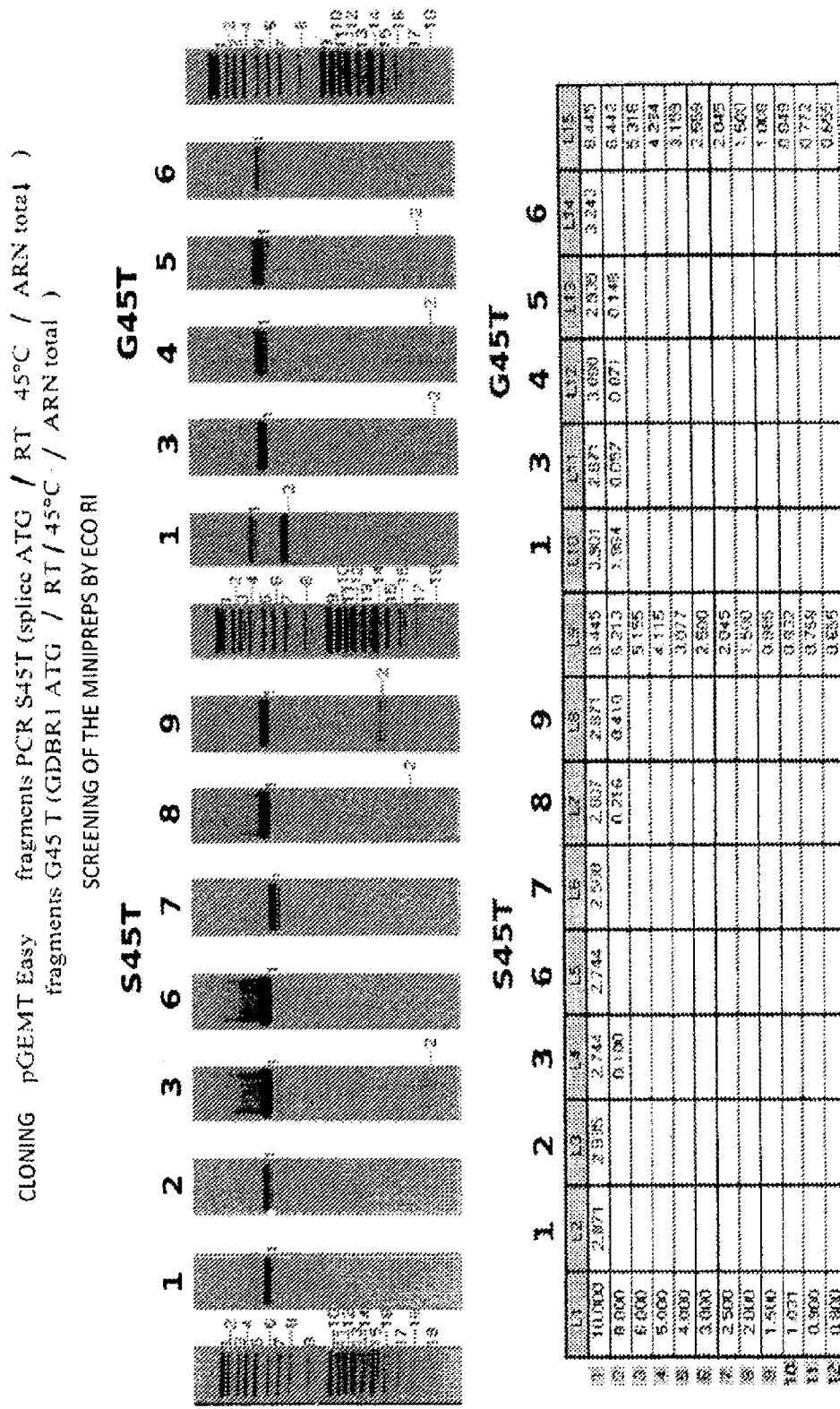

FIG. 16: Gel 5: ligation screening on the five new clones.

FIG. 17: Gel 6: Screening of the S55T and S55M recombinant clones and analysis of molecular masses.

FIG. 18: examples of comparison of nucleotide sequences between the sequenced clones.

FIG. 19: Si RNA design.

Figure 20:
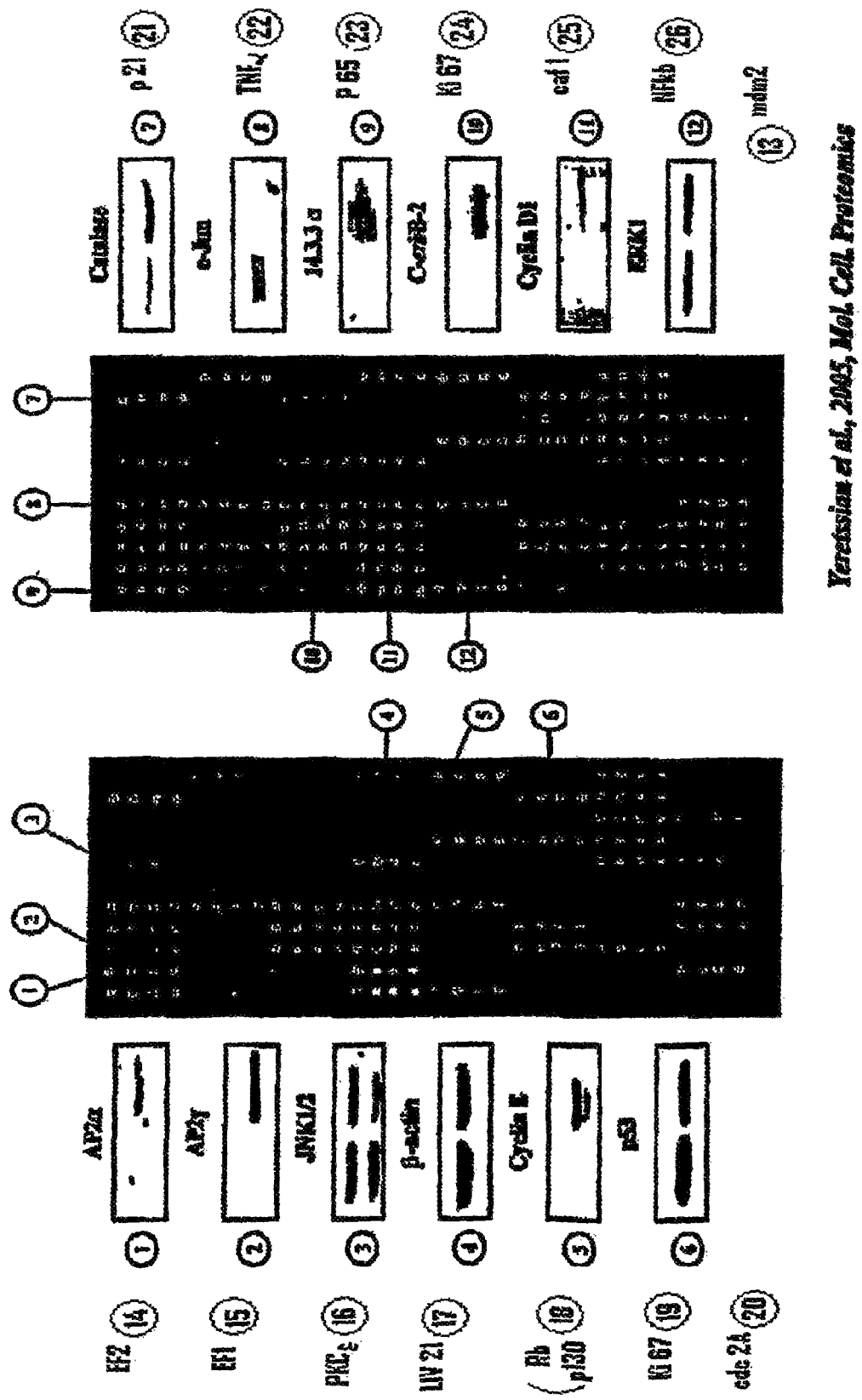

FIG. 20: Protein biochip (array) from Yeretssian but in addition with peptides named of the proteins of the interested complex studied in the invention.

Figure 21:
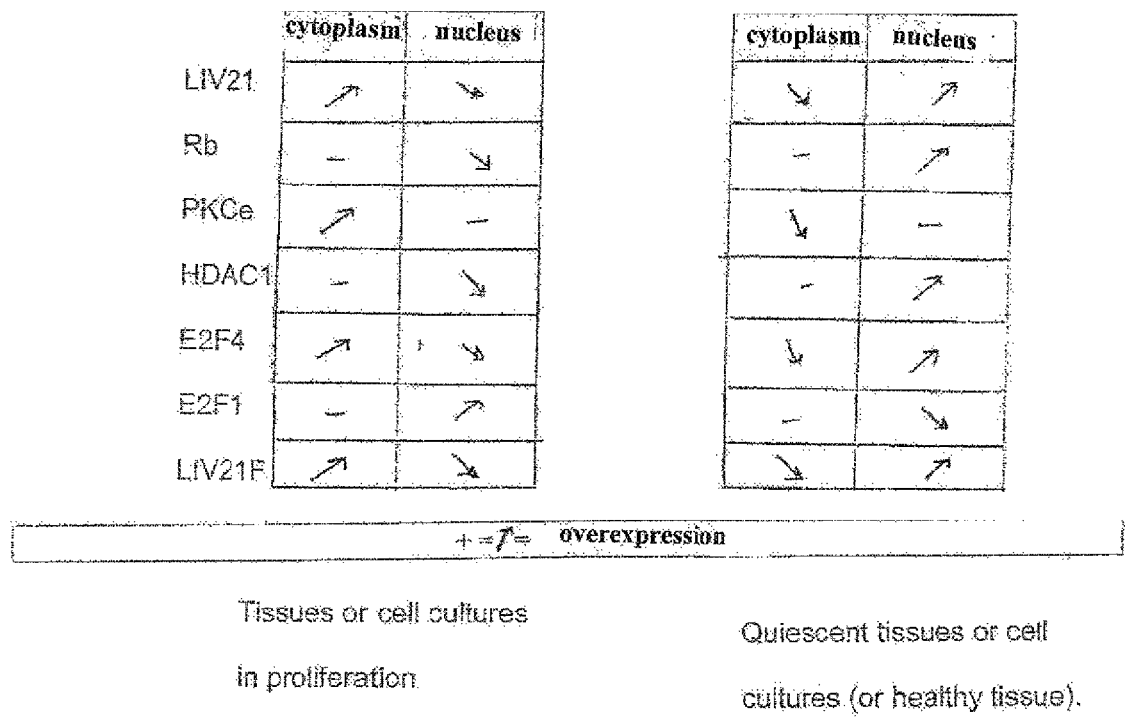

FIG. 21: Biochip of height wells permitting to observe the over or under expression of certain genes of LIV21 complex for example.

FIG. 22: Sequences of the LIV21 complex.

FIG. 23: shows, by immunocytochemistry LIV21. The colabeling (by fluorescent immunolabeling) of LIV21 (green) and of DNA (red with propidium iodide) in the nuclei of the cells, it's red and here a variation of grey LIV21 (green), is cytoplasmic in cells of colon cancer.

FIG. 24 is, a peroxydase immunolabeling of paraffined lames of normal breast tissues on the biopsies of normal tissues and the nuclear LIV21 expression is demonstrated in the biopsies.

DETAILED DESCRIPTION OF THE INVENTION

The invention relates to the identification of antigens in cell lysates by immunoprecipitation. The analysis of the physical interaction of various proteins associated in the LIV21 complex as E2F4 and E2F1 has been studied by coimmunoprecipitation of protein complexes. This analysis has made it possible to demonstrate novel markers, which has a diagnostic and prognostic use for cancer (i.e. PCT/FR2006/000510).

Figure 8:
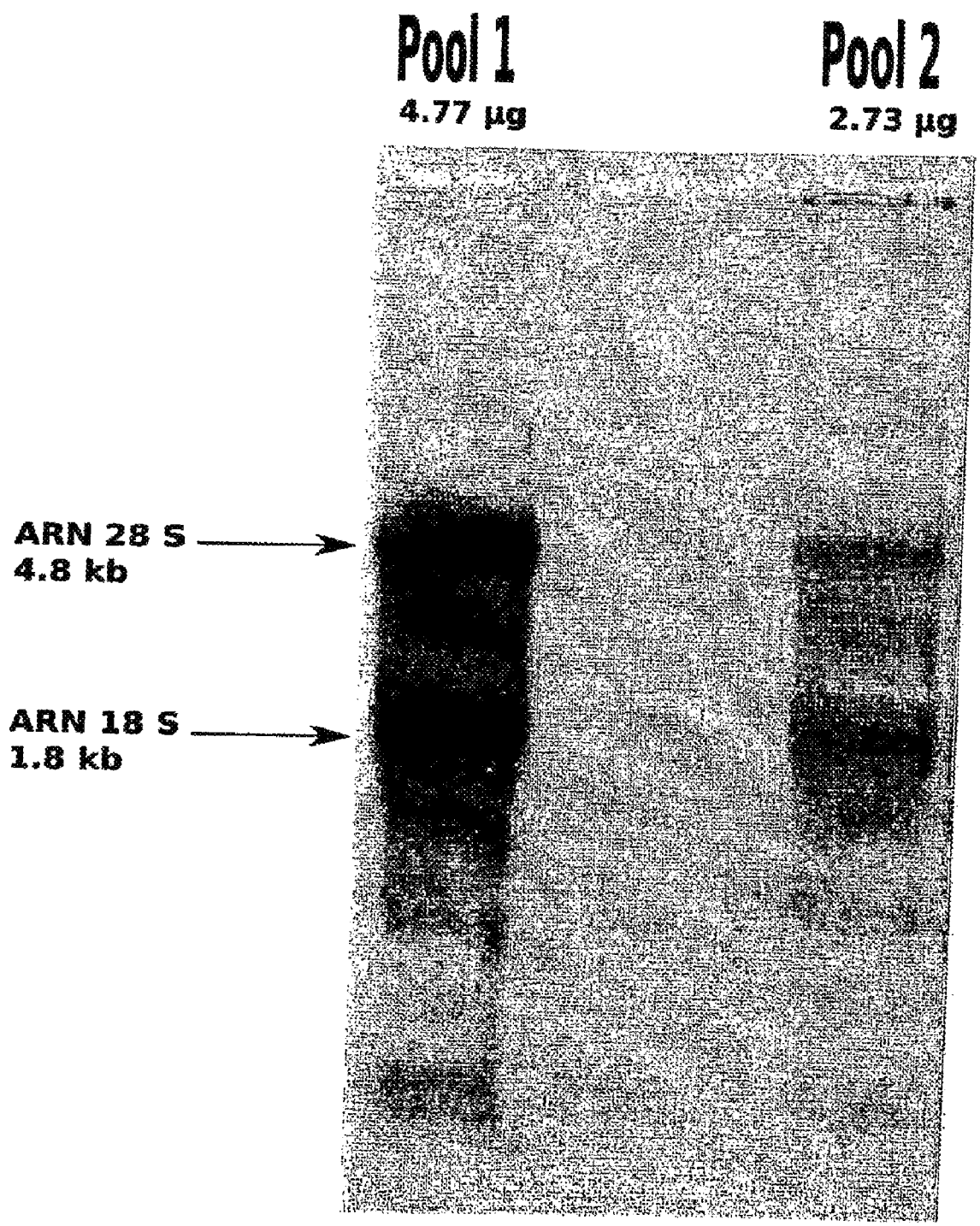

Begin by using the one dimensional and two dimensional gel electrophoresis analysis (FIGS. 1 and 2), the protein samples corresponding to the putative protein and to the elements of the complex were extracted from the gels and digested with trypsin (Promega) in order to be analysed by MALDI (FIGS. 3 to 5) and ESI MS/MS mass spectrometry. The results, when put up against proteomic databanks, made it possible to reveal several peptide sequences of interest, including some given as an example (FIGS. 6 and 7), some being found in humans with very significant scores (splicing of histatin, etc., FIGS. 8 and 9), these sequences were used as primers (once reverse-transcribed to cDNA) for screening a library formed from breast cancer-specific MCF7 cells (FIGS. 10 to 17).

The cloning made it possible to bring to the fore about twenty clones out of the 150 clones obtained, of which ten clones were sequenced and characterize the new LIV21 complex (FIG. 17). Based on these sequences, siRNAs were determined in order to allow regulation of silencing type within this metabolic complex of interest so as to develop therapeutic applications (FIG. 18).

In post-mitotic cells, apoptosis could correspond to an aborted attempt at mitosis. It is in this context that the application of LIV21 has been developed. The inventor has identified sequences of the LIV21 gene. Using the LIV21 antibody on affinity columns he has been able to extract peptides of the LIV21 protein; he has also used a second approach by means of a coimmunoprecipitation kit (Pierce) in order to have larger amounts of proteins (Example 1). Based on peptide sequences of the LIV21 protein, obtained by mass spectrometry (Example 2), primers which make it possible to amplify a cDNA fragment were designed (Example 3). After culturing and amplification of MCF7 line cells, extraction and purification of RNAs, RT PCRs and cloning in a shuttle vector were carried out, and then screening of the resistant colonies and sequencing made it possible to reveal sequences characterizing the genes of the LIV21 complex (Examples 4 and 5). More than twenty characteristic clones out of 150 clones were studied. The cDNA of these clones was used to screen a library prepared from the total mRNA of MCF7 cells. The sequence of this new products are new transcription factors, the nuclear translocation of which change role and function. Furthermore, it forms heterodimers with other transcription factors and certains bind to DNA.

Using Northern blotting, the inventor then followed the expression of this new product during development, from the embryonic stage. It was observed that the amount of the LIV21 protein increases as development progresses, i.e. as a quiescent cell state becomes established. Through the same strategy, the inventor showed that the LIV21/E2F4 complex inhibited the expression of E2F1. This complex could correspond to a new checkpoint in the arrest of cell proliferation.

The discovery of this novel molecule LIV21 could have a diagnostic value for the following reasons. By carrying out a screening of the localization of LIV21 in about ten human tumors, the inventor has been able to observe that, in all proliferating tumor cells, this protein is cytoplasmic instead of nuclear with Liv21 antibody (example 8). It is not therefore in the correct cellular compartment to be active on the arrest of cell multiplication.

It has thus been possible to observe the presence of LIV21 in mammals. The panel of LIV21 expression as a function of cell state (mitotic cycles, cell in the resting state, differentiation) has been studied on tissues originating from various mammals. Protein analyses on the various tissue samples have confirmed that the expression of this transcription factor appears to be associated with a progression toward a quiescent cell state (arrest of mitoses and entry into differentiation). LIV21 is present in actively proliferating tumor cell lines and its expression is essentially cytoplasmic. The same results are obtained on human mammary adenocarcinomas (example 9).

Thus, the present invention relates to a novel test for screening for anomalies of the reinduction of the cell cycle. Pharmacodiagnostic test is based on the study of the mechanism of action of the novel gene, encoding a potential novel transcription factor called LIV21, which down-regulates proliferation. LIV21 is implicated in the arrest of cell proliferation. The isolated cDNA fragment encodes for a protein containing a leucine zipper motif, a basic domains characteristic of DNA binding domains, and a nuclearization sequence, similar to the nuclear receptor binding factor OR11H6, cd53 antigen with the 400 bp fragment. For example, we note that LIV21 is cytoplasmic when the cells proliferate, whereas it becomes nuclear when the cells become quiescent. The characterization of this factor suggests a new pathway for down-regulating cell proliferation, by virtue of its association with one of the members of the EF family: E2F4. The latter is known to negatively regulate the cell cycle by association with the P130 protein or pocket protein of the RB family.

The localization observed for LIV21 in tumor cells (cytoplasmic localization) and in physiological cells (nuclear localization) suggests, in any event, that its function is disturbed when cell development becomes anarchical.

The characterization of this molecule and the study of the timing and the topology of its expression also indicate that the expression and the localization of this ubiquitous transcription factor are regulated as a function of cell state: greater expression and nuclear localization for cells which have exited mitotic cycles, weak expression and cytoplasmic localization for actively proliferating cells such as human tumor cells.

LIV21 appears to be a key molecule for stabilizing another transcription factor (E2F4) in the cell nucleus and thus for inducing an arrest of cell proliferation.

Furthermore, it has been shown that the localization of LIV21 in the cytoplasmic compartment is regulated by PKCε. In fact, when LIV21 is phosphorylated by PKCε, LIV21 is located in the cytoplasmic compartment. Conversely, when the phosphorylation of LIV21 by PKCε is inhibited, LIV21 is located in the nuclear compartment.

By studying exhaustively metabolic complexes including LIV21, E2F4, HDAC and PKC epsilon, and in some populations and for some cancers, the role of viral sequences, the inventor designed adapted pharmacodiagnostic biochips with a novel choice of transcription factor and peptides from different complexes. This set of biomolecules is specific to the invention, as well as their corresponding polynucleotides. This specific set of proteins or genes involved in the metabolic equilibrium according to their expression level and affecting cell proliferation constitutes the interest of the fabrication of pharmacodiagnostic biochips suited to any type of cancer independent of the technique of support and the protein/protein or protein/gene or protein/antibody interaction used. LIV21

The present invention therefore concerns the LIV21 complex and its nucleotide sequences which can also be used as siRNA for therapeutical applications and also the Liv21 protein and derivatives and fragments thereof.

The LIV21 protein is a protein which depending on the alternative splicing that it undergoes, it exists as at least three forms of different sizes (FIG. 7). Moreover, it can be phosphorylated or sumoylated. It has an apparent molecular weight of between 50 kD and 51 kD in Western blotting analysis.

It can be found as a dimer of a molecular weight higher that 100 kDa.

Figure 1A:
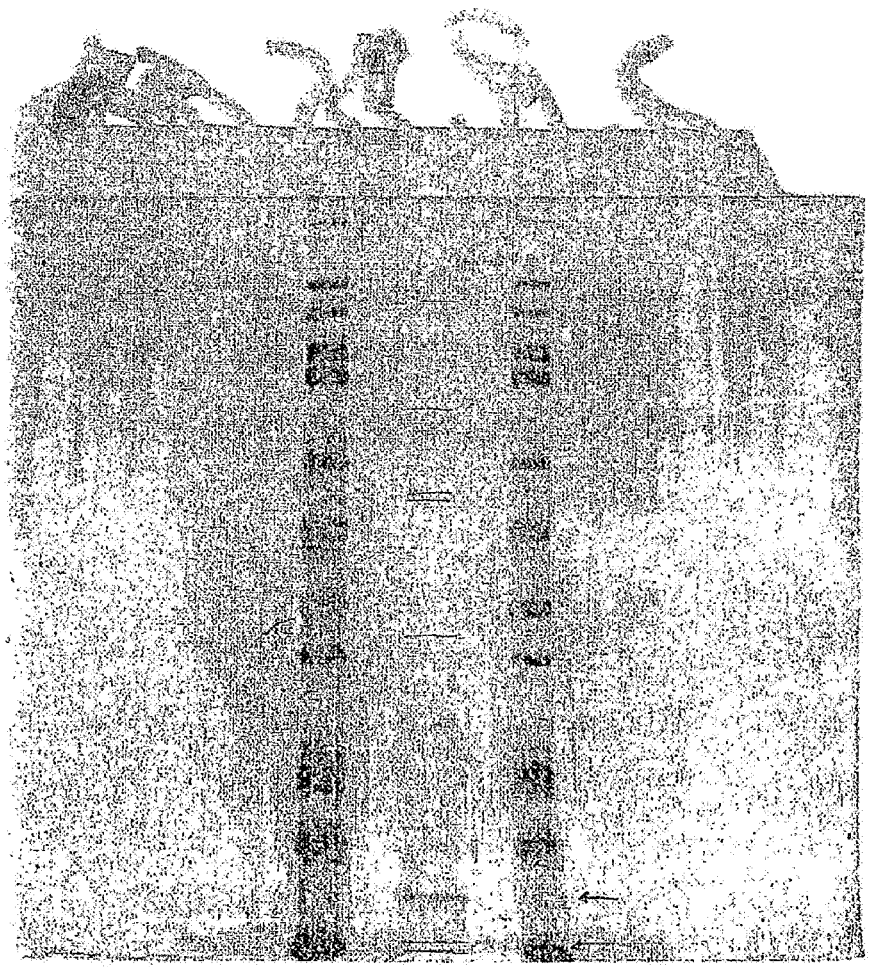
FIG. 1A: one-dimensional gel (acrylamide gradient) and bidimensional SDS Page characterizing the Liv21 complex.
Figure 2:
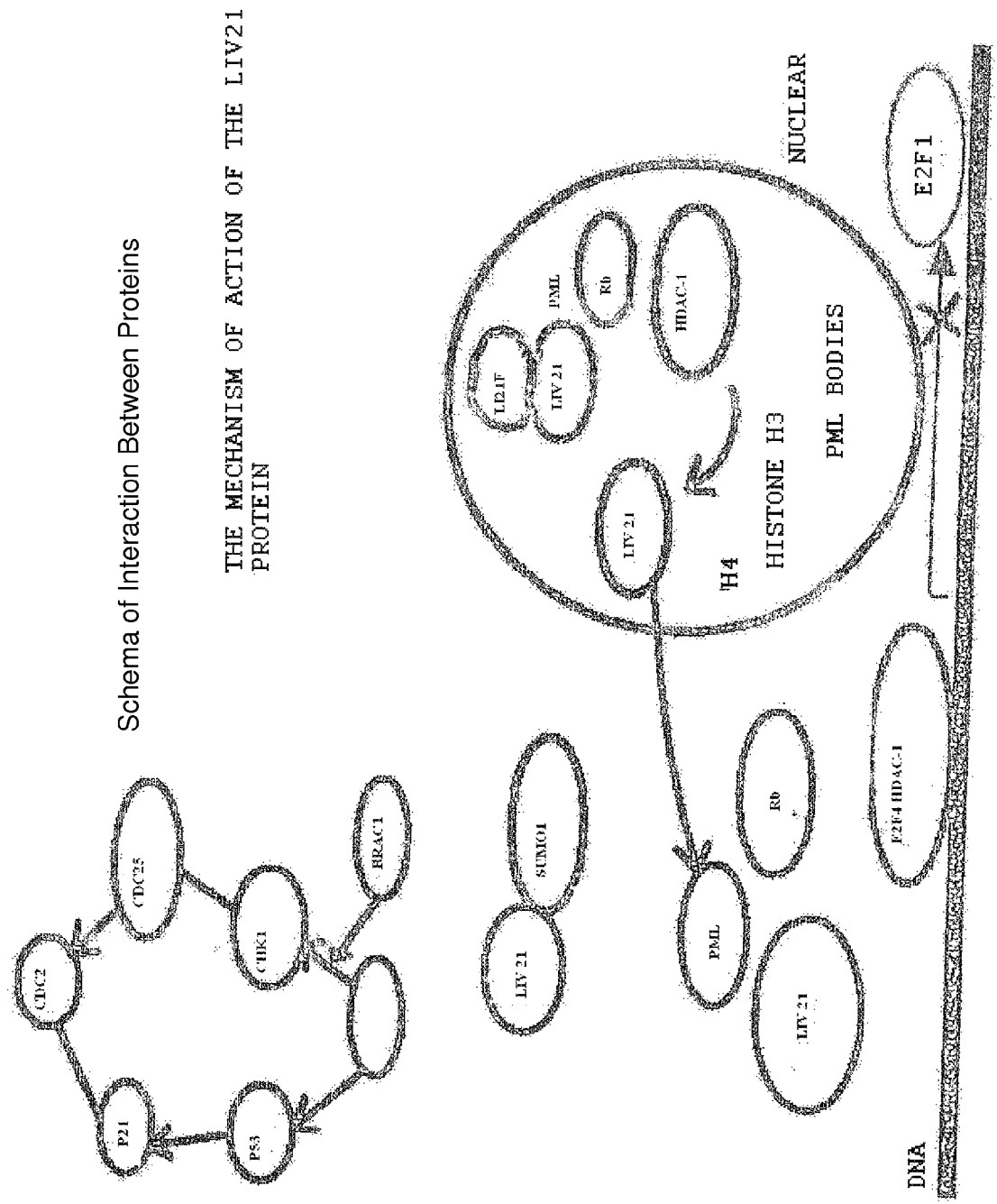
FIG. 2: scheme of nuclear and cytoplasmic protein interactions of the LIV21 complex and consequences on the study of the therapeutic.
Figure 3B:
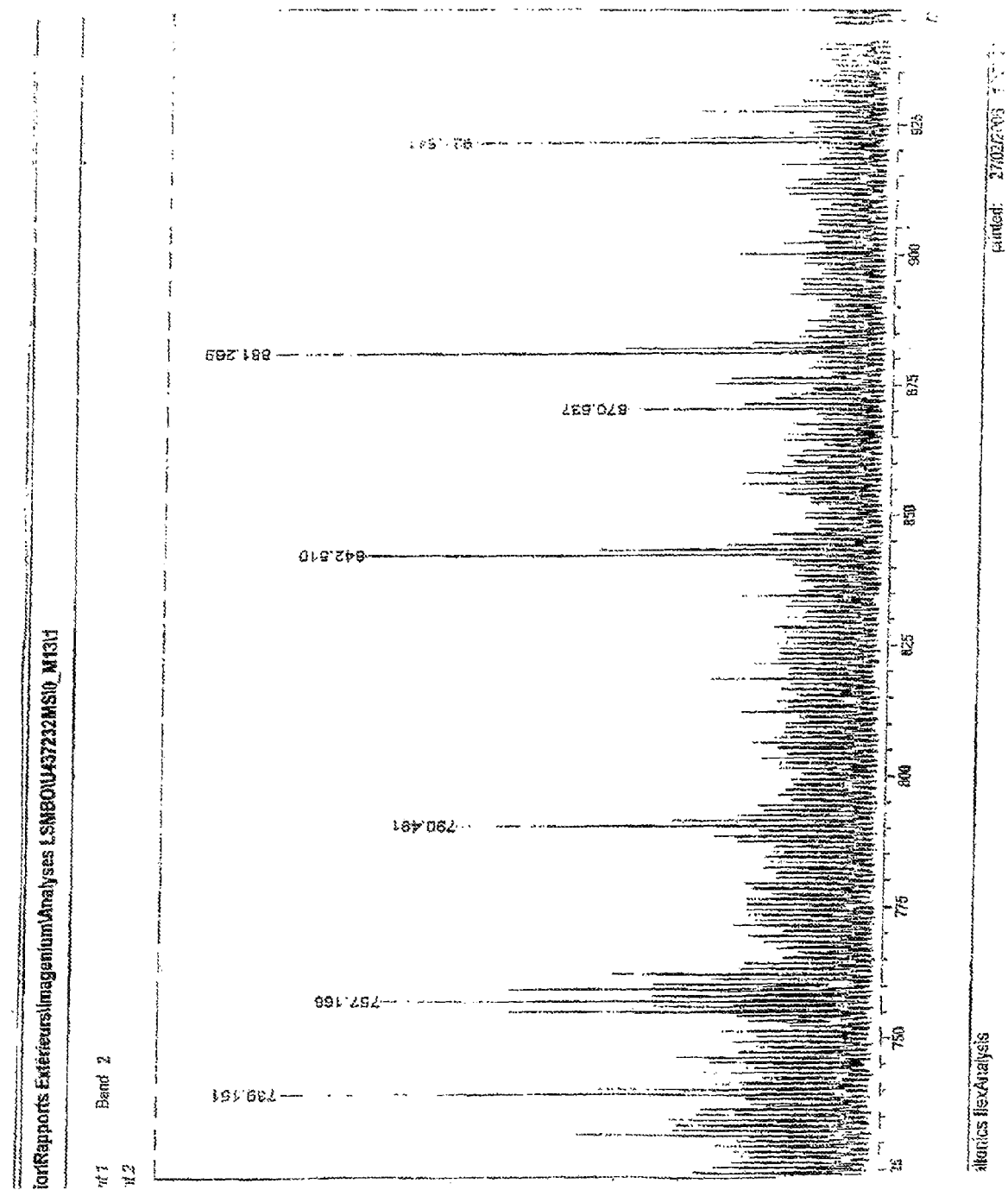
FIG. 3B: LIV21 protein profile by mass spectrometry (Maldi) M (H+) for the one-dimensional gel band corresponding to the band 2 migrating at 49-50 kD. The peptides derived from the digestion are solubilized in a solvent: acetonitrile/water (1/1) containing 0.1% of TFA (trifluoroacetic acid). A saturated solution of the alpha-cyano-4-hydroxycinnamic acid matrix is prepared in the same solvent. The same volume of the two solutions is taken and mixed together, and 1 microliter is deposited onto the Maldi plate for analysis.
Figure 3B:
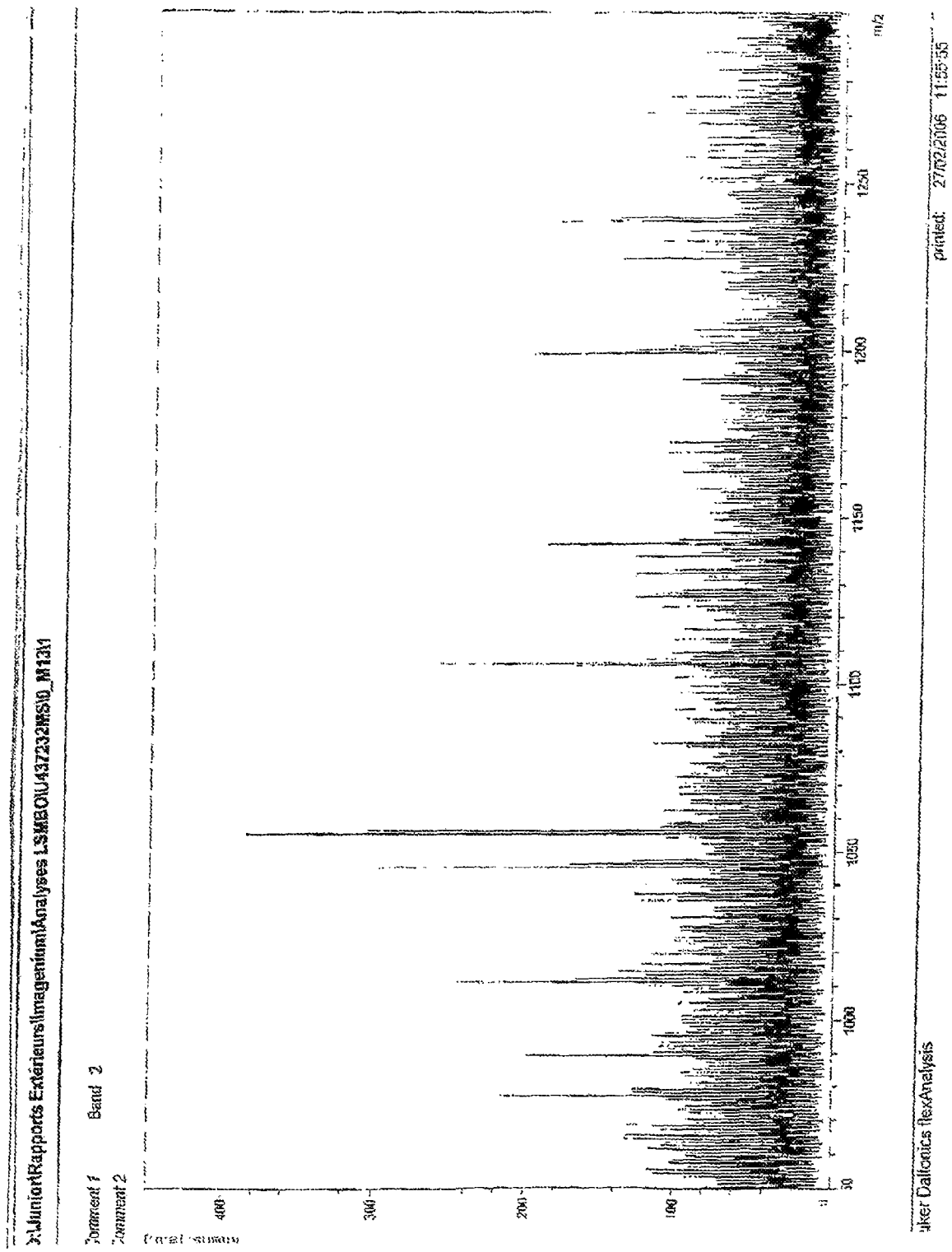
Figure 3B:
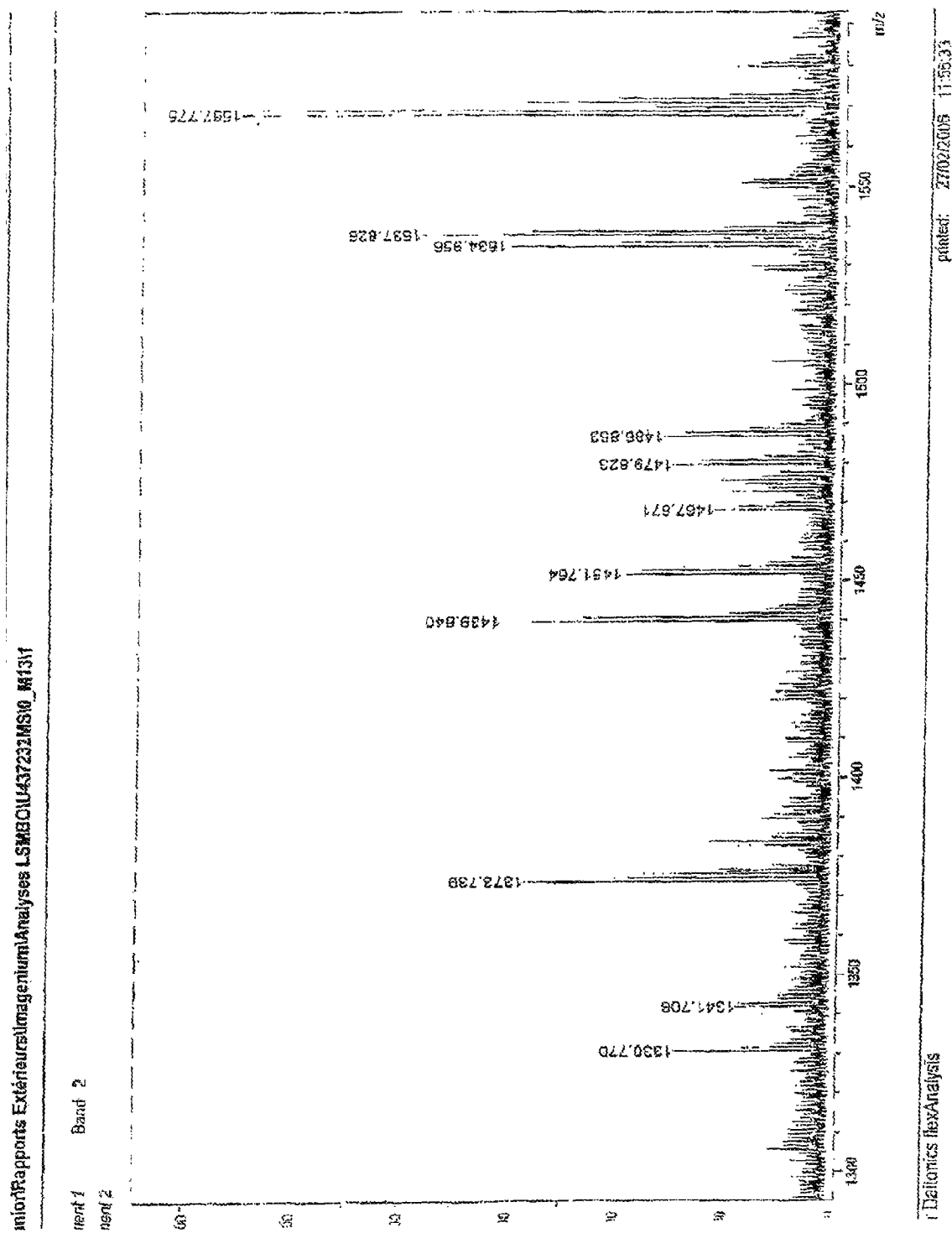
Figure 3B:
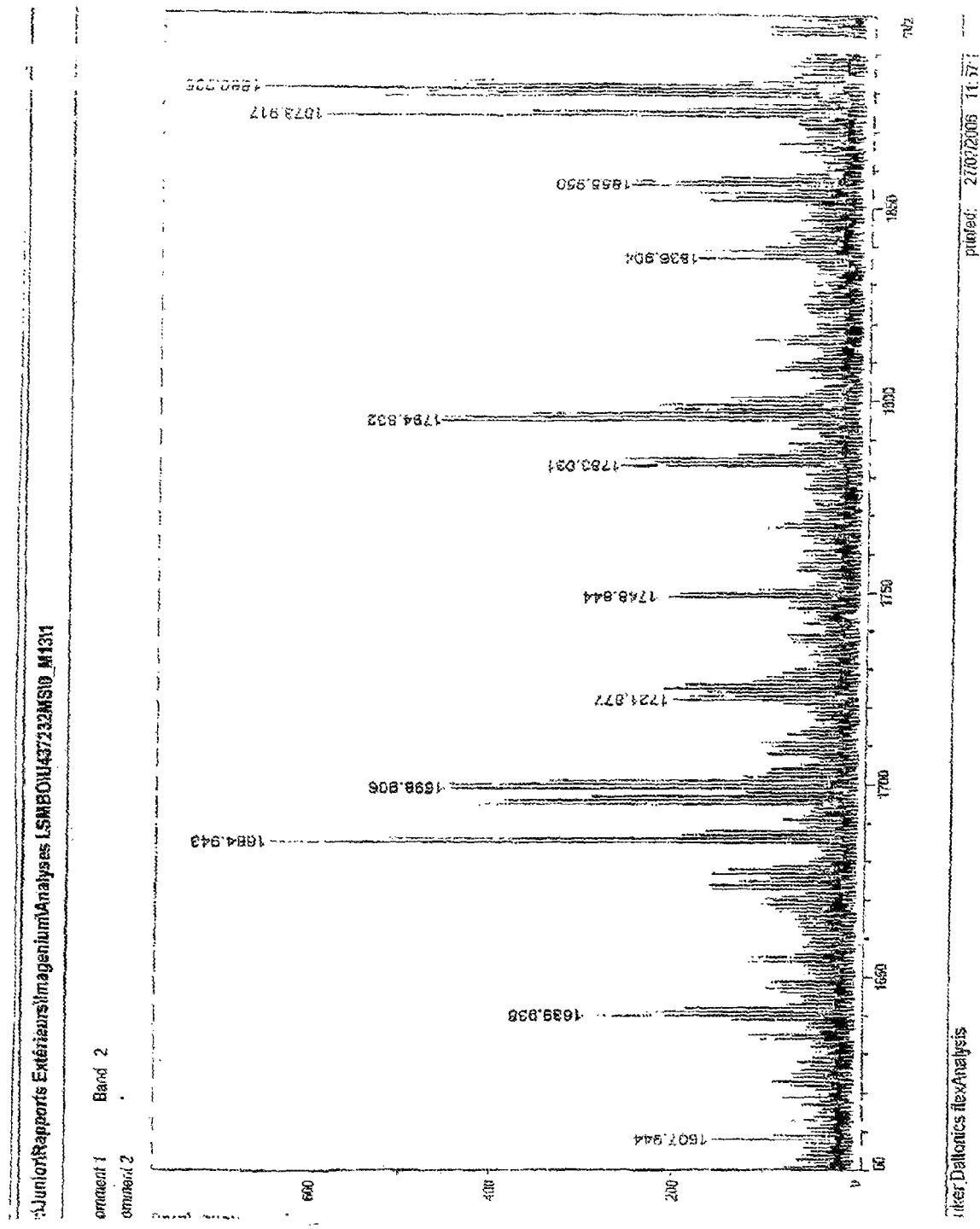
Figure 3B:
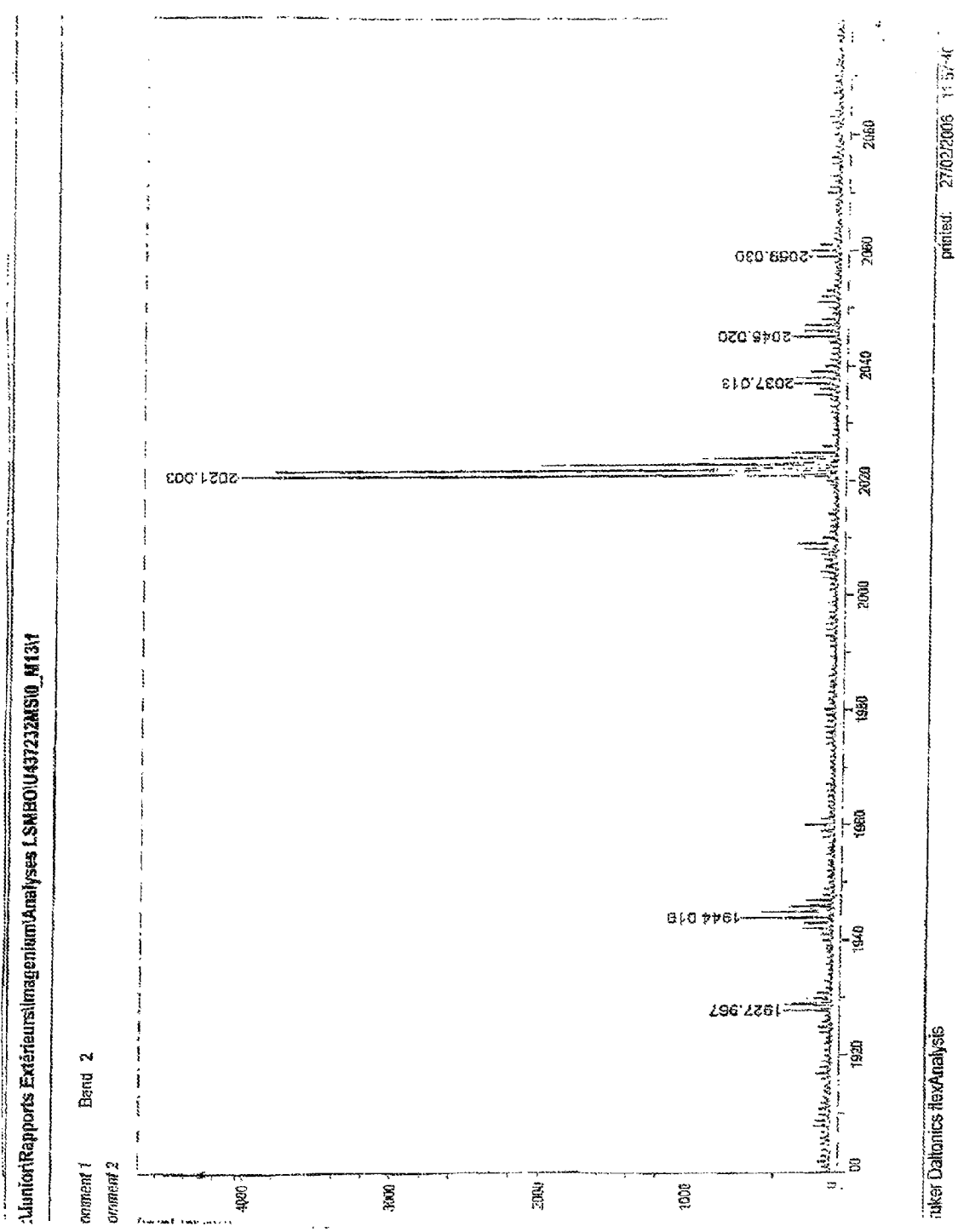
Figure 3B:
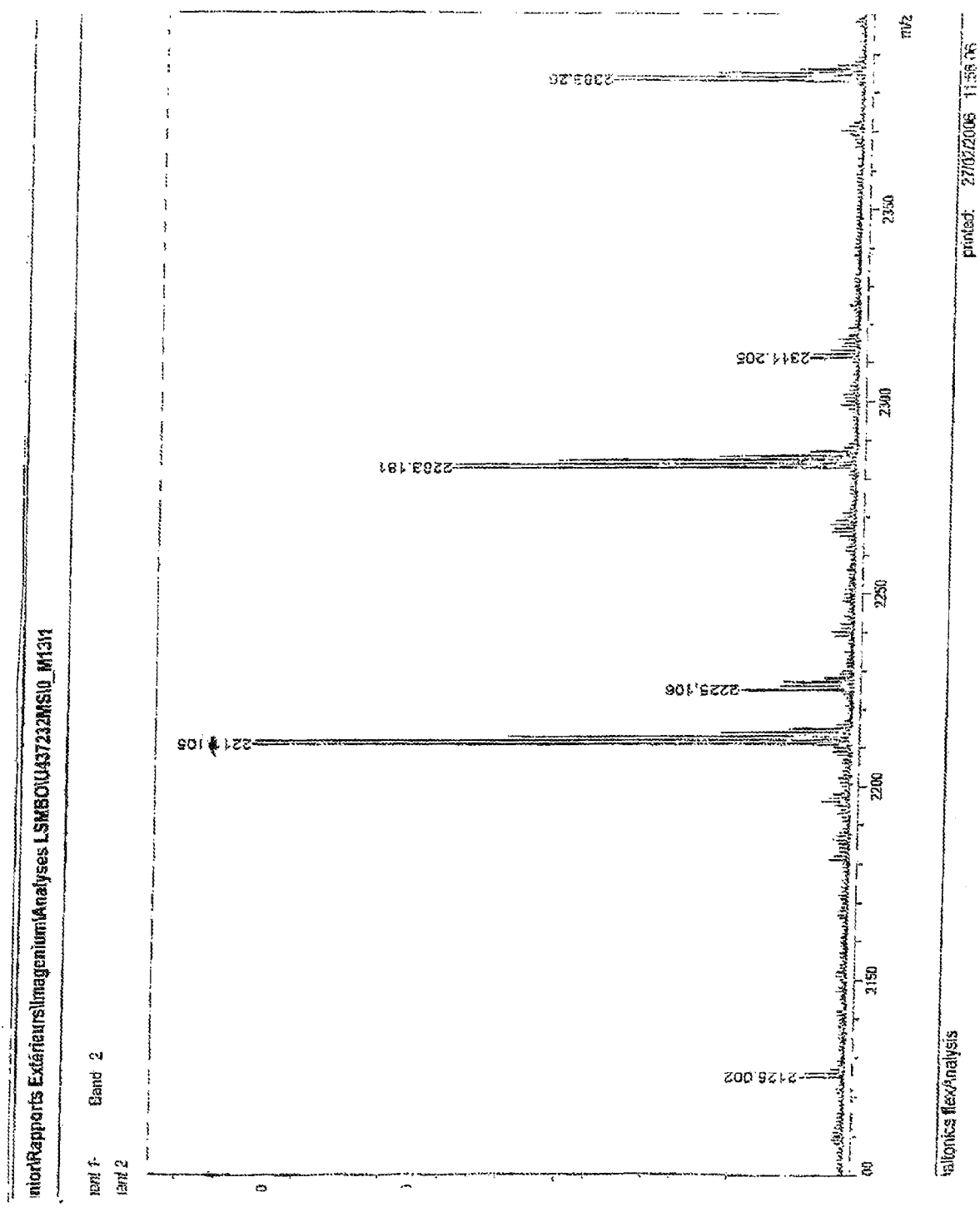
Figure 3B:
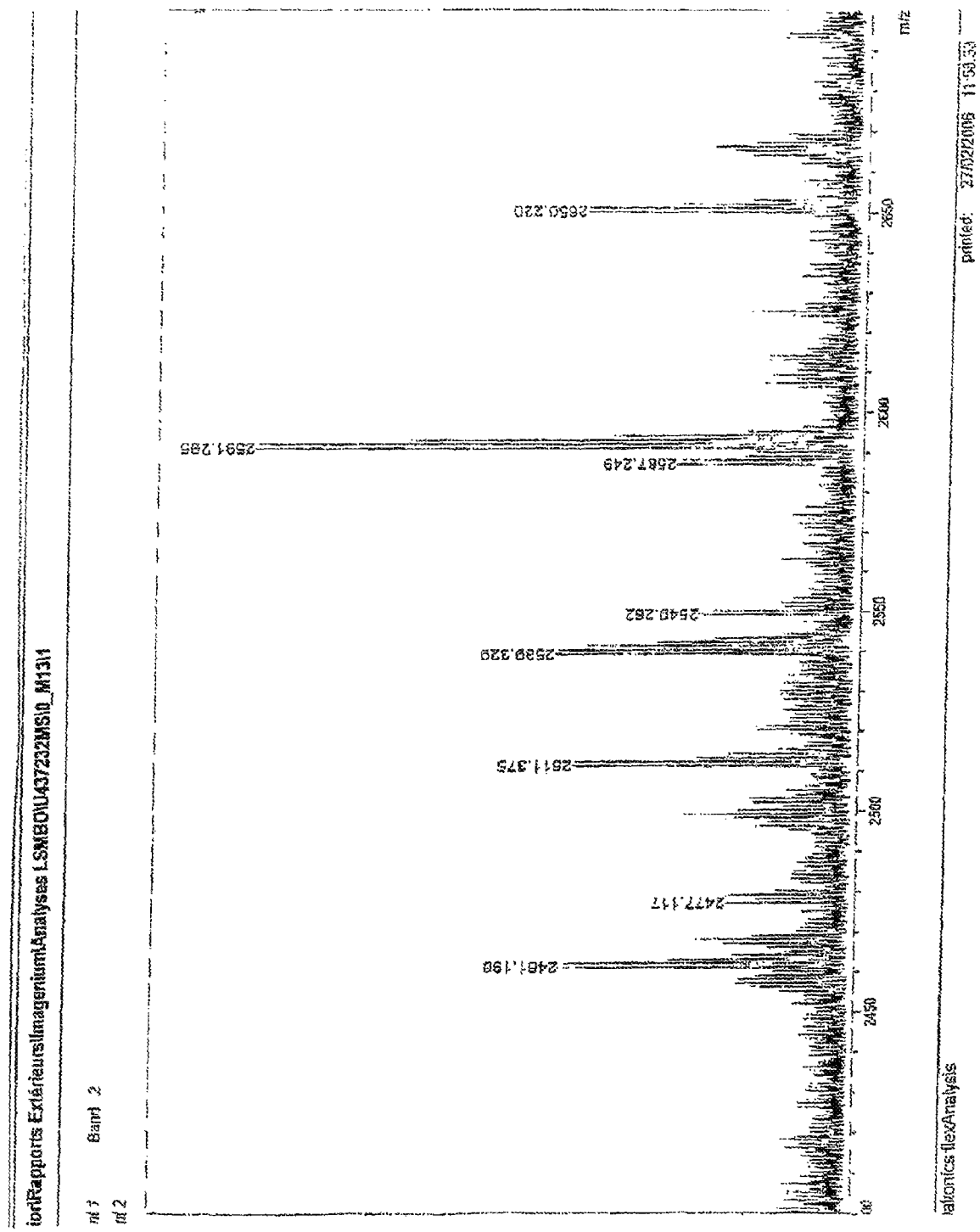
Figure 3B:
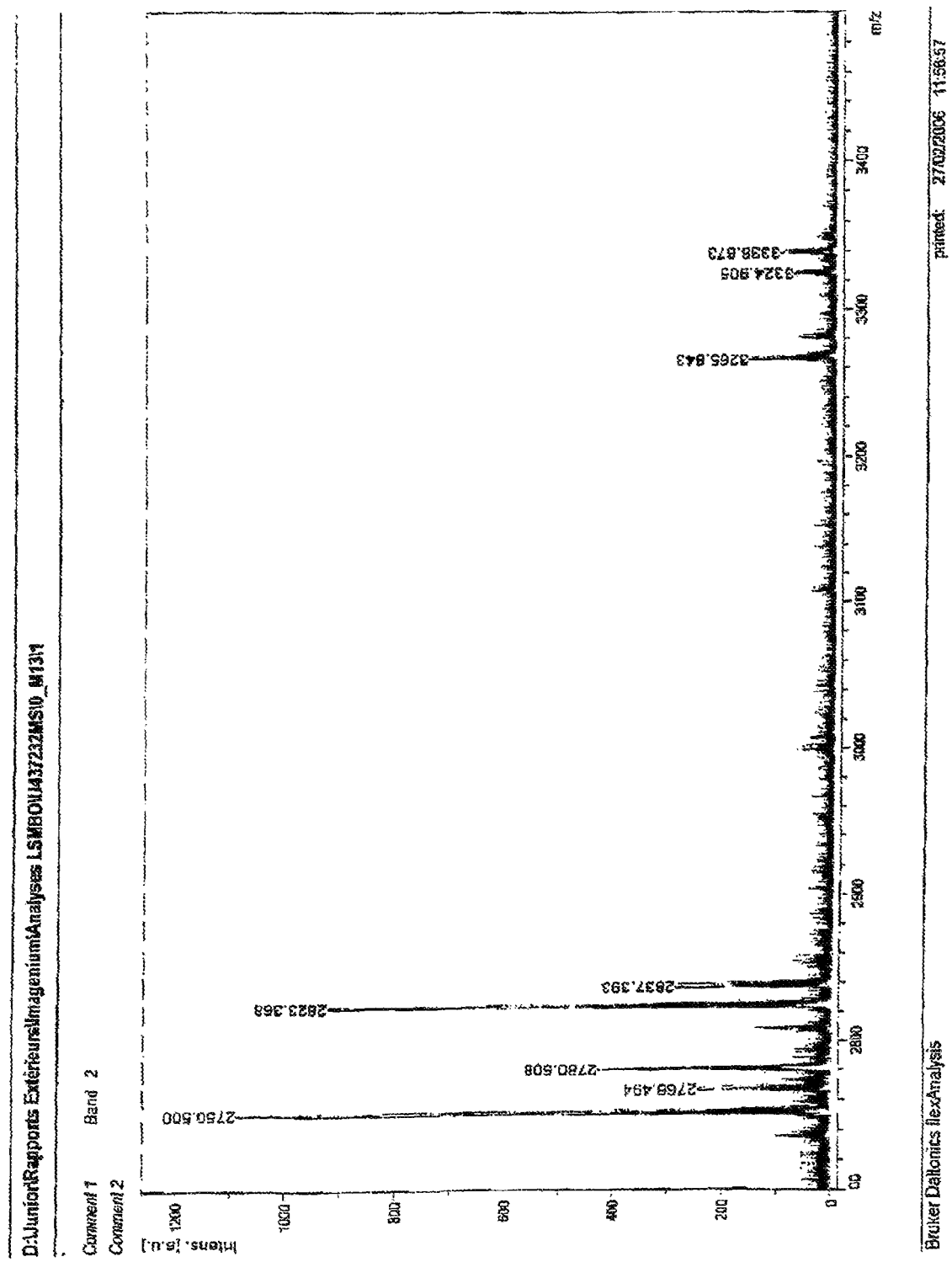

This protein has been characterized by mass spectrometry (Maldi) (Example 1; FIGS. 1, 2, 3). It gives more than 54 peptides following digestion with Promega trypsin (FIG. 7). The characteristics of the LIV21 protein are also described in FIGS. 1, 2, 3, 4. 55 specific peptides of LIV21 have been characterized: the LIV21a peptide (SEQ ID No 1), the LIV21b peptide (SEQ ID No 2), and from SEQ No 1 to 55 and to 110.

```
CWTLIEAVGSRAKKEAAAEEAK      (SEQ ID NO: 56)
```

Moreover, two other Liv21 peptides are also described: the LIV21c peptide (SEQ ID No 3), the LIV21d peptide (SEQ ID No 4). The longest sequence is the LIV21e peptide (SEQ ID No 5) KFFVFALILALMLSMTGADSHAKR).

Other specific peptides of LIV21 are described in the additional listing:

Homology with a functional fragment of the zinc finger protein 575 (ZN575-Human): score 13 to 48 and up to 91% overlapping.

```
MLERGAESAAGATDPSPT          (SEQ ID NO: 57)

EAPHQGPPQKPSQSAPGPTASAGSPPR (SEQ ID NO: 58)

RRRPPPQRPHR                 (SEQ ID NO: 59)

CPDCDKAFSYPSK               (SEQ ID NO: 60)

LAHGGARPHPCPDCPK            (SEQ ID NO: 61)

SKLAAHLWTHAPTRPYPCP         (SEQ ID NO: 62)

LAAHLWTHAPTRPYPCP           (SEQ ID NO: 63)
```

Homology with a functional fragment of sulfotransferase 6 (OST6-Human/Q96Q15)

```
MAGSGGLGGGAGG               (SEQ ID NO: 64)

ASRAPMLLVALVL               (SEQ ID NO: 65)

APMLLVALVLGAY               (SEQ ID NO: 66)

TLDGQITMEK                  (SEQ ID NO: 67)
```

Homology with UPI000056685F (mouse) cluster of 290 AAs:

```
PTSLHPYIPASLHPYIPTSLHPYIPASLHP   (SEQ ID NO: 68)
```

Two homologies for the Maldi study of the band 1, first with leucine zipper nuclear factor Gi 1154323:

```
VMADELTNSR                  (SEQ ID NO: 69)

MSIQCDVWRSK                 (SEQ ID NO: 70)

GEFLGQSEGVIEPNK             (SEQ ID NO: 71)

MAETVLRILDPVTCK             (SEQ ID NO: 72)

LLVASVGDDLQYHFER            (SEQ ID NO: 73)
```

And second in the same analysis: homology with BRCA1 (gi 23928365):

```
SQQNRWAESK                  (SEQ ID NO: 74)

MNVEKAEFCNK                 (SEQ ID NO: 75)

NSQGVAWITLNSSIQK            (SEQ ID NO: 76)

VCTKPVESTIEDKIFGK           (SEQ ID NO: 77)
```

Leucine Zipper Domain

```
AGLQEEAQQLRDE               (SEQ ID NO: 78)
```

Homology with cyclin dependant kinase: CSK1 human (P61024)

```
MSHKQIYYSDK                 (SEQ ID NO: 79)

YDDEEFEYRHVMLPK             (SEQ ID NO: 80)

LVPKTHLMSESEWR              (SEQ ID NO: 81)
```

With a preprotein translocase (Q4HL57_Cam1a)

```
KAYECDITYGTNNEFGFDYLR       (SEQ ID NO: 82)

TIMITEAGISKAEK              (SEQ ID NO: 83)
```

An homology with TCFL4 (17q21) in the basic helix loop helix leucine zipper domain.
Mdm2 and HIV:

| | |
|---|---|
| GAVTSSNIAA | (SEQ ID NO: 111) |
| DLDQSV | (SEQ ID NO: 112) |
| EGF and HPV16 EWWRLD | (SEQ ID NO: 113) |
| KNSLD | (SEQ ID NO: 114) |
| MHIESLDS | (SEQ ID NO: 115) |
| LEQVE | (SEQ ID NO: 116) |
| LHLESLKDS | (SEQ ID NO: 117) |

Homology with Semaphorin 4C:

| | |
|---|---|
| ERAVESDCYAEQV | (SEQ ID NO: 84) |
| CVAVGGHSGSLLTQHVM | (SEQ ID NO: 85) |
| ARWTFGGRDLPAEQPGSFLYDARL | (SEQ ID NO: 86) |

Ferrodoxin NADP reductase (score to 60)
Polyribonucleotide nucleotidyl transferase of *pseudomonas syringae* (Q4ZNR6_PSEU2) score at 47: 15% of overlapping.

| | |
|---|---|
| IPGGFFKR | (SEQ ID NO: 87) |
| TVRPLNIEVGVLP | (SEQ ID NO: 88) |
| GITEEIMEIALGQ | (SEQ ID NO: 89) |
| VTDILKEGQEVEV | (SEQ ID NO: 90) |

Human Clathrin (gi 9257202) score to 52 with also an homology with the human olfactive receptor (gi 15293711) score to 32.
An homology with peptides digested to trypsin of ADP/ATP non human translocase (ADT_CHLKE) score to 60 and 30% of overlapping.

| | |
|---|---|
| ETQADPMAFVK | (SEQ ID NO: 91) |
| KTAVAPIERV | (SEQ ID NO: 92) |
| SGQVPRYTGIVNCFVR | (SEQ ID NO: 93) |
| KDTIKGLFPKY | (SEQ ID NO: 94) |
| GGPMALYQGFGVSVQGIIVYR | (SEQ ID NO: 95) |
| KGVLFKDERT | (SEQ ID NO: 96) |
| VAQQEGMKAFFK | (SEQ ID NO: 97) |
| FINPNAVSSASE | (SEQ ID NO: 98) |

Mouse Synthaxine score at 58 and 18% of overlapping found in breast tumors BRCA1.
Homologies of peptide sequences digested by trypsin:

| | |
|---|---|
| SVQALIADFQGTPTFTYK | (SEQ ID NO: 99) |
| YETTGLSESREK | (SEQ ID NO: 100) |
| ANIKDLSHILK | (SEQ ID NO: 101) |
| ERMEPTYQLSR | (SEQ ID NO: 102) |
| FLDDLKTLDQK | (SEQ ID NO: 103) |

Homology with Brca1 of the band to 50 KD but to 100 KD.
SEQ 56: CWTLIEAVGSRAKKEAAAEEAK having an homology with sequence N 6 and GPPSPPPGIPGQP (SEQ ID NO: 104) of KIAA1739 (gi 12698023)

| | |
|---|---|
| CVTLSAQGRGTPKPGLFGAP | (SEQ ID NO: 105) |
| QIMAHFSDVAEAYIEK | (SEQ ID NO: 106) |
| FYAWMIEQAPFSSLAQEGK | (SEQ ID NO: 107) |
| NLYTEIVYTPISTPDGTLVK | (SEQ ID NO: 108) |
| GANNNLFGLDGNVGTTVENTER | (SEQ ID NO: 109) |
| K.FQFGQSTVTLETGR.I | (SEQ ID NO: 110) |

For the purposes of the invention, a preferred LIV21 protein comprises at least one sequence chosen from SEQ ID Nos 1-110 or a sequence having 70%, 80% or preferably 90% homology with said sequence.

The LIV21 complex comprises proteins including 3D helices structures, which have a major functional role for their interactions with the rest of the Liv21 complex.

The present invention concerns a purified or recombinant, isolated human polypeptide having a sequence comprising the sequence SEQ ID No 1 and/or SEQ ID No 2 and/or SEQ ID No 3 and/or SEQ ID No 4 and/or SEQ ID No 5. Preferably, the polypeptide LIV21F comprises the sequences SEQ ID Nos 1, 2 and 5. In a preferred embodiment, the complex is studied based on a sequence selected among the peptide sequences obtained by MALDI (FIGS. 3, 4 and 5). The invention also concerns the three peptides LIV21a (SEQ ID No 1), LIV21b (SEQ ID No 2) and LIV21e (SEQ ID No 5). It also concerns peptides comprising at least 10 consecutive amino acids of human LIV21, preferably at least 20, 30 or 50 consecutive amino acids of LIV21 peptides (i.e. sequences list 1-120 in annexes).

The present invention also relates a polynucleotide encoding for the human protein Liv21, Liv21a and/or Liv21b, generally a polynucleotide encoding for a polypeptide according to the present invention. The polynucleotide encoding for Liv21 may be an mRNA, a cDNA or a genomic DNA. The polynucleotides according to the present invention may be isolated from cells and more particularly from human cells or from human cDNA libraries. They can also be obtained by a polymerase chain reaction (PCR) carried out on the total DNA of the cells or else by RT-PCR carried out on the total cellular RNAs or by chemical synthesis. Probes and primers described in the present invention may be used to isolate and/or prepare a polynucleotype encoding for a protein of the Liv21 complex. It relates also a cloning or expression vector comprising such polynucleotide.

Such vector may include the elements required for the expression (expression vector) and eventually for the secretion of the protein in a host cell (signal peptide of secretion). Preferably the said vectors comprise a promoter, signals of initiation and termination of translation, as well as adapted regions for transcription regulation. The vector can be a plasmid, a cosmid, a BAC, a phage, a virus, or other. The invention relates to a host cell or a non-human transgenic animal including a vector or a polynucleotide according to the present invention.

The invention also concerns LIV21 derivatives of interest, which are, for example, fusion proteins in which LIV21 is fused to labelled proteins such as GFP. Moreover, the LIV21 protein can be labelled by any means known to those skilled in the art.

The present invention also concerns an antibody, which binds specifically to a polypeptide according to the present invention, preferably human LIV21, or a fragment or a derivative thereof. In a specific embodiment, the antibody binds specifically to an LIV21a or LIV21b peptide.

The antibodies may be polyclonal or monoclonal. They may be antibody fragments and derivatives having substantially the same antigenic specificity, in particular antibody fragments (for example, Fab, Fab'2, CDRs), humanized antibodies, polyfunctional antibodies, single-chain antibodies (ScFv), etc. The antibodies of the invention can be produced using conventional methods, including the immunization of an animal and the recovery of its serum (polyclonal) or of spleen cells (so as to produce hybridomas by fusion with appropriate cell lines).

Said antibodies can be obtained directly from human serum or from serum of animals immunized with the proteins or the peptides according to the present invention. Methods for producing polyclonal antibodies from varied animal species including rodents (mice, rats, etc.), primates, horses, pigs, sheep, rabbits, poultry, etc., are described, for example, in Vaitukaitis et al. (Vaitukaitis, Robbins et al. 1971). The antigen is combined with an adjuvant (for example, Freund's adjuvant) and administered to an animal, typically by subcutaneous injection. Repeated injections can be carried out. Blood samples (immune serum) are collected and the immunoglobulins are separated.

The present invention concerns an anti-LIV21 serum produced by immunizing an animal with a polypeptide according to the present invention. In a specific embodiment, the animal was immunized with the LIV21a and/or LIV21b peptide. In a preferred embodiment, the animal is immunized with these two peptides.

For example, the peptides can be coupled to a carrier protein such as hemocyanin, and then injected into an animal, for example a rabbit, for immunization. Polyclonal antibodies were obtained using these two peptides by having immunized two rabbits and having bled one rabbit so as to have a preimmune serum.

Methods for producing monoclonal antibodies from various animal species can be found, for example, in Harlow et al. (Harlow 1988) or in Kohler et al. (Kohler and Milstein 1975). These methods include the immunization of an animal with an antigen, followed by the recovery of the spleen cells, which are subsequently fused with immortalized cells, such as myeloma cells. The resulting hybridomas produce monoclonal antibodies and can be selected by limiting dilution so as to isolate the individual clones. The antibodies can also be produced by selection from combinatorial libraries of immunoglobulins, such as those disclosed, for example, in Ward et al. (Ward, Gussow et al. 1989).

The invention also includes the use of the antibodies according to the invention for the detection and/or the purification of the human LIV21 protein. In particular, the LIV21-specific antibodies can be used for the detection of these proteins in a biological sample. They thus constitute a means of immunocytochemical or immunohistochemical analysis * or by microfludic analysis of LIV21 expression on tissue sections. Generally for such analyses, the antibodies used are labelled in order to be detectable. As an alternative, the antibodies can be indirectly labelled.

In a preferred embodiment, the antibodies are labelled. The labels include radiolabels, enzymes, fluorescent, luminescent or chemical labels, magnetic particles, gold labelling, biotin/avidin labelling, peroxidase labelling, etc.

The invention also includes a method for detecting the LIV21 protein in a biological sample, comprising a step of suitable treatment of the cells by any appropriate means which makes it possible to render the intracellular medium accessible, a step of bringing said intracellular medium thus obtained into contact with an antibody specific for the human LIV21 protein and a step of demonstrating the LIV21-antibody complex formed, by any appropriate means. In specific embodiments, the cytoplasmic and/or nuclear extracts are prepared, and these extracts are brought into contact with the antibody specific for the human LIV21 protein.

Diagnosis

The present invention teaches the development of the pharmaco diagnostic test, which also makes it possible to monitor the evolution of a cell proliferation. In particular, the present invention makes it possible to monitor the evolution of a cell proliferation on fresh cells or tissues, on frozen cells or tissues and on tissues processed, inter alias, with paraffin. The applications may be the diagnosis of cancer and also the monitoring of the evolution of a cell proliferation. Preferably, the cancer is selected from breast cancer, bladder cancer, ovarian cancer, lung cancer, skin cancer, prostate cancer, colon cancer, liver cancer, a sarcoma, a leukaemia and glioblastoma, without being limited thereto.

Five of these properties can be used: its passage from the cytoplasmic cellular compartment to the nuclear compartment, the property of associating with the E2F4 transcription factor in order to form a complex which inhibits the expression of the E2F1 factor, and the ability of LIV21 to translocate in the nucleus through specific inhibition of PKCε, the sumoylation of LIV21 when the latter is nuclear and integrated into PML bodies and its interaction with HDAC.

The different properties of Liv21 may be exploited by any mean of optic imaging, sonic and of current spectroscopy. The predominantly cytoplasmic state of this protein in cases of cancer, compared with its nuclear location in normal cells, is a geographical and structural difference which makes it possible, without the need for a fluorescent label, to differentiate spectral profiles of the functional pattern of cancerous tissue versus normal tissue, and thus to make the diagnosis.

These results show that the cytoplasmic localization of LIV21 protein complex and the nuclear localization of other proteins of this complex is an indicator of the aggressiveness and of the metastatic potential of the cancer. The detection of the LIV21 complex proteins expression indicates the presence of cancer cells, more particularly of invasive, aggressive and/or metastatic cancer cells.

The invention concerns, moreover, methods for the diagnosis or prognosis of cancer which implement the detection of the cytoplasmic localization of a transcription factor located in the nucleus in normal cells.

The present invention concerns a method for the detection of cancer cells in a biological sample from a patient, comprising the detection of the product of expression of the LIV21 gene in the nucleus and/or the cytoplasm of the cells in the biological sample from said patient, localization of said product of expression of the LIV21 gene in the cytoplasm being indicative of the presence of cancer cells and localization of said product of expression of the LIV21 gene in the nucleus being indicative of the presence of noncancer cells. Preferably, localization of said product of expression of the LIV21 gene in the cytoplasm is indicative of the presence of invasive and/or metastatic cancer cells. The method preferably comprises a prior step of suitable treatment of the cells contained in the sample by any appropriate means, which makes it possible to render the intracellular medium accessible. The method optionally comprises a step of comparison with a biological sample, which does not contain cancer cells.

Optionally, the method according to the invention also comprises the detection of the product of expression of at least one gene selected from the group consisting of the protein kinase C epsilon (PKCε) gene, the E2F1 gene and the E2F4 gene. The method can in particular comprise the detection of the product of expression of two of these genes or of the three genes. Moreover, at least one of the ratios LIV21/PKCε, LIV21/E2F4 and LIV21/E2F1 can be determined in the present method. This ratio can be determined in the cytoplasm and/or in the nucleus. Preferably, these ratios are determined in the nucleus. Preferably, these ratios are compared with those obtained in a normal cell.

In one embodiment, the expression product of the genes is detected at the mRNA level, it being possible for the mRNA to be detected by any means known to those skilled in the art.

Thus, the method according to the present invention also relates to the detection of a polynucleotide encoding the human LIV21 protein or a fragment thereof, for example LIV21a and/or LIV21b. The polynucleotide encoding LIV21 may be an mRNA, a cDNA or a genomic DNA. The polynucleotides may be isolated from cells of the biological sample. They may also be obtained by a polymerase chain reaction (PCR) carried out on the total DNA of the cells or else by RT PCR carried out on the total RNA of the cells or polyA RNAs.

The mRNA may be detected by an RT PCR analysis. For this, the method uses a pair of primers specific for the expression product to be detected, in particular LIV21, PKCε, E2F1 or E2F4. The term "specific pair of primers" is intended to mean that at least one of the primers is specific for the expression product to be detected, i.e. that this pair of primers makes it possible to specifically amplify a fragment of the desired mRNA. Preferably, the RT PCR analysis is carried out on nuclear and/or cytoplasmic extracts of the cells contained in the sample from the patient. Optionally, the RT PCR analysis may be a quantitative analysis. A pair of primers specific for LIV21 can be prepared on the basis of the teachings of the present application. For example, the pair of primers may comprise the primers described in the sequences listing SEQ ID Nos 3 and 4.

The pairs of primers specific for PKCε, E2F1 and E2F4 are well known by those skilled in the art (Caroll J S 2000; Mundle S D 2003; Stevaux O 2002; Cheng T 2002; Opalka B 2002).

The mRNA may also be detected by Northern blotting analysis. For this, the method uses a probe specific for the expression product to be detected, in particular LIV21, PKCε, E2F1 or E2F4. A probe specific for LIV21 can be prepared on the basis of the teachings of the present application. An example of a specific probe comprises the sequence SEQ ID No 5. Preferably, the Northern blotting analysis is carried out on nuclear and/or cytoplasmic extracts of the cells contained in the sample from the patient. The nucleic probe is labelled. The oligonucleotide labelling technique is well known to those skilled in the art. The labelling of the probes according to the invention can be carried out with radioactive elements or with non radioactive molecules. Among the radioactive isotopes used, mention may be made of $^{32}P$, $^{33}P$ or $^{3}H$. The non radioactive entities are selected from ligands such as biotin, avidin, streptavidin or digoxigenin, haptens, dyes and luminescent agents such as radioluminescent, chemiluminescent, bioluminescent, fluorescent or phosphorescent agents. The probes specific for PKCε, E2F1 and E2F4 are well known to those skilled in the art.

In a preferred embodiment, the expression product of the genes is detected at the protein level. Preferably, the protein is detected using a specific antibody.

Thus, the method comprises a step of bringing the cells of the biological sample into contact with an anti-human LIV21 antibody. Antibody against each protein or peptide of Liv 21 complex.

The antibodies may be monoclonal or polyclonal. The anti-LIV21F antibody can, for example, be an anti-LIV21F serum. The anti-histone antibody can be a monoclonal antibody. For the antibodies directed for example against transcription factors or the translocases, the use of such antibodies as drugs inhibiting signal transduction will be conducted systematically after having examined the expression profile of the cDNA or antibody and/or protein biochip. Chimera antibodies are also part of this application (i.e. for example the fusion protein PML/RAR, chromosome 15/17). Depending on the expression level of proteins or genes of each individual having a tumor, we will have to adjust the posology of administration of one or more antibodies, siRNA and/or chemical treatments known by those skilled in the art and already used in this type of pathologies at this evolution stage. At early stages this relates to a pharmacogenomic treatment, meaning that it would be the most suitable on the individual scale as a function of the expression pattern of each gene and protein of interest and of its expression level in its cellular compartment studied for each protein of interest. This kind of approach can evolve very fast in order to monitor expression profiles common to subtypes of individuals having the same form of cancer at the same stage (the normalization needs to be studied in cohorts of patients with a well characterized phenotype versus healthy individuals). Breast cancer is one of the hardest to address by this new therapeutic method as its phenotypic heterogeneity is well known. Anticancer chemical compounds including for example IL2, interferon, kinase inhibitors or anti-mitotic drugs described in the literature do not belong to the compounds according to the invention, while the pharmaceutical compositions including them as their use in therapy are part of the present invention.

When the product of expression of one of the genes PKCε, E2F1 and E2F4 must be detected, the method can use antibodies specific for the PKCε, E2F1 and E2F4 proteins, respectively. Polyclonal and monoclonal antibodies directed against PKCε, E2F1 and E2F4 are commercially available. By way of example, mention may be made of, for PKCε, a rabbit polyclonal antibody (Santa Cruz Technology, sc-214), for E2F1, a rabbit polyclonal antibody (Santa Cruz Technology, sc-860), and for E2F4, a rabbit polyclonal antibody (Santa Cruz Technology, sc-866). Preferably, the antibodies are labelled, directly or by means of a secondary antibody. The antibody labelling techniques are well known to those skilled in the art.

In a specific embodiment, the protein can be detected by Western blotting analysis. The Western blotting analysis can be carried out on nuclear and/or cytoplasmic extracts of the cells contained in the sample from the patient. Briefly, the proteins are migrated in a gel and then blotted onto a membrane. This membrane is then incubated in the presence of the antibodies and the binding of the antibodies is optionally revealed using labelled secondary antibodies.

In another embodiment, the protein is detected by immunohistochemistry, immunocytochemistry or immunoradiography. These techniques are well known to those skilled in the art. The immunocytochemical analysis can be carried out on whole cells originating from the sample or which are derived there from, for example by cell culture. It can also be carried out on isolated nuclei. The immunohistochemical analysis can be carried out on mammary tissue sections.

By way of illustration, an immunocytochemical analysis can include the following steps. However, it is understood that other preparatory methods can be carried out. Cells originating from the biological sample are cultured, preferably on slides (Lab Tek, Nunc, Germany), and then washed with buffer and fixed with paraformaldehyde (for example, 4%). A saturation step is preferably carried out by incubating the cells with buffer S (PBS-0.1% Triton X100—10% FCS). The cells are then incubated with a primary antibody and are then washed and incubated with a fluorescent secondary antibody, if necessary. The nuclei can be labeled with propidium iodide (Sigma). The slides are mounted in moviol for observation by fluorescence microscopy. Moreover, isolated nuclei sampled during a nuclear extraction can be fixed with paraformaldehyde (for example, 4%). The suspensions of nuclei are deposited between a slide and cover slip and the observation is carried out by fluorescence microscopy and by confocal microscopy. The primary antibodies are, for example, rabbit antibodies and the secondary antibodies are labelled antibodies directed against rabbit IgGs.

The biological samples originate from a patient potentially suffering from cancer or for whom it has been established that said patient is suffering from cancer. "Biological sample" is intended in particular to mean a sample of the biological fluid, living tissue, tissue fragment, mucosity, organ or organ fragment type, or any culture supernatant obtained by means of taking a sample. The method according to the present invention can comprise a step of taking a biological sample from the patient. The detection step can be carried out directly on a tissue section of the sample, or on a culture of cells originating from the sample, or on total cell extracts, nuclear extracts and/or cytoplasmic extracts.

In a specific embodiment of the method comprising the detection of the product of expression of the PKCε gene, a significant increase in PKCε is indicative of the presence of cancer cells. More specifically, the amount of PKCε in normal cells is compared with the amount of PKCε in the cells of the sample, and the significant increase is determined by means of this comparison. The method according to the present invention can optionally comprise the measurement of the LIV21/PKCε content. This LIV21/PKCε ratio increases in the cytoplasmic fraction of cancer cells compared with normal cells.

In another specific embodiment of the method comprising the detection of the product of expression of the E2F4 gene, the method comprises the detection of the association of LIV21 with the E2F4 protein, and a decrease in this association is indicative of the presence of cancer cells. The detection of the association of LIV21 with the E2F4 protein can be carried out by concurrent detection of LIV21 and of E2F4. The method according to the present invention can optionally comprise the measurement of the E2F4/LIV21 content. This E2F4/LIV21 ratio decreases in the nucleus of cancer cells compared with normal cells.

In an additional embodiment of the method comprising the detection of the product of expression of the E2F1 gene, the presence of the E2F1 protein in the nucleus is indicative of the presence of cancer cells. The method according to the present invention can optionally comprise the measurement of the E2F1/LIV21 content. This E2F1/LIV21 ratio increases in the nuclear fraction of cancer cells compared with normal cells.

The method according to the present invention allows in particular the detection of metastasized cancer, therapeutic monitoring and/or recurrences following treatment and makes it possible to determine the degree of invasiveness of a cancer. The specificity of the detection can be related to the crossing over of information obtained through the existence and the topography of LIV21 by all imaging and spectroscopy means and obtained by combination with other known cancerological indicators via protein arrays or microarrays. Thus, the detection based on LIV21 can be combined with the detection of other cancer markers, in particular breast cancer markers, known to those skilled in the art.

In fact, the present invention concerns a method for the therapeutic monitoring of an anticancer treatment in a patient suffering from cancer, comprising the administration of the anticancer treatment to said patient and the detection of cancer cells in a biological sample from the patient, according to the method of the present invention. A decrease in cancer cells will be indicative of the effectiveness of the treatment. The detection of cancer cells in a biological sample from the patient, according to the method of the present invention, can be carried out once or several times over the course of the anticancer treatment or after the anticancer treatment. Preferably, the biological sample originates from the tissue affected by the cancer treated.

Moreover, the present invention also concerns a method for the detection of recurrences subsequent to an anticancer treatment of a cancer in a patient, comprising the detection of cancer cells in a biological sample from the patient, according to the method of the present invention. The detection of cancer cells in a biological sample from the patient, according to the method of the present invention, can be carried out once or several times after the anticancer treatment. The detection of cancer cells is indicative of recurrences. Preferably, the biological sample originates from the tissue affected by the cancer treated.

The present invention also describes a kit for carrying out a method according to the invention. More particularly, the invention concerns a kit for the detection of cancer cells in a biological sample from a patient, comprising one or more elements selected from the group consisting of an antibody which binds specifically to human LIV21 according to the present invention and an anti-LIV21 serum according to the present invention, an oligonucleotide probe specific for the LIV21 mRNA and a pair of primers specific for the LIV21 mRNA. In a preferred embodiment, the kit comprises antibodies, which bind specifically to human LIV21. In another preferred embodiment, the kit comprises an oligonucleotide probe specific for the LIV21 mRNA. It may also comprise a probe specific for a "housekeeping" gene.

The kit according to the present invention can comprise reagents for the detection of an LIV21-antibody complex produced during an immunoreaction.

Optionally, the kit according to the present invention also comprises means for detecting the product of expression of at least one gene selected from the group consisting of the protein kinase C epsilon (PKCε) gene, the E2F1 gene and the E2F4 gene. This detection means can be antibodies specific for the protein, oligonucleotide probes specific for the mRNA concerned and/or a pair of primers specific for the mRNA.

The present invention also relates to a diagnostic composition comprising one or more elements selected from the group consisting of an antibody according to the present invention and a serum according to the present invention, an oligonucleotide probe specific for the LIV21 mRNA and a pair of primers specific for the LIV21 mRNA.

Anticancer Therapy

In the context of an anticancer therapy, it is possible to envision increasing the amount of LIV21 present in the nucleus. For this, the nuclear localization in cancer cells of LIV21 expression could be promoted. Liv21 being able to translocate in the nucleus by itself, one could envisage the construction of an expression vector including a polynucleotide coding for human Liv21 in order to over express these protein in the cell nucleus for that we wish regulate the proliferation.

The expression vector encoding Human Liv21 can be administrate in vivo to the patient by any mean known by those skilled in the art.

For example, the expression vector can be administrated as naked DNA (for example EP 465 529). The microinjection, electroporation, phosphate of calcium precipitation techniques and formulations using nanocapsules or liposomes are other techniques available.

The expression vector may also be in the form of a recombinant virus, including, a polynucleotide encoding human Liv21 inserted into its genome.

The viral vector can be selected for example from an adenovirus, a retrovirus, in particular a lentivirus, and a virus adeno-Associated (AAV), a herpes virus (HSV), a cytomegalovirus (CMV), a vaccine virus, etc. . . . So advantageous, the recombinant virus is a defective virus.

Preferably, the expression vector permits a cellular targeting. So this vector could target cancer cells or a particular cell type that is affected by cancer. Targeting of particular cellular type can be realized by placing the polynucleotide coding Liv21 under the control of a promoter tissue-specific. In another alternative the expression vector may be targeted, for example, in association with a specific molecule of a particular tissue or cancer cells, for example a specific antibody to a molecule expressed specifically by the particular tissue or the cells of cancer.

Also the choice of expression vector may also influence the cellular targeting. Indeed, if the vector is a virus, the virus tropism natural or amended may also allow a certain target.

The present invention concerns a pharmaceutical composition comprising a polynucleotide encoding for Liv21, more particularly an expression vector coding for Liv21. It also concerns the use of a pharmaceutical composition comprising a polynucleotide encoding for Liv21, in particular an expression vector encoding for Liv21 as medicament. Preferably, the present invention concerns the use of a pharmaceutical composition comprising a polynucleotide encoding for Liv21, in particular an expression vector encoding for Liv21, for the preparation of a medicament for use in treating cancer. Finally, it concerns a method for treating cancer in a patient, comprising the administration to the cancer cells of a polynucleotide encoding for Liv21, Liv21 expression making it possible to reduce or abolish the cancerous phenotype of the treated cells. Preferably, cancer is selected from breast cancer, bladder cancer, ovarian cancer, lung cancer, skin cancer, prostate cancer, colon cancer, a glioblastoma, without being limited thereto.

For this, the nuclear localization of LIV21 could be promoted, for example by decreasing the activity of PKCε in the cancer cells and by using HDAC inhibitors.

In another specific embodiment of anticancer therapy, it is possible to envision decreasing the activity of PKCε in the cancer cells. This decrease in activity can be produced by decreasing the activity of the PKCε protein or by decreasing its expression. A decrease in the activity of the PKCε protein can be obtained by administering PKCε-protein inhibitors to the cancer cells. The PKCε-protein inhibitors are well known to those skilled in the art. A decrease in the expression of the PKCε protein can be obtained by using antisenses or siRNA specific for the PKCε gene. Kits are commercially available. Moreover, the techniques concerning inhibition by means of antisense or siRNA are well known to those skilled in the art (Arya R 2004, Lee W 2004, Sen A 2004, Platet N 1998, Hughes 1987).

The present invention therefore concerns a pharmaceutical composition comprising a PKCε-protein inhibitor. It also concerns the use of a pharmaceutical composition comprising a PKCε-protein inhibitor as a medicament, in particular for the preparation of a medicament for use in treating cancer. Finally, it concerns a method for treating cancer in a patient, comprising the administration to the cancer cells of a PKCε-protein inhibitor, the pKCε-protein inhibitor making it possible to reduce or abolish the cancerous phenotype of the treated cells. In a first embodiment, the PKCε-protein inhibitor decreases the activity of the PKCε protein. In a second embodiment, the PKCε-protein inhibitor decreases the expression of the PKCε protein. Preferably, cancer is selected from breast cancer, bladder cancer, ovarian cancer, lung cancer, skin cancer, prostate cancer, colon cancer, liver cancer, a sarcoma, a leukaemia and glioblastoma, without being limited thereto. PKC epsilon inhibitors are published and commercially available for other applications.

In the context of a therapy for a neurodegenerative disease, it is possible to envision decreasing the amount of LIV21 present in the nucleus.* The cells affected by the neurodegenerative disease are generally neurons, motorneurons, etc. In a preferred embodiment, the neurodegenerative disease is chosen from Alzheimer's disease, Huntington's disease, Parkinson's disease and amyotrophic lateral sclerosis (ALS). The inhibition or the blocking of LIV21 expression can be carried out by any means known to those skilled in the art. In particular, by way of illustration, mention may be made of the antisense strategy, siRNA and ribozymes. Thus, an antisense oligonucleotide or an expression vector encoding this antisense oligonucleotide could be prepared and used to block the translation of the mRNA encoding LIV21 in vivo. Moreover, a ribozyme can be prepared for cleaving and destroying, in vivo, the mRNA encoding LIV21. It is also possible to envisage a triple-helix strategy in which an oligonucleotide is designed so as to hybridize with the gene encoding LIV21 and to thus block the transcription of this gene.

*Applications. For that, the Liv21 expression could be decreases or blocked in nuclear of the diseased cells of neurodegeneration.

For this, the nuclear localization of LIV21 could also be hindered, for example by increasing the activity of PKCε in the cells affected by the neurodegenerative disease.

In one particular therapeutic method against neurodegenerative diseases, it is possible to envision increasing PKC epsilon activity in the cells affected by the neurodegenerative disease. This increase in activity can be produced by increasing the activity of the PKCε protein or by increasing its expression.

An increase in the activity of the PKCε protein can be obtained by administering PKCε-protein activators to the cells affected by the neurodegenerative disease. The PKCε-protein activators are well known to those skilled in the art (Toma O (2004), Activation of PKCs by DAG, AGPI: oleic acid, linoleic acid, arachidonic acid, etc. Activation and proteolysis of PKCs in gonadotropic cells: Communication 2004 by Macciano H, Junoy B, Mas J L, Drouva S V, UMR6544 Marseille). An increase in the expression of the PKCε protein can be obtained by using expression vectors encoding the PKCε protein and which make it possible to overexpress it in the cells affected by the neurodegenerative disease.

Thus, the present invention concerns a pharmaceutical composition comprising a PKCε-protein activator or an expression vector encoding the PKCε protein. It also concerns the use of a PKCε-protein activator or of an expression vector encoding the PKCε protein, for the preparation of a medicament for use in the treatment of a neurodegenerative disease.

Screening Method

The invention concerns methods for the selection, identification, characterization or optimization of active compounds, which decrease cell proliferation, based on the measurement of the nuclear versus cytoplasmic localization of LIV21, or of the binding of the LIV21 protein to the E2F4 protein.

In a first embodiment, the selection, the identification, the characterization or the optimization of active compounds of therapeutic interest comprises bringing a candidate compound into contact with a cell and determining the nuclear versus cytoplasmic localization of the LIV21 expression product. An increase in the nuclear localization of LIV21 indicates that the candidate compound is active in terms of decreasing or abolishing cell proliferation. A decrease in the nuclear localization of LIV21 indicates that the candidate compound is active in terms of treating or preventing a neurodegenerative disease.

In a second embodiment, the selection, the identification, the characterization or the optimization of active compounds of therapeutic interest comprises bringing a candidate compound into contact with a cell and determining the level of expression of the gene encoding the PKCε protein. A decrease in the expression of PKCε indicates that the candidate compound is active in terms of decreasing or abolishing cell proliferation. An increase in the expression of PKCε indicates that the candidate compound is active in terms of treating or preventing a neurodegenerative disease.

In a third embodiment, the selection, the identification, the characterization or the optimization of active compounds of therapeutic interest comprises bringing a candidate compound into contact with a cell and determining the level of LIV21/E2F4 complex. An increase in the level of LIV21/E2F4 complex indicates that the candidate compound is active in terms of decreasing or abolishing cell proliferation. A decrease in the level of LIV21/E2F4 complex indicates that the candidate compound is active in terms of treating or preventing a neurodegenerative disease.

In a fourth embodiment, the selection, the identification, the characterization or the optimization of active compounds of therapeutic interest comprises bringing a candidate compound into contact with a cell and determining the level of expression of the gene encoding the E2F1 protein. A decrease in the expression of E2F1 indicates that the candidate compound is active in terms of decreasing or abolishing cell proliferation. An increase in the expression of E2F1 indicates that the candidate compound is active in terms of treating or preventing a neurodegenerative disease.

The invention also relates to a method of screening for a compound capable of interacting in vitro, directly or indirectly, with LIV21, characterized in that: in a first step, the candidate compound and LIV21 are brought into contact and, in a second step, the complex formed between said candidate compound and LIV21 is detected by any appropriate means.

The present invention also relates to a method of screening for a compound capable of modulating (activating or inhibiting) the activity of the LIV21 protein, characterized in that: in a first step, cells of a biological sample expressing the LIV21 protein are brought into contact with a candidate compound, in a second step, the effect of said candidate compound on the activity of said LIV21 protein is measured by any appropriate means, and in a third step, candidate compounds capable of modulating said activity are selected. The activity of LIV21 can, for example, be estimated by means of evaluating the ability of the cell to divide, by measuring the expression of the E2F1 gene or by the cytoplasmic and/or nuclear localization of LIV21.

The candidate compound can be a protein, a peptide, a nucleic acid (DNA or RNA), a lipid, or an organic or inorganic compound. In particular, the candidate compound could be an antibody, an antisense, a ribozyme or an siRNA.

Other advantages and characteristics of the invention will appear in the examples and the figures which follow, and which are given in a nonlimiting manner.

EXAMPLES

Example 1

Extraction of Proteins of the Liv21 Complex

The MCF-7 Cell Line

The MCF-7 line is a non clonal human line of breast adenocarcinoma cells. During their differentiation induced by exogenous factors, these cells develop a hypertrophy, membrane protrusions and a tendency to dissociate from one another. They acquire a secretory phenotype which is characterized by the appearance of numerous granules and of secretory canaliculi.

In vivo, these cells are relatively non metastatic and this low invasiveness is thought to be due to a low constitutive activity of the protein kinases C (PKCs) and to a relatively low level of expression of protein kinase C alpha.

This line is used in many studies on proliferation, differentiation and apoptosis. These studies use appropriate drugs, such as TNF for the induction of apoptosis, or TPA (12-O-tetradecanoyl phorbol-13-SUMOate) for the induction of differentiation and therefore for the study of departure from the cell cycle.

Extraction of Proteins of the Liv21 Complex

After culture cells MCF7 (ATCC passage 15) and cell extraction, 5 mg of protein are centrifuged after homogenization in 10 ml RIPA buffer, antiprotease added. These protein extracts went loop for seven hours at a peristaltic pump on a column of affinity (HITRAP NHS ACTIV HP 1×5 ml: Article and catalog 17071701) which was set Liv21 antibody. Wash 3 times, 10 ml in RIPA buffer and then a half-eluting fractions of 500 nl in a buffer glycine PH2/HCL, then control gel SDS Page 10% (deposit of 25 nl of the fraction) followed by a western blot to verify. Revelation of a band on gel at 51 kD flanked by two other bands at 50 and 52 kD respectively and a lower trace of a band 80 kD and 100 kD in gel mono dimensional (FIG. 1A). By Moreover revelation of 12 spots between 50 kD and 70 kD in bidimensional gel (FIGS. 1B and 2).

```
Peptide LIV21a
RVYGPLTNPKPQ              SEQ ID NO: 150

Peptide LIV21b
CYRSILHTKV                SEQ ID NO: 151

Peptide LIV21c
SYMSMFLLLMAISCVIAK        SEQ ID NO: 152

Peptide LIV21a
PLMIIHHLDDCPHSQALK        SEQ ID NO: 189

Peptide Liv21a
KFFVFALILALMLSMCGADSHAKR  SEQ ID NO: 153
```

Mass spectrometry (MALDI) was realized for the LIV21 protein and its complex. The LIV21 protein was digested with trypsin. The peptides derived from the digestion are solubilized in a solvent: acetonitrile/water (1/1) containing 0.1% of TFA (trifluoroacetic acid). A saturated solution of the alpha-cyano-4-hydroxycinnamic matrix was prepared in the same solvent. The same volume of the two solutions was taken and mixed together and 1 μl was deposited onto the MALDI plate for analysis. The mass spectrometry showed that the LIV21 protein and its complex digested with trypsin reveals hundred peptides following the band of gel extracted between 49 and 54 kD (cf. FIGS. 3-5). The LIV21 protein was characterized by a molecular weight of 50 kD, revealed by Western blotting and by a two-dimensional SDS PAGE gel (FIG. 2). But we find a product of 100 kD at 130 kD which could be a Liv21 dimere.

Example 2

Mass Spectrometry

A mass spectrometry (MALDI) was realized for the LIV21 protein and its complex. The LIV21 protein was digested with trypsin. The peptides derived from the digestion are solubilized in a solvent: acetonitrile/water (1/1) containing 0.1% of TFA (trifluoroacetic acid). A saturated solution of the alpha-cyano-4-hydroxycinnamic matrix was prepared in the same solvent. The same volume of the two solutions was taken and mixed together and 1 μl was deposited onto the MALDI plate for analysis. The mass spectrometry showed that the LIV21 protein and its complex digested with trypsin reveals hundred peptides following the band of gel extracted between 49 and 54 kD (cf. FIGS. 3-5). The LIV21 protein was characterized by a molecular weight of 50 kD, revealed by Western blotting and by a two-dimensional SDS PAGE gel (FIG. 2). But we find a product of 100 kD at 130 kD which could be a Liv21 dimer.

When it changes cell compartment and when it is sumoylated, the LIV21 protein has a molecular weight of approximately 60 kD. When it is phosphorylated in the cytoplasm, it exhibits two forms which differ by a few kilobases. A doublet is then observed.

Example 3

Analysis of Sequences in the Proteomic Databases

Several peptides in the patent in listing of the patent characterize it:

```
Peptide LIV21b
FVFALILALMLSMCG            SEQ ID NO: 51

Peptide LIV21b
KFFVFALILALMLSMCGADSHAKR   SEQ ID NO: 15
```

For example, the inventor obtained a score very significative of 81, hoped: 0.0012 for the histatin 3-2 variant with 52% of overlapping of sequences between the tested sample and histatin, this sequence SEQ ID No 5 is commune to Liv21 and HIS3-HUMAN FIGS. 6 and 7). Using different database and a ppm which differed to 20 to 50 ppm, we obtain the same sequence for the commune part: SEQ ID No 51.

Example 4

Reverse Transcriptions

After MCF7 cells (ATCC passage 15) had been thawed and cultured up to 200 million, they were trypsinized and frozen at −80° C. The RNA was extracted from two pools of 50 million cells with the Nucleospin RNA L kit (Macherey Nagel) ref. 740.962.20, resulting in a pool 1 of 318 μg and a second of 182 μg.

The poly A+ RNA was extracted from 313 μg of total RNA of pool 1 using the oligo Tex mRNA Midi kit (Qiagen) ref. 70042.

I Reverse Transcription:

The RNA was reverse transcribed with the Fermentas Revert Aid H minus M MuLV Reverse Transcriptase, ref. EP0451 batch 1124, with 3.64 μg of total RNA and 0.45 μg of mRNA, according to the supplier's conditions, with an oligo dT primer. Reactions were carried out at 2 different temperatures at 45° C. and 55° C. so as to eliminate the RNA structures that may hinder reverse transcription.

II PCR

The PCRs were carried out with the reverse transcriptions as templates, initially with the primers A1+oligo dT. Nested PCRs were subsequently carried out on these first PCRs, with the primers A1+Splicing, A1+GDBR1, or ATG+Splicing, ATG+GDBR1.

PCR amplification was then carried out with the primers specific for the genes to be detected, using the cDNAs obtained after oligo dT RT.

Enzyme: Fermentas Taq DNA Polymerase. Thermocycler: Bio Rad iCycler.

The quality of the cDNAs was tested by amplification of GAPDH, b actin and Histone H3.3 housekeeping genes.

TABLE 1

Primers

| Reference | 5'-3' sequence | Amplified fragment size |
|---|---|---|
| Histone N | 5'-GTG GTa aag cac cca gga a-3' (SEQ ID NO: 190) | 347 bp |
| Histone 1 (reverse) | 5'-gct agc tgg atg tct ttt gc-3' (SEQ ID NO: 191) | |
| Hum GAPDH sense | 5'-TGA AGG TCG GAG TCA ACG G-3' (SEQ ID NO: 192) | 983 bp |
| Hum GAPDH antisense | 5'-CAT GTG GGC CAT GAG GTC-3' (SEQ ID NO: 193) | |
| Hum b-actin sense | 5'-GGA CTT CGA GCA AGA GATGG-3' (SEQ ID NO: 194) | 234 bp |
| Hum b-actin antisense | 5'-AGC ACT GTG TTG GCG TAC AG-3' (SEQ ID NO: 195) | |
| LIV21 (A1) | 5'-TCCTATGCTTTGACTATTAG-3' (SEQ ID NO: 128) | |
| LIV21 (A2) | 5'CCTGACATCCCTACATCACCGCA-3' (SEQ ID NO: 129) | |
| odT | 5'-TTTTTTTTTTTTTTTTTTT-3' (SEQ ID NO: 196) | |
| ATG galgal | 5'-ATGTATATTATATCTAA-3' (SEQ ID NO: 130) | |
| Splicing sense histatin | 5'-TGTTGGGATTGCTTATATTT-3' (SEQ ID NO: 133) | |

TABLE 1-continued

Primers

| Reference | 5'-3' sequence | Amplified fragment size |
|---|---|---|
| Splicing reverse histatin | 5'-AAATATAAGCAATCCCAACA-3' (SEQ ID NO: 132) | |
| GDBR 1 reverse | 5'-CTTTATTATTTTGTAAAAT-3' (SEQ ID NO: 134) | |

TABLE 2

PCR mix

| $H_2O$ | 10X buffer | 25 mM $Mg^{++}$ (1.5 mM final concentration) | 10 mM dNTP (µl) | Forward primer 10 µM (µl) | Reverse primer 10 µM (µl) | Taq (µl) 5 U/µl | cDNA (µl) |
|---|---|---|---|---|---|---|---|
| 18.3 | 2.5 | 1.5 | 0.5 | 0.5 | 0.5 | 0.2 | 1 |

PCR Cycles
Denaturation: 94° C. 2 minutes
Denaturation: 94° C. 30 seconds
Annealing: 52-55° C. 1 minute 35 cycles
Elongation: 72° C. 1 minute 30
Final elongation: 72° C. 7 minutes
Conservation: 4° C.
III Controls
THE PCR PRODUCTS WERE SUBSEQUENTLY CONTROLLED ON AGAROSE GELS AND ANALYSED WITH THE BIOCAPT 11.01 SOFTWARE FROM VILBER LOURMAT.
Gel 1 (ie FIG. 7): control of RNA on agarose gel
FIG. 8: RNA pool
FIG. 9: PCR with housekeeping genes and analysis of molecular masses.
FIG. 10: PCR with the primers showing a band of 1400 bp.
FIG. 11: Gel 2 with analysis of molecular masses
FIG. 12: Gel 3 at 55° and analysis of molecular masses
FIG. 13: Gel 4 at 45° and at 55° and analysis of molecular masses.
FIG. 14: screening ligation of 400 pb band, clones B1 to B10.
FIG. 15: screening ligation of 1400 pb band, clones C1 to C10.
FIG. 16: Gel 5: ligation screening on the five new clones.
FIG. 17: Gel 6: Screening of the S55T and S55M recombinant clones and analysis of molecular masses.
Gel 2:

PCRs carried out using templates from PCRs performed with the primers A1+oligo dT on the RTs carried out at 45° C. on the total RNA and the poly A+ RNA (messenger RNA). The primers used for these PCRs are A1+GDBR1 or A1+Splicing reverse.

On the RTs carried out using the total RNA, a band of 1178 1253 bp is amplified with the primers A1+GDBR1 and A1+Splicing reverse. The poly A RNA was used to carry out the RT and is weakly observed at the size (FIG. 10) of 1400 bp for amplification with the primers A1+G, and of 415 bp with the primers A1+Splicing reverse. In the A1+splicing PCR product, there are other bands, of 860 and 233 bp (FIG. 11).
Gel 3:

PCRs carried out using templates from PCRs performed with the primers A1+oligo dT on the RTs carried out at 45° C. on the total RNA and the poly A+ RNA (messenger RNA). The primers used for these PCRs are A1+GDBR1 or A1+Splicing reverse (FIG. 12).

For the PCRs carried out on RTs performed at 55° C., the same overall pattern of bands as that obtained on the RTs performed at 45° C. is found.

No specific amplification is observed when the poly A RNA was used to carry out the RT. On the RTs carried out on the total RNA, a major band of 1554 1609 bp is found with the primers A1+GDBR1 and A1+Splicing reverse. A band at the theoretical size of 1455 bp is expected for an amplification with the primers A1+GDBR1 and a band with the theoretical size of 415 bp is expected with the primers A1+Splicing reverse. In the 2 profiles, very clear bands of 1900-2100 bp and of 1000-1300 bp are found, but with a weaker intensity than that of the band of 1500 1600 bp.

In the A1+splicing reverse PCR product, there is another major band, of 263 bp.
Gel 4:

Nested PCRs carried out using templates from PCRs performed with the primers A1+GDBR1 or A1+Splicing reverse on the RTs carried out at 45° C. on the total RNA and the poly A+ RNA (messenger RNA). The primers used for these PCRs are ATG+GDBR1 or ATG+Splicing reverse (FIG. 13).

The nested PCRs carried out with the primers ATG+GDBR1 give bands at 1213 bp (RT 45° C.) and 1559+1315 bp (RT at 55° C.); the expected theoretical size is 1455 bp. The PCRs carried with the primers ATG+Splice reverse give more varied band profiles.

These PCRs carried out on other PCRs performed with the primers A1+GDBR1 or A1+Splicing reverse.

The presence of a band of 400 bp is noted in the profiles obtained from messenger RNA (the band obtained from the reverse transcription carried out at 55° C. is of greater intensity).

The profiles of the ATG+Splice reverse PCRs carried with total RNA at the start give a band of 424 437 bp of very strong intensity. Bands of 614 and 783 bp of very strong intensity are also found in the profile of the RT 45 and a greater number of bands, but of weaker intensity, is found in the profile of the RT 55, bands at 1118, 936 and 749 bp.

The products of these various PCRs were cloned and sequenced.

Example 5

The PCR products of lanes 2, 4, 6, 7 and 8 were ligated with the plasmid pGEMT Easy, Promega, and the recombinant clones were screened (FIG. 16).
Lane 2: G45T ligations
Lane 4: S45T ligations
Lane 6: G55T ligations
Lane 7: S55M ligations
Lane 8: S55T ligations The recombinant clones obtained were screened (after extraction of the plasmid DNA) by restriction with the Eco RI enzyme, the sites of which border the site of insertion of the PCR products into the pGEMT Easy vector.

Screening of the Recombinant Clones:

The first experiments had been carried out using the ten clones B and the ten clones C, FIGS. 14 and 15, and the results of the sequences of clones B2 and C8 are given in the following example, and exhibit, by sequence comparison between clones, great homology with the clones of the second series of experiments.

Gel 5: Screening of the S45T and G45T Recombinant Clones

Analysis of Molecular Masses

The screening of the clones with Eco RI shows that, out of the 9 S45T clones, 3 have inserts of 100 bp, 216 bp and 410 bp.

On the G45T clones, out of the 6 clones tested, 3 have inserts of 57, 71 and 148 bp.

FIG. 17: screening of the S55T and S55M recombinant clones

Analysis of Molecular Masses

The screening with Eco RI shows that, out of the 13 clones screened, 7 have inserts of sizes between 239 and 637 bp.

The clones G45T5 (148 bp), S45T9 (410 bp), S45T3 (100 bp), S55M1 (491 bp), S55T6 (251 bp) and S55T9 (637 bp) were extracted so as to be sequenced.

Primers used for determining the sequences of the various clones:

```
                                                    (SEQ ID NO: 130)
ATG galgal    5'-atgtatattatatatctaa-3'  INV COMP (SEQ ID NO: 131)
              ttagatatataatatacat (SEQ ID NO: 132)
Splicing      5'---AAATATAAGCAATCCCAACA 3'
reverse- (SEQ ID NO: 133)
Splicing      5'-TGTTGGGATTGCTTATATTT-3' inv comp
reverse (SEQ ID NO: 134)
GDBR1         5'-CTTTATTATTTTGTAAAAT-3'
reverse (SEQ ID NO: 135)
GDBR1         5'-ATTTACAAAATAATAAAG-3' inv comp
reverse
```

Sequences of different clones:
S45T9 (SEQ ID NO:171) size of 450 pb M13 reverse in green (black) indicated the vector and blue the insert.

```
NNNNNNNNNNNGNNCNNGCCGCCNNGGCGGCCGCGGGAATTCGATTAAATATAAGCAATCCCAACACTTTGGNNNGCCGAGGCGGGCGG
ATCACGAGGTCAGGAGATGGAGACCATCCTGGCTAACACAGTGAAACCCTGTCTCTACTGAAAATACAAAAAAGTAGCCGGGCGTGGC
GGCAGGGGCCTGTAGCCCCAGCTACTCAGGAGGCTGAGGCAGGAGAATGGCATGAACCCAGGAGGCAGAGCTTGCAGTGAGCCGAGAT
TGTGCCACTGCACTCCACCCTGGGCAACAGAGCGAGACTCCATCTCAAAAAAAAAAAAAAAATCACCCCAAAGCAATAAGGAGAACTA
GAACAGGACATACACTCCAACACTGGTGAAACTAGGAAAACATATGTAACCCCAAACCACAATATATACACACAAAACTATACGAGAT
GTTGGGATTGCTTAATCACTAGTGAATTCGCGGCCGCCTGCAGGTCGACCATATGGGAGAGCTCCCAACGCGTTGGATGCATAGCTTG
AGTATTCTATAGTGTCACCTAAATAGCTTGGCGTAATCATGGTCATAGCTGTTTCCTGTGTGAAATTGTTATCCGCTCACAATTCCAC
ACAACATACGAGCCGGAAGCATAAAGTGTAAAGCCTGGGGTGCCTAATGAGTGAGCTAACTCACATTAATTGCGTTGCGCTCACTGCC
CGCTTTCCAGTCGGGAAACCTGTCGTGCCAGCTGCATTAATGAATCGGCCAACGCGCGGGGAGAGGCGGTTTGCGTATTGGGCGCTCT
TCCGCTTCCTCGCTCACTGACTCGCTGCGCTCGGTCGTTCGGCTGCGGCGAGCGGNATCAGCTCACTCNANNCGGTAANACNGNTTAT
CCNACANANTCNNNNNNNACNNNNGAAANAANATNNNANCNNNNNNAGCAAAAGGNCNNNNANCNNANAANNNNNNNNNCNNNNNNN
TTTTNCNANNNNGGNNTNNNN

S55M1 (SEQ ID NO: 172) 450 pb m13 REVERSE

NNNNNNGHTCCGGCCGCCATGGCGGCCGCGGGATTCGATTAAATATAAGCAATCCCAACACTTTGGGAGGCCGAGGCGGGCGGATCAC
GAGGTCAGGAGATGGAGACCATCCTGGCTAACACAGTGAAACCCTGTCTCTACGGAAAATACAAAAAAGTAGCCGGGCGTGGCGGCAG
GCGCCTGTAGTCCCAGCTACTCAGGAGGCTGAGGCAGGAGAATGGCATGAACCCAGGAGGCAGAGCTTGCAGTGAGCCGAGATTGTGC
CACTGCACTCCAGCCTGGGCAACAGAGCGAGACTCCATCTCAAAAAAAAAAAAAAATCACCCCAAAGCAATAAGGAGAACTAGAACAG
GACATACACTCCAACACTGGTGAAACTAGGAAAACATATGTAACCCCAAACCACAATATATACACACAAAACTATACGAGATGTTGGG
ATTGCTTATATTTAATCACTAGTGAATTCGCGGCCGCCTGCAGGTCGACCATATGGGAGAGCTCCCAACGCGTTGGATGCATAGCTTG
AGTATTCTATAGTGTCACCTAAATAGCTTGGCGTAATCATGGTCATAGCTGTTTCCTGTGTGAAATTGTTATCCGCTCACAATTCCAC
ACAACATACGAGCCGGAAGCATAAAGTGTAAAGCCTGGGGTGCCTAATGAGTGAGCTAACTCACATTAATTGCGTTGCGCTCACTGCC
CGCTTTCCAGTCGGGAAACCTGTCGTGCCAGCTGCATTAATGAATCGGCCAACGCGCGGGGAGAGGCGGTTTGCGTATTGAGCGCTCT
TCCGCTTCCTCGCTCACTGACTCGCTGCGCTCGGTCGTTCGGCTGCGGCGAGCGGTATCAGCTCACTCNNNGGCGGTAATACNGNNNN
CCACANANTCNNGGNNNAACGCAGAAANANNNTGTGANCANNNNCCAGCAAAANNNNNNNNNGNANANGCNNCNNNNNCNGNGNNNN
TTTTTNCNANNMN
```

LFASTA compares two sequences v2.1u00 Mar, 2001
Please cite:
W. R. Pearson & D. J. Lipman PNAS (1988) 85: 2444-2448 searching /tmp/tmpweb/analseq/a1851590/s2 library Comparison of:
(A) S45T9
(B) S55M1 using matrix file DNA 94.952% identity in 931 nt overlap; init: 2030, opt: 4151 DONT 450 NUCLEOTIDES HORS VECTEUR FIG. 18
S55T9 (SEQ ID NO: 173) M13 REVERSE 700 pb

```
NNNNNNNNNNGNNNNNGNNGCNTGGCGGCCGCGGGATTCGATTAAATATAAGCAATCCCAACACTTTGGGGGGTGAGGCGGACAGATC
ACTTGAGGTCAGGGGTTTGAGACCAGCATGGCCAACGTGGTGAAAACTCAACTACTCAAAATAGAAAAATTAGCTGGACATGGTGGCA
CAGACCTGTGAAGCCAGCTACTCAGGAGGCTGAAGCATGAGAATTGCTTGAACCCTGGAGATGGAGGTTACAGTGAGCCCACGTCGCG
TCCCTGCACGCAAGCCTAGGCAAGAAAGCAAGACCGTGTCTCAAAAAAAGAAAAGAGATGCTGATACATGCTACAACATAGATGAACC
TTGAGGACATTATTCTAAGTGAAATGAGCTTGTCACAAAAGAACAAATATTGCATGATTCCAGTTATATGAGGTGCCCATAGTTGTCA
AATTCACAAAGACAAAAGTGGCATGGTCGTTACCAAGGGCTGGGAGAAAAGAGGAATGGTGAGTTAGTGTTTAATTGGTACAGAGTT
TCAGTTTTGCAAGATGAAAAGAGTTCTGGAGATGAATGTTGGGATTGCTTATATTTAATCACTAGTGAATTCGCGGCCGCCTGCAGGT
```

-continued
```
CGACCATATGGGAGAGCTCCCAACGCGTTGGATGCATAGCTTGAGTATTCTATAGTGTCACCTAAATAGCTTGGCGTAATCATGGTCA
TAGCTGTTTCCTGTGTGAAATTGTTATCCGCTCACAATTCCACACAACATACGAGCCGGAAGCATAAAGTGTAAAGCCTGGGGTGCCT
AATGAGTGAGCTAACTCACATTAANTTGCGTTGCGCTCACTGCCCGCTTTCCAGTCGGGAAACCTGTCGTGNCNAGCTGCATTAANGA
ATCNGNCCNNNCGCGGGGNNNNGCNNNNNCGTNNNNNNNNNNNTCGNNTTNNNNNNNNNNNNANTCNNNNNNNNNNNNNNCNNNNNNNNNNN
NNNNNNNNNNNNNGNNNNNNNNNN Comparison of:
-seq s55T9                                                  -1000 nt
70.9% identity in 891 nt overlap; score: 1973 E(10,000): 4.9e-156
(FIG. 10 suite)

Les différents clones ont une séquence de 450 pb en commun

Clone              B2(SEQ ID NO: 174)bando              à              400              pb
NNNNNNNNCNNCNNNNNANNGNANNNCNACTCACTNNAGGGCGAATTGGGCCCGACGTCGCATGCTCCCGGCCGNNANNNNGGCCGCGG
GAATTCGATTAAATATAAGCAATCCCAACACTTTGGGAGGCCGAGGCGGGCGGATCACGAGGTCAGGAGATGGAGACCATCCTGGCTA
ACACAGTGAAACCCTGTCTCTACTGAAAATACAAAAAAGTAGCCGGGCGTGGCGGCAGGCGCCTGTAGTCCCAGCTACTCAGGAGGCT
GAGGCAGGAGAATGGCATGAACCCAGGAGGCAGAGCTTGCAGTGAGCGAGATTGTGCCACTCCAGCCTGGGCAACAGAGCGA
GACTCCATCTCAAAAAAAAAAAAAAATCACCCCAAAGCAATAAGGAGAACTAGAACAGGACATACACTCCAACACTGGTGAAACTAGG
AAAACATATGTAACCCCAAACCACAATATATACACACAAAACTATACGAGATGTTGGGATTGCTTATATTTAATCACTAGTGAATTCG
CGGCCGCCTGCAGGTCGACCATATGGGAGAGCTCCCAACGCGTTGGATGCATACCTTGAGTATTCTATAGTGTCACCTAAATAGCTTG
GCGTAATCATGGTCATAGCTGTTTCCTGTGTGAAATTGTTATCCGCTCACAATTCCACACAACATACGAGCCGGAAGCATAAAGTGTA
AAGCCTGNNGGTGCCTAATGAGTGAGCTAACTCACATTAATTGCGTTGCGCTCACTGCCCGCTTTCCAGTCGGGAAACCTGTCGTGCCA
GCTGCNTTAATGAATCGGCCAACGCGCGGNNNAGGCGGNTTGCGTATNGNNNGCTCNNCNGCTTCCTCGCTCACTGACTCGCNNCNCN
CGGNCNNNCGGCTGCNGNGANNNNNTCANNTCNNNCNAAGGNNGNNANTANNNNANNNNNNNNNANNNNNGGGGAATANANCGNCNNN
NNANNNNNNNNNNN (A) B2
(B) S55M1

94.632% identity in 857 nt overlap; init: 3634, opt: 3955

FIG. 18

Clone C8 (SEQ ID NO: 127) 1400 pb:

NNNNNNNNNNNNNNTATAGATACTCAGCTATGCATCNACGCGTTGCGAGCTCTCCCATATGGNCNNNNNNNNGGCGGCCGCGAATTCA
CTAGTGATTTCCTATGCTTGACTATTAGCTCCTTTTCTTTACCTATTATTATTATTTATTTTTCAGATGGAGTCTCAGACTGTCGCCA
GGCTGGAGTACAGTGGCGCCATCTCGGCTCACTGAACCCTCCACCTACCGGGTTCAAGTGATTCTACTGCCGCAGTCTCCAGAGTAGC
TGGGACTACAGGCATGCACTACCACACCCAGCTAATTTTTTGTATTTTTAGTTGAGATGGGGTTTCACCATGATGGCCAGGATGGTCT
CGATCTCTTGACCTCATGATCTGCCTGCCTCAGCCTCCCAAAGTGCTGGGATTACGGGCATGAGCCACTGTGCTAGGCCTACCTATTT
TAAAAATAACAAGAATTCATCCAATGGAACGCTGAAATGCCTGTGGAGGATACAAGATTAATCAGCAGGATTATATTTGCCTATGACT
CCATTAATTCAATTCCAGACCCTACTTATGGGTCTAATGTCCTTTATTAGGCAATGTAGGAGATTCCTATACTCCTAATAAAGTAATC
TTTTTCCATTTAAATATCTTTGCTTTTTATCAGGCAGTATGTATTTCCACAAAGTTAATTCAATGAAATACACCTAAAGCTGAGAGTC
TTATCTCGTTAATGAATGAAAAATAGAAATCAATTATTCTGAGATGAGATTCTTCCTATAATTTTTATTAGTTGTTGTGAAATNNNCA
TGGGTTTGTCTTGANANATGATGATGTATTAATTCTNAATATTGNANTAAATGNCTCTGNAGTANAGATGACTCTNNTTTNNTCATGG
NNNNNACNNNNNTTGNNNANNNGCATTGNNNNNTGNANGNNNNNGTNNNNNNNTNNNNNNNNNNNNNNATTTNCANNNNNNAAANNNCN
CNNNNNNGNANNNNNNNCN
```

Results:

Clone B2, the band which is approximately 400 bp is the same fragment as S55M1, which itself is the same fragment as S45T9. These fragments are approximately between 400 and 450 bp. This is not surprising since they were obtained after a nested PCR carried out with the splicing reverse primer and the A1 primer (for the B2 fragment) and the ATG galgal primer for the S45T9 and S55M1 fragments. These fragments were obtained with RTs carried out at various temperatures. On the other hand, the S55T9 fragment is nevertheless approximately 600 bp, and a part (300 bp) exhibits quite strong identity with the other fragments cloned.

Example 6

From the cloning of the LIV21 gene described above, the new sequences are studied in order to design the most specific and effective siRNAs (ie. listing of siRNAs and FIG. 19) for creating "silencing" of the gene, i.e. inhibiting its expression. In the knowledge that the effect of the inhibition at each injection of siRNA remains short, i.e. most commonly less than one hour, the inventor has developed diagnostic products and therapeutic products from this same tool, namely the siRNA.

Example 6.1

The inventor uses siRNAs labelled with rhodamine or fluorescein or any other label that can be revealed and followed by optical observation with a microscope in order to localize the site, in the cells, tissues or sample labelled, that the labelled siRNA will go to in order to attach to the specific sequence which characterizes it, and thus to indicate the site of the expression of the messenger RNA of the gene of interest. Thus, the specific siRNA can be used as a diagnostic marker as an antibody would be, and can make it possible to localize, in a specific case such as on extemporaneous samples or any other type of sample taken from a patient, for example a cancerous tissue sample, the fluorescence or any other labelling used on the siRNA and found in a cell compartment on the sample.

Thus, a labelled siRNA of LIV21 (FIG. 19) that is found, under a microscope, in the cell nuclei at the periphery of a surgical exeresis, would indicate a diagnosis of complete exeresis of the cancerous tissue; on the other hand, this same marker found in the cytoplasm or the membranes of this same sample would mean that the surgeon would have to perform an enlarged exeresis, immediately if this test can be carried out directly in the operating theatre, which would be the best situation for removing all the cancer cells visible only on this molecular and cellular scale by virtue is the siRNA marker.

This could be a more rapid implementation alternative than the other application that the inventor has developed with the antibody or the LIV21 peptide, which can be used in the same manner.

Example 6.2 for therapeutic products, the inventor uses first labelled siRNAs of the Liv21 complex in order to evidence their expected presence in the cellular compartment and to visualize them. Then the inventor will use non-labelled Liv21 siRNAs solely for their therapeutic role. In a specific case, the injection of siRNA (FIG. 19) directly in a neurodegenerating tissue or any other mean of administration allowing to the siRNA to get to the neurodegenerating tissue (for example the ear, the eye, cephalorachidian liquid, etc. . . . ) and to act allowing proliferation until apoptosis and therefore the death of the neurodegenerating cell.

Example 7

Pharmaco-diagnostic Test

Based on the observations that follow in annex at the end of the description of the example concerning the properties of the Liv21 complex, the inventor conceived a design for a pharmacodiagnostic test clinically applicable by known technologically means, which can differ according to users and correspond for each mean to a new product. The invention consists in the fabrication of diagnostic DNA, protein and antibody arrays, including the antibodies already known for the different proteins of the complex associated with Liv21 according to the phase of the cell cycle, that is the antibodies, peptides or nucleotide sequences of the following genes: RBP2, E2F4, E2F1, SUMO, INT2, CRB2, HDAC1, TGF-beta, integrin_alpha5 beta2, Myob, MyoD, cycE/cdk2, cdk1, chk1, chk2, TNFalpha, CREB1 and p300, Rb, p107, p130 from the pocket protein family. But also NFkB, cdc2A, mdm2, p21, p53, p65, RAS, Ki67, CAF1. The protein arrays (FIG. 20) will allow the study of over or under expression of the gene products, the protein interactions and the post-translational modifications, more particularly phosphorylations and methylations of certain proteins, which indicate a specific state of the unhealthy cell that is different form the protein interactions and the metabolism of an healthy cell. The expression and silencing state of certain genes is different. The combined analysis of the results of over and under expression of the DNA and protein arrays will allow the best therapeutic targeting.

Example 7.1 pharmacodiagnostic biochip (FIG. 20) conceived based on nucleotide or peptide sequences fixed on classical supports and according to known techniques such as Agilent or Affymetrix or Caliper without restriction thereof and corresponding to known sequences of following genes and proteins listed in the patent, preferably using sequences that, by 3D analysis, show preferably a loop or helix-loop-helix or basic loop or zinc finger 3D structure or a 3D conformation similar to an helix corresponding in most cases to functional sites, or nucleotide sequences corresponding to a region of cysteine methylation, methylation of the promoter region of the gene inducing a potential silencing (see general bibliography), as well as new sequences of Liv21 listed in the description and in annex, but also sequences common to certain genes and certain virus thought to be implicated in particular in breast cancer of Chinese population:

| Mdm2 and HIV1 | |
|---|---|
| GAVTSSSNIAA | (SEQ ID NO: 197) |
| DLDQSV | (SEQ ID NO: 198) |
| EGF and HPV16 | |
| EWWRLD | (SEQ ID NO: 199) |
| KNSLD | (SEQ ID NO: 200) |
| MHIESLDS | (SEQ ID NO: 201) |

These sequences may be tested by microfluidic techniques upon fixation on a gold coverslip in order to study the protein interactions with the cell extracts of the patient.

Example 7.2 microfluidic test, for example Biacore, using the SPR technique known by those skilled in the art based on a support fixed with a gold film, which allows, once the light beam has been sent to the interface, to obtain an adsorbed energy as a function of the presence and the size of protein complexes (in the case of protein protein or protein antibody interactions) or of protein DNA complexes (in the case of protein DNA interactions) or of protein peptide complexes and an evanescent wave perpendicular to the interface axis. The inventor fixes the selected peptide or DNA sequences on gold particles and calculates the rU number as a function of the size of molecules cited in this patent for each interaction complex studied. In microfluidic, the liquid flowing over these gold film arrays may be a cell extract (or a selective one, meaning that it is only made of cell nuclei, or solely cell cytoplasms or solely cytoskeletal proteins etc. . . . ) according to extraction, separation and fractionation techniques such as Calbiochem: subcellular proteome extraction or tissue or cell extracts without any other preparation than anti-proteases or serum issued from a patient sample in order to study the circling marker (i.e. described nucleotide or peptide sequence list and/or known sequences of genes involved in the proliferation cycle listed).

Example 8

Study of the Expression of LIV21 in Breast Cancer Biopsies and Colon Cancer Biopsies In order to determine whether the observations obtained above are applicable to human tissues, a large number of cancer biopsies obtained from patients were studied by immunohistochemical reaction with LIV21-complex specific antibodies. The immunohistochemical determination of LIV21 protein expression was carried out on several biopsies from patients. Moreover, some paraffin slides from patients suffering from bladder cancer and from breast cancer were also studied.

Immunocytochemical Analysis Protocol:
Deparaffinize the slides.
Rehydrate the tissues.
Saturate the nonspecific sites and permeabilize the membranes.
Add the antibody in a humid chamber.
Reveal the antibody.
Deparaffinize the slides under a hood.

Two successive baths of toluene (rectapur Prolabo) 2×30 min or 2×20 min; then dehydrate the tissues with rectapur alcohol at 100% for 15 min; then rectapur ethanol at 95% for 10 min; then rectapur 70% for a further 10 min.

Thaw the antibody at the same time.

Rehydrate the tissues gently in PBS supplemented with 10% fetal calf serum and 0.1% Triton.

Saturate the nonspecific sites (for example, with ovalbumin) and permeabilize the membranes.

Rehydrate for one hour.

Deposit one ml of this "PBS" per section in order to cover the slide without it drying out at any moment (when it is a slide with cells and not tissues, half an hour is sufficient).

Place the pane and the stainless steel cover and water below so as to create a humid chamber.

Add the antibody in the humid chamber.

Dilute the rabbit serum to 1/200 in 4 ml of PBS triton, so as to continue to permeabilize the membranes, and FCS.

Place 1 ml on each slide and keep away from the light and avoid evaporation. Leave overnight or for a minimum of three hours.

Then rinse with 1× normal PBS pH 7, carry out two washes of 5 to 10 min so that no trace of the first antibody remains.

While preparing the Alexa 488 green probe (in the cold at 4° and in the dark) diluted to 1/250, therefore 10 μliter in 2.5 ml of PBS, still with 10% FCS and 0.1% Triton, rest the slides on the plate. Cover the section again with 2.5 ml in order to maintain a humid chamber for one hour, and then wash with 1×PBS, pH 7.

Wash with propidium iodide at 0.5 microgram per microliter to be diluted to 20 microgram per ml and then again to 1/50, but this time, diluted in 1×PBS alone (50 microliters per 2.5 ml of PBS). Drain while taking them out of the PBS and then dispense 2.5 ml of propidium iodide over the four slides for one minute, followed by two rinses with simple PBS. Mount the slides in Moviol before reading.

For an immunolabeling with peroxidase it is mandatory to mask the antigenic sites by a 20 minutes water bath step in order to obtain meaningful results when one is working with paraffined coverslips.

All the results are summarized in Table 1 below.

FIG. 23: Expression of Liv21 protein defined by immunohisto Chemical in biopsy of cancer colon and biopsy of health tissues.

These results show that the cytoplasmic localization of LIV21 is an indicator of the aggressiveness and of the metastatic potential of the cancer. The detection of LIV21 expression indicates the presence of invasive, aggressive and metastatic cancer cells. These results also show that the nuclear localization of LIV21 is an indicator of normal quiescent cells, that is of well-differentiated tissues.

Annex: Study of the Nuclear Translocation of LIV21 in MCF-7 Cells

The study of the subcellular distribution of LIV21 in different tumor lines of various origins showed an exclusively cytoplasmic localization of this protein.

The presence of putative phosphorylation sites by protein kinases C (PKCs) in the Liv21 sequence directed the study toward a involvement of these proteins with respect to its nuclear translocation. The MCF-7 line treated with TPA modulates PKCs and is used in the present study.

The Effect of TPA on the MCF-7 Line

TPA is a known activator of PKCs. It activates the growth of normal breast cells, does not modify the proliferation of the cells of benign tumors from this same tissue, but drastically inhibits the proliferation of the cells of human mammary tumor lines such as the MCF-7 line. It reduces the cell growth of this line by positively controlling the c-erb-2 receptor and negatively controlling the retinoic acid receptor α, which are both expressed in particularly large amount in these cells. The TPA greatly and rapidly inhibits the expression and the function of estrogen receptors (ERs) and it induces the time- and dose-dependent translocation of protein kinases C (PKCs) from the cytosol to the membranes.

Furthermore, TPA increases the migratory capacity of MCF-7 cells in vitro and a short period of treatment of these cells with TPA induces cellular expansion and microtubule organization characteristic of their differentiation.

Expression of LIV21 in MCF-7 Cells

Firstly, the inventor verified the expression of LIV21 in these cells at the transcriptional level and at the protein level.

The expression of the LIV21 mRNA was demonstrated by RT PCR (sense primer: (CCTGACATCCCTACATCAC-CCAT) (SEQ ID No 3) and antisense primer: TCCTATGCT-TGACTATTGC (SEQ ID No 4) in these cells compared with the cells from breast tissues (FIG. 2A). An mRNA of the same size as the mRNA detected in the breast tissues and specific for LIV21 was detected. However, the level of expression of LIV21 in the MCF 7 cells is lower than in the breast tissues. This first result shows that the MCF 7 line expresses the LIV21 mRNA.

The inventor tackled the study of the expression of the LIV21 protein through the Western blotting technique, with an anti-LIV21 antibody, in MCF-7 cells compared with mammary tissues.

The anti-LIV21 antibodies were obtained by the method described below. In this line, LIV21 is expressed, both in the mammary tissues and in the MCF-7 cells, in the form of a doublet which migrates at an apparent molecular weight of 50 kDa.

Production of Purified Anti-LIV21 Serum

The specific peptide sequences are the sequences No. 1 and No. 2.

These peptides were injected into rabbits (NZ W ESD 75 female, 2.3 kg at day 0), in agreement with standard immunization procedures, such as:

The Effect of TPA in MCF-7 Cells

It has been described in the literature that TPA induces the arrest of proliferation and the differentiation of tumor cells of the MCF-7 line. After three days of treatment, the control cultures have twice as many cells as the treated cultures. TPA at a concentration of 25 nM therefore clearly inhibits the proliferation.

In parallel, the TPA-treated cells rapidly acquire characteristics of differentiated mammary gland cells: hypertrophy, membrane protrusions and tendency to dissociate from one another. However, in the period of time over which the cells were studied, the secretory phenotype (appearance of granules and of secretory canaliculi) was not observed.

The Effect of TPA on the Liv21 Nuclear Localization

The expression of Liv21 in nuclear extracts studied and prepared after 12 h, 24 h, 48 h and 72 h of TPA treatment.

During

These kinetics, maximum anti-Liv21 immunoreactivity was observed from 12 h, was maintained up to 48 h and returned to its initial intensity after 72 h of treatment.

The immunoreactivity of Liv21 significantly increases at 12 h, at which time the number of cells in the S phase is minimal. It lasts until the reinitiation of the cell cycle observed at 72 h.

The results of the immunocytochemical study carried out using an anti-Liv21 antibody show that the nuclear translocation of Liv21 is at a maximum at 12 h and the localization of Liv21 is predominantly cytoplasmic at 72 h, which is in agreement with the Western blotting observations. However, it is interesting to note that the expression of Liv21 already begins from 1 h of treatment in certain cells, since they are not synchronous.

All these observations show that the nuclear translocation of Liv21 is concurrent with the decrease in the number of cells in the S phase.

Study of the Influence of PKCs on the Nuclear Translocation of LIV21

Effect of TPA on PKCε Expression

Western blotting study: Given that the protein sequence of LIV21 has putative PKC phosphorylation sites, including two specific for PKCε, the inventor tested the variation in the expression of this PKC as a function of the duration of TPA treatment. It was observed that TPA acts very rapidly on PKCε expression, which decreases from 30 min. The expression of PKCzeta (PKCζ) is used as an internal control since it is not sensitive to TPA.

The effect of the selective inhibition of the activity of PKCε on the nuclear translocation of LIV21 was studied by immunocytochemistry. These experiments were carried out on non-treated cultures or cultures treated for 12 h with TPA at 25 nM or with the peptide at two different concentrations, 1 and 2 μM. The peptide used at the concentration of 2 μM has an effect identical to that of TPA on the nuclear translocation of LIV21.

These results were supported by cell fractionation experiments on cultures treated with the PKCε-inhibiting peptide at 2 μM, compared with TPA-treated cultures. The same LIV21 expression profile was observed in the form of a doublet in the cytoplasm and of a single band in the nuclear fraction.

Example

Western Blotting Analysis

This example describes the conditions used for a Western blotting analysis of cancerous breast cells.

The protein extracts are heated at 80° C. for 5 minutes in a Laemmli buffer (pH 7.4, 0.06 M Tris, 3% SDS, 10% glycerol, 1 mM PMSF, β-mercaptoethanol). The migration is carried out by SDS-PAGE (sodium dodecyl sulfate-polyacrylamide gel electrophoresis). 10 to 20 μg of proteins migrate in a 12% polyacrylamide gel for 1 h under denaturing conditions (migration buffer: 25 mM Tris base, 192 mM glycine, 1% SDS, pH 8.3). The proteins are then transferred onto a nitrocellulose membrane (Schleicher & Schuell) for one hour by liquid transfer, in a transfer membrane (25 mM Tris, 192 mM glycine, 20% methanol, pH 8.3). The membranes, saturated in PBS-0.1% Tween-0.1% Triton X100-5% skimmed milk for one hour, are brought into contact with the primary antibody diluted in PBS-0.1% Tween-0.1% Triton X100-1% milk at ambient temperature with gentle agitation for one hour to two hours. After washing, the peroxidase-coupled secondary antibody is incubated with the membranes for 1 h. Revelation is carried out by means of a chemiluminescence reaction using the ECL kit according to the supplier's protocol (Amersham).

The primary antibodies used are:

The anti-LIV21 serum which was produced using two synthetic peptides based on the sequence of LIV21: peptide LIV21a (SEQ ID No 1) and peptide LIV21b (SEQ ID No 2) and/or peptide Liv21e (SEQ ID No 51). The peptides were coupled to hemocyanin before being injected into rabbits for the immunization. The polyclonal antibody was obtained from these two peptides by having immunized two rabbits and having bled one rabbit so as to have a preimmune serum (in order to be sure that this antibody did not already exist in this rabbit).

The rabbit anti-CDK2 polyclonal antibody (Santa-Cruz technology sc-163) diluted to 1/200.

The mouse anti-p21 monoclonal antibody (Dako, M7202) diluted to 1/150.

The mouse anti-p27 monoclonal antibody (Santa-Cruz technology sc-1641) diluted to 1/100.

Antitumor role of PML bodies: At the proliferation stage, there are visualized modifications in the PML bodies since these PML bodies dissociate and degrade: (speckles), proteins then become available in the nucleus for ensuring transcription, proliferation, immune reactions and everything that is required for gene transcription. It has been shown that PML associates with SUMO and with HDAC-1 (histone deacetylase 1) and that its complex acts on the expression of E2F1 and PML thus acts on the arrest of proliferation by blocking E2F1. Thus, the PML/HDAC-1 complex down-regulates E2F1 expression. PML associated with Rb (p130) binds to the deacetylated histones and blocks E2F1 by binding to the chromatin.

In acute promyelocytic leukemias, PML is truncated and becomes a fusion protein with the retinoic acid receptor. This fusion protein (PMLRARalpha) is due to a 15/17 chromosomal translocation. A new treatment for this disease by combining arsenic and retinoic acid in order to induce cancer cells into apoptosis has been reported in the literature. The PML protein is thought to regulate proliferation in cancers and lymphomas. The inventor has shown, by immunoprecipitation, the association SUMO-PML in which LIV21 is located.

In the above patents, it was shown that LIV21 is phosphorylated by PKCε. The TPA-treated MCF-7 lines show an inhibition of cancerous proliferation and a cell differentiation, and LIV21 is translocated into the nucleus. If a PKCε-specific inhibitory peptide was used, it was the activity and not the expression of PKCε which was inhibited.

During this TPA treatment (25 nM), when E2F4, p130 and LIV21 were studied (green fluorescence) in the nuclei labelled (DNA) with propidium iodide (red fluorescence), the following were observed:

After 12 h, intranuclear green fluorescence signals with the same pattern for E2F4, p130 and LIV21;

After 48 h, when the proliferation begins, E2F4 has a comparable localization; but at 72 h, it disappears from the nucleus (to the benefit of E2F1).

By observing, by double labelling, the colocalization of PML and of LIV21 at 24 h of TPA treatment (cf. merge: yellow fluorescence), it was observed that they are colocalized in the nuclei. At 48 h, the colocalization between LIV21 and SUMO ie. The hypothesis is that SUMO, which binds to LIV21, in fact targets LIV21 into the PML bodies and that LIV21 is involved in the PML/SUMO/Rb/HDAC-1 complexes. LIV21 is physically associated with PML and SUMO in the nuclear bodies, by immunoprecipitation and by colocalization by immunocytochemistry (Rb, p130 and p107 are pocket proteins which have the same binding site). The Rb proteins repress cell growth (Fabbro, Regazzi R, Bioch Biophys Res Comm 1986 Feb. 2; 135 (1): 65-73).

Physical Interaction of LIV21 with the Proteins of the E2F Family

Coimmunoprecipitation experiments carried out using anti-LIV21, anti-E2F1 and anti-E2F4 antibodies made it possible to demonstrate that LIV21 associates with E2F4.

The members of the E2F family are transcription factors whose role has been widely described in the literature as being key molecules in the positive or negative control of the cell cycle (Slansky J E and Farnham P J 1996; Helin K 1998 and Yamasaki L, 1998), by virtue of their association with the pRb protein (Wu C L, Zukerberg L R, Lees J A 1995) or pocket proteins. E2F1 positively controls the cell cycle by transactivating the promoter of the genes responsible for cell proliferation (DNA polymerase alpha, thymidine kinase, DHFR, etc.), whereas E2F4 is described as one of the members of the EF family which negatively controls the cycle. Furthermore, a high expression of E2F1 in embryonic mammary tissues has been shown (Espanel X, Gillet G 1998), whereas it is no longer expressed in post-mitotic mammary tissues, to the benefit of a large increase in E2F4 expression (Kastner A Brun G 1998).

The identification of antigens has been carried out in cell lysates by immunoprecipitation. The analysis of the physical interaction of various proteins associated with E2F4 and E2F1 was demonstrated by coimmunoprecipitation of protein complexes. The complex was studied using μ MACS PROTEIN with MICROBEADS (MILTENYIBIOTEC). When lysates of S. aureus are added, the proteins A interact with the Fc portion of the specific antibodies and the immunocomplexes become insoluble and are therefore recovered by centrifugation. After breaking of the bonds (heating) between AG/AC and protein A-rich membranes, Western blotting was carried out. These results suggest that the LIV21/E2F4 complex appears to play an important Role in establishing cell quiescence. A study of co immunoprecipitation is following also with the profound mammalian kit Pierce.

Functional Interaction of LIV21 with the Proteins of the E2F Family

It was demonstrated that blocking the expression of the LIV21 protein was correlated with a decrease in the expression of E2F4 and with an increase in the expression of E2F1. In parallel, the functional aspect of the increase in E2F1 was verified by studying the transcription of two of its target genes, DHFR and DNA polymerase α.

In conclusion, these results suggest that the LIV21/E2F4 complex acts as a complex which inhibits the expression of the E2F1 gene. This complex could correspond to a new point of control in the arrest of cell proliferation.

References

Arya R, Kedar V, Hwang J R, McDonough H, Li H H, Taylor J, Patterson C. Muscle ring finger protein-1 inhibits PKC{epsilon} activation and prevents cardiomyocyte hypertrophy. J. Cell Biol. 2004 Dec. 20; 167(6): 1147-59. Epub 2004 Dec. 13.

Caroll J S, Prall O W J, Musgrove E A, Sutherland R L. A pure Estrogen Antagonist Inhibits Cyclin E-Cdk2 Activity in MCF-7 Breast Cancer Cells and Induces Accumulation of p130-B2F4 Complexes Characteristic of Quiescence. (2000) *J Biol. Chem*, 275 (49):38221-38559.

Chau B N, Wang J Y. Coordinated regulation of life and death by RB. (2003) *Nat Rev Cancer*, 3 (2): 130-8.

Cheng T, Scadden D T. Cell cycle entry of hematopoietic stem and progenitor cells controlled by distinct cyclin-dependent kinase inhibitors. (2002) *Int J Hematol*, 75 (5):460-5.

Classon M, Harlow E. The retnoblastoma tumour suppressor in development and cancer. (2002) *Nat Rev Cancer*, 2 (12): 910-7.

Coqueret O. Linking cyclins to transcriptional control. (2002) *Gene*, 299 (1-2): 35-55.

Crisanti P, Raguenez G, Blancher C, Neron B, Mamoune A, Omri B. Cloning and characterization of a novel transcription factor involved in cellular proliferation arrest: PATF. (2001) *Oncogene* 20: 5475-5483.

Durocher D, Taylor I A, Sarbassova D, Haire L F, Westcott S L, Jackson S P, Smerdon S J, Yaffe M B. The molecular basis of FHA domain: phosphopeptide binding specificity and implications for phospho-dependant signaling mechanisms. (2000) *Mol Cell*, 6 (5):1169-82.

Durocher D, Jackson S P. The FHA domain. (2002) *FEBS Lett*, 513 (1): 58-66.

Espanel X, Le Cam L, North S, Sardet C, Brun G, Gillet G. Regulation of E2F-1 gene expression in avian cells. (1998) *Oncogene*, 17 (5): 585-94.

Fraering, Wenjuan Ye, Michael S Wolfe. Purification and characterization of the Human J Secretase Complex (2004) *Biochemistry* 43: 9774-9789.

Han E K, Begenann M, Sganibato A, Soh J W, Doki Y, Xing W Q, Liu W, Weinstein I B. Increased expression of cyclin D1 in a murine mammary epithelial cell line induces p27kip1, inhibits growth, and enhances apoptosis. Cell Growth Differ. 1996 June; 7(6):699-710.

Harlow et al Antibodies: A laboratory Manual, CSH Press, 1988

He L Z, Merghoub T, Pandolfi P P. In vivo analysis of the molecular pathogenesis of acute promyelocytic leukemia in the mouse and its therapeutic implications. (1999) *Oncogene*, 18: 5278-5292.

Helin K. Regulation of cell proliferation by the E2F transcription factors. (1998) *Curr Opin Genet Dev*, 8 (1): 28-35.

Horman S, Galand P, Mosselmans R, Legros N, Leclercq G, Mairesse N. Changes in the phosphorylation status of the 27 kDa heat shock protein (HSP27) associated with the modulation of growth and/or differentiation in MCF-7 cells. (1997) *Cell Prolif*, 30 (1):21-35.

Hughes et al. Adaptor plasmids simplify the insertion of foreign DNA into helper-independent retroviral vector. (1987) *J. Virol* 61: 3004-3012

Kastner A, Espanel X, Brun G. Transient accumulation of retinoblastoma/E2F-1 protein complexes correlates with the onset of neuronal differentiation in the developing quail neural retina. (1998) *Cell Growth Differ*, 9 (10): 857-67.

Katalin F. Medzihradszky. Characterization of Protein N-Glycosylation. (2005) *Methods in Enzymology, vol* 405:116-138.

Kohler G, Milstein C. Continuous cultures of fused cells secreting antibody of predefined specificity. Nature. 1975 Aug. 7; 256(5517):495-7.

Lee W, Boo J H, Jung M W, Park S D, Kim Y H, Kim S U, Mook-Jung I. Amyloid beta peptide directly inhibits PKC activation. Mol Cell Neurosci. 2004 June; 26(2): 222-31

Mairesse N, Horman S, Mosselmans R, Galand P. Antisense inhibition of the 27 kDa heat shock protein production affects growth rate and cytoskeletal organization in MCF-7 cells. (1996) *Cell Biol Int*, 20 (3): 205-12.

Matunis M J. On the road to repair: PCNA encounters SUMO and ubiquitin modifications. (2002) *Mol Cell*, 10 (3): 441-2.

Melchior F, Hengst L. SUMO-1 and p53. (2002) *Cell Cycle*, 1(4): 245-9.

Mundle S D, Saberwal G. Evolving intricacies and implications of E2F1 regulation. (2003) *FASEB J*, 17 (6): 569-74.

Opalka B, Dickopp A, Kirch H C. Apoptotic genes in cancer therapy. (2002) *Cells Tissues Organs*, 172 (2): 126-32.

Pardo F S, Su M, Borek C. Cyclin D1 induced apoptosis maintains the integrity of the G1/S checkpoint following ionizing radiation irradiation. Somat Cell Mol Genet. 1996 March, 22(2):135-44.

Pawson T, Gish G D; Nash P. SH2 domains, interaction modules and cellular wiring. (2001) *Trends Cell Biol,* 11 (12): 504-11.

Platet N, Prevostel C, Derocq D, Joubert D, Rochefort H, Garcia M. Breast cancer cell invasiveness: correlation with protein kinase C activity and differential regulation by phorbol ester in estrogen receptor-positive and -negative cells. (1998) *Int J Cancer,* 75 (5): 750-6.

Ree A H, Bjornland K, Brunner N, Johansen H T, Pedersen K B, Aasen A O, Fodstad O. Regulation of tissue-degrading factors and in vitro invasiveness in progression of breast cancer cells. (1998) *Clin Exp Metastasis,* 16 (3): 205-15.

Regazzi R, Fabbro D, Costa S D, Bomer C, Eppenberger U. Effects of tumor promoters on growth and on cellular redistribution of phospholipid/$Ca^{2+}$-dependant protein kinase in human breast cancer cells. (1986) *Int J Cancer,* 37 (5): 731-737, Schneider S M, Offterdinger M, Huber H, Grunt T W. Involvement of nuclear steroid/thyroid/retinoid receptors and of protein kinases in the regulation of growth and of c-erbB and retinoic acid receptor expression in MCF-7 breast cancer cells. (1999) *Breast Cancer Res and Treat,* 58: 171-181.

Senderowicz A M. Cyclin-dependent kinases as targets for cancer therapy. (2002) *Cancer Chemother Biol Response Modif,* 20: 169-96.

Slansky J E and Fanham P J. Introduction to the E2F family: protein structure and gene regulation. (1996) *Curr Top Microbiol Immunol,* 53:347-360.

Songyang Z, Shoelson S E, Chaudhuri M, Gish G, Pawson T, Haser W G, King F, Roberts T, Ratnofsky S, Lechleider R J. SH2 domains recognize specific phosphopeptide sequences. (1993) Cell, 72 (5): 767-78.

Starzec A B., Spanakis E, Nehme A, Salle V, Veber N, Mainguene C, Planchon P, Valette A, Prevost G, Israel L. Proliferative responses of epithelial cells to 8-bromocyclic AMP and to a phorbol ester change during breast pathogenesis. (1994) *J Cell Physiol,* 161 (1): 31-8.

Stevaux O, Dyson N J. A revised picture of the E2F transcriptional network and RB function. (2002) *Curr Opin Cell Biol,* 14 (6): 684-91.

Stiegler P, Giordano A. The family of retinoblastoma proteins. (2001) *Crit Rev Eukaryot Gene Expr,* 11 (1-3): 59-76

Toma O, Weber N C, Wolter J I, Obal D, Preckel B, Schlack W. Desflurane preconditioning induces time-dependent activation of protein kinase C epsilon and extracellular signal-regulated kinase 1 and 2 in the rat heart in vivo. Anesthesiology. 2004 December; 101(6):1372-80.

Vaitukaitis J, Robbins J B, Nieschlag E, Ross G T. A method for producing specific antisera with small doses of immunogen. J Clin Endocrinol Metab. 1971 December; 33(6):988-91.

Ward E S, Gussow D, Griffiths A D, Jones P T, Winter G. Binding activities of a repertoire of single immunoglobulin variable domains secreted from *Escherichia coli*. Nature. 1989 Oct. 12; 341(6242):544-6.

Wu C L, Zukerberg L R, Ngwu C, Harlow E, Lees J A. In vivo association of E2F and DP family proteins. (1995) *Mol Cell Biol,* 15 (5):2536-46.

Yaffe M B. Phosphotyrosine-binding domains in signal transduction. (2002) *Nat Rev Mol Cell Biol,* 3 (3): 177-86.

Yamasaki L. Growth regulation by the E2F and DP transcription factor families. (1998) *Results Probl Cell Differ,* 22: 199-227.

Zee-Yong Park and David H. Russell. Identification of Individual Proteins in Complex Protein Mixtures by High-Resolution, High-Mass-Accuracy MALDI TOF-Mass Spectrometry Analysis of In-Solution Thermal denaturation/Enzymatic Digestion. (2001) *Anal Chem,* 73 (11): 2558-2564.

SEQUENCE LISTING

```
<160> NUMBER OF SEQ ID NOS: 188

<210> SEQ ID NO 1
<211> LENGTH: 12
<212> TYPE: PRT
<213> ORGANISM: Artificial Sequence
<220> FEATURE:
<223> OTHER INFORMATION: synthetic peptide; translation of a sequence of
      clone C18 and S55M1

<400> SEQUENCE: 1

Gln Ala Gly Val Gln Trp Arg Asn Leu Gly Ser Leu
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic peptide; translation of clone C18 and
      s55M1

<400> SEQUENCE: 2

Ser Leu Gln Ser Ser Trp Asp Tyr Arg Arg
1               5                   10
```

```
<210> SEQ ID NO 3
<211> LENGTH: 7
<212> TYPE: PRT
<213> ORGANISM: Artificial Sequence
<220> FEATURE:
<223> OTHER INFORMATION: synthetic peptide; translation of clone C8
      Frame 3

<400> SEQUENCE: 3

Phe Leu Tyr Phe Leu Arg Trp
1               5

<210> SEQ ID NO 4
<211> LENGTH: 15
<212> TYPE: PRT
<213> ORGANISM: Artificial Sequence
<220> FEATURE:
<223> OTHER INFORMATION: synthetic peptide; translation of clone C8
      Frame 3 (SEQ N 127)

<400> SEQUENCE: 4

Gly Phe Thr Met Met Ala Arg Met Val Ser Ile Ser Pro His Asp
1               5                   10                  15

<210> SEQ ID NO 5
<211> LENGTH: 20
<212> TYPE: PRT
<213> ORGANISM: Artificial Sequence
<220> FEATURE:
<223> OTHER INFORMATION: synthetic peptide; translation of clone S55M1
      (SEQ N 124) Reverse 2

<400> SEQUENCE: 5

Met Glu Ser Arg Ser Val Ala Gln Ala Gly Val Gln Trp Arg Asn Leu
1               5                   10                  15

Gly Ser Leu Gln
            20

<210> SEQ ID NO 6
<211> LENGTH: 11
<212> TYPE: PRT
<213> ORGANISM: Artificial Sequence
<220> FEATURE:
<223> OTHER INFORMATION: synthetic peptide; translation of clone S55M1
      Reverse 2

<400> SEQUENCE: 6

Pro Ala Ser Ala Ser Glu Ser Val Gly Ile Ala
1               5                   10

<210> SEQ ID NO 7
<211> LENGTH: 15
<212> TYPE: PRT
<213> ORGANISM: Artificial Sequence
<220> FEATURE:
<223> OTHER INFORMATION: synthetic peptide; translation of clone S55M1
      Reverse

<400> SEQUENCE: 7

Gly Phe Thr Val Leu Ala Arg Met Val Ser Ile Ser Pro Arg Asp
1               5                   10                  15

<210> SEQ ID NO 8
<211> LENGTH: 12
<212> TYPE: PRT
<213> ORGANISM: Artificial Sequence
<220> FEATURE:
```

```
<223> OTHER INFORMATION: synthetic peptide; translation of clone C8
      Frame 3

<400> SEQUENCE: 8

Pro Ala Ser Ala Ser Gln Ser Ala Gly Ile Thr Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: synthetic peptide; translation of clone S55M1
      Reverse 2

<400> SEQUENCE: 9

Arg Asp Pro Pro Ala Ser Ala Ser Gln Ser
1               5                   10

<210> SEQ ID NO 10
<211> LENGTH: 20
<212> TYPE: PRT
<213> ORGANISM: Artificial Sequence
<220> FEATURE:
<223> OTHER INFORMATION: synthetic peptide; translation of clone C8
      Frame 3

<400> SEQUENCE: 10

Met Ser His Cys Ala Arg Pro Thr Tyr Phe Lys Asn Asn Lys Asn Ser
1               5                   10                  15

Ser Asn Gly Thr
            20

<210> SEQ ID NO 11
<211> LENGTH: 21
<212> TYPE: PRT
<213> ORGANISM: Artificial Sequence
<220> FEATURE:
<223> OTHER INFORMATION: synthetic peptide; translation of clone C8
      Frame 3

<400> SEQUENCE: 11

Leu Lys Cys Leu Trp Arg Ile Gln Asp Ser Ala Gly Leu Tyr Leu Pro
1               5                   10                  15

Met Thr Pro Leu Ile
            20

<210> SEQ ID NO 12
<211> LENGTH: 16
<212> TYPE: PRT
<213> ORGANISM: Artificial Sequence
<220> FEATURE:
<223> OTHER INFORMATION: synthetic peptide; translation of clone C8
      Frame 3

<400> SEQUENCE: 12

Gln Phe Gln Thr Leu Leu Met Gly Leu Met Ser Phe Ile Arg Gln Cys
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: synthetic peptide; translation of clone C8
      Frame 3

<400> SEQUENCE: 13
```

```
Arg Arg Phe Leu Tyr Ser Ser Asn Leu Phe Pro Phe Lys Tyr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: synthetic peptide; synthesis of isoform of khs1
      domain

<400> SEQUENCE: 14

Arg Thr Val Arg Pro Leu Asn Ile Glu Val Gly Val Leu Pro Lys Thr
1               5                   10                  15

<210> SEQ ID NO 15
<211> LENGTH: 24
<212> TYPE: PRT
<213> ORGANISM: Artificial Sequence
<220> FEATURE:
<223> OTHER INFORMATION: synthetic peptide; synthesis of new isoform of
      Htatine 3 with C and not T

<400> SEQUENCE: 15

Lys Phe Phe Val Phe Ala Leu Ile Leu Ala Leu Met Leu Ser Met Cys
1               5                   10                  15

Gly Ala Asp Ser His Ala Lys Arg
            20

<210> SEQ ID NO 16
<211> LENGTH: 20
<212> TYPE: PRT
<213> ORGANISM: Artificial Sequence
<220> FEATURE:
<223> OTHER INFORMATION: synthetic peptide; synthesis of new isoform
      sequence of pRK11824 (polynucleotide phosphorylase)

<400> SEQUENCE: 16

Lys Gly Ile Thr Glu Glu Ile Met Glu Ile Ala Leu Gly Gln Ala Leu
1               5                   10                  15

Glu Ala Arg Leu
            20

<210> SEQ ID NO 17
<211> LENGTH: 21
<212> TYPE: PRT
<213> ORGANISM: Homo sapiens

<400> SEQUENCE: 17

Arg Ala Ile Cys Glu Glu Thr Lys Ala Ser Ile Asp Ile Glu Asp Asp
1               5                   10                  15

Gly Ser Ile Lys Ile
            20

<210> SEQ ID NO 18
<211> LENGTH: 23
<212> TYPE: PRT
<213> ORGANISM: Homo sapiens

<400> SEQUENCE: 18

Lys Val Thr Asp Ile Leu Lys Glu Gly Gln Glu Val Glu Val Leu Val
1               5                   10                  15

Leu Asp Val Asp Asn Arg Gly
            20
```

```
<210> SEQ ID NO 19
<211> LENGTH: 15
<212> TYPE: PRT
<213> ORGANISM: Homo sapiens

<400> SEQUENCE: 19

Lys Met Leu Thr Gly Val Asn Val Leu Ala Asp Ala Val Lys Ala
1               5                   10                  15

<210> SEQ ID NO 20
<211> LENGTH: 19
<212> TYPE: PRT
<213> ORGANISM: Homo sapiens

<400> SEQUENCE: 20

Arg Ala Ala Val Glu Glu Gly Val Val Pro Gly Gly Gly Val Ala Leu
1               5                   10                  15

Ile Arg Ala

<210> SEQ ID NO 21
<211> LENGTH: 14
<212> TYPE: PRT
<213> ORGANISM: Homo sapiens

<400> SEQUENCE: 21

Lys Val Ile Ile Val Ala Val Asp Trp Asp Leu Ser Lys Glu
1               5                   10

<210> SEQ ID NO 22
<211> LENGTH: 16
<212> TYPE: PRT
<213> ORGANISM: Homo sapiens

<400> SEQUENCE: 22

Lys Ile Phe Ser Pro Ala Thr Val Phe Phe Thr Ser Ile Glu Lys His
1               5                   10                  15

<210> SEQ ID NO 23
<211> LENGTH: 16
<212> TYPE: PRT
<213> ORGANISM: Homo sapiens

<400> SEQUENCE: 23

Lys Asn Val Trp Ile Leu Thr Gly Phe Gln Gln Gly Gln Glu Phe Pro
1               5                   10                  15

<210> SEQ ID NO 24
<211> LENGTH: 12
<212> TYPE: PRT
<213> ORGANISM: Homo sapiens

<400> SEQUENCE: 24

Arg Phe Asn Leu Phe Ala Gly Gly Ser Asn Lys Ala
1               5                   10

<210> SEQ ID NO 25
<211> LENGTH: 12
<212> TYPE: PRT
<213> ORGANISM: Homo sapiens

<400> SEQUENCE: 25

Arg Ala Tyr Ser Leu Leu Gly Thr Ser Glu Arg Thr
1               5                   10
```

```
<210> SEQ ID NO 26
<211> LENGTH: 12
<212> TYPE: PRT
<213> ORGANISM: Homo sapiens

<400> SEQUENCE: 26

Ala Met Ala Ala Asn Asp Thr Gly Gly Phe Val Lys
1               5                   10

<210> SEQ ID NO 27
<211> LENGTH: 11
<212> TYPE: PRT
<213> ORGANISM: Homo sapiens

<400> SEQUENCE: 27

Ala Ser Glu Glu Gly Ile Met Val Val Glu Arg
1               5                   10

<210> SEQ ID NO 28
<211> LENGTH: 18
<212> TYPE: PRT
<213> ORGANISM: Homo sapiens

<400> SEQUENCE: 28

Phe Asp Val Val Val Ile Gly Ala Gly Pro Gly Gly Tyr Val Ala Ala
1               5                   10                  15

Ile Lys

<210> SEQ ID NO 29
<211> LENGTH: 19
<212> TYPE: PRT
<213> ORGANISM: Homo sapiens

<400> SEQUENCE: 29

Arg Pro Val Thr Thr Asp Leu Leu Ala Ser Asp Ser Gly Val Thr Ile
1               5                   10                  15

Asp Glu Arg

<210> SEQ ID NO 30
<211> LENGTH: 7
<212> TYPE: PRT
<213> ORGANISM: Homo sapiens

<400> SEQUENCE: 30

Phe Tyr Cys Gly Trp Asp Arg
1               5

<210> SEQ ID NO 31
<211> LENGTH: 8
<212> TYPE: PRT
<213> ORGANISM: Homo sapiens

<400> SEQUENCE: 31

Asp Val Ala Gln Glu Glu Gly Lys
1               5

<210> SEQ ID NO 32
<211> LENGTH: 8
<212> TYPE: PRT
<213> ORGANISM: Homo sapiens

<400> SEQUENCE: 32

Ser Gly Ile Pro Ser Glu Leu Arg
1               5
```

```
<210> SEQ ID NO 33
<211> LENGTH: 7
<212> TYPE: PRT
<213> ORGANISM: Homo sapiens

<400> SEQUENCE: 33

Glu Ala His Ile Gln Met Lys
1               5

<210> SEQ ID NO 34
<211> LENGTH: 7
<212> TYPE: PRT
<213> ORGANISM: Homo sapiens

<400> SEQUENCE: 34

Glu Gly Ile Trp Ile Pro Lys
1               5

<210> SEQ ID NO 35
<211> LENGTH: 6
<212> TYPE: PRT
<213> ORGANISM: Homo sapiens

<400> SEQUENCE: 35

Tyr Thr Phe Asp Ser Arg
1               5

<210> SEQ ID NO 36
<211> LENGTH: 6
<212> TYPE: PRT
<213> ORGANISM: Homo sapiens

<400> SEQUENCE: 36

Leu Thr His Glu Ile Arg
1               5

<210> SEQ ID NO 37
<211> LENGTH: 5
<212> TYPE: PRT
<213> ORGANISM: Homo sapiens

<400> SEQUENCE: 37

Leu Tyr Leu Asp Lys
1               5

<210> SEQ ID NO 38
<211> LENGTH: 5
<212> TYPE: PRT
<213> ORGANISM: Homo sapiens

<400> SEQUENCE: 38

Tyr Gly Leu Gln Arg
1               5

<210> SEQ ID NO 39
<211> LENGTH: 5
<212> TYPE: PRT
<213> ORGANISM: Homo sapiens

<400> SEQUENCE: 39

Asp Ser Ile Ile Arg
1               5

<210> SEQ ID NO 40
<211> LENGTH: 16
```

```
<212> TYPE: PRT
<213> ORGANISM: Homo sapiens

<400> SEQUENCE: 40

Leu Glu Ala Ile Cys Ala Ala Met Ile Glu Ser Trp Gly Tyr Asp Lys
1               5                   10                  15

<210> SEQ ID NO 41
<211> LENGTH: 12
<212> TYPE: PRT
<213> ORGANISM: Homo sapiens

<400> SEQUENCE: 41

Gly Asp Leu Trp Phe Met Ser His Gln Gly His Lys
1               5                   10

<210> SEQ ID NO 42
<211> LENGTH: 11
<212> TYPE: PRT
<213> ORGANISM: Homo sapiens

<400> SEQUENCE: 42

Tyr Ala Phe Asp Phe Tyr Glu Met Thr Ser Arg
1               5                   10

<210> SEQ ID NO 43
<211> LENGTH: 14
<212> TYPE: PRT
<213> ORGANISM: Homo sapiens

<400> SEQUENCE: 43

Glu Val Asn Ala Gly Thr Ser Gly Thr Phe Ser Val Pro Arg
1               5                   10

<210> SEQ ID NO 44
<211> LENGTH: 9
<212> TYPE: PRT
<213> ORGANISM: Homo sapiens

<400> SEQUENCE: 44

Asn Gln Asp Arg Pro Tyr Met Pro Arg
1               5

<210> SEQ ID NO 45
<211> LENGTH: 9
<212> TYPE: PRT
<213> ORGANISM: Homo sapiens

<400> SEQUENCE: 45

Ile Val Ser Ile Leu Glu Trp Asp Arg
1               5

<210> SEQ ID NO 46
<211> LENGTH: 10
<212> TYPE: PRT
<213> ORGANISM: Homo sapiens

<400> SEQUENCE: 46

Ala Pro Tyr Ile Ala Glu Thr Ala Leu Arg
1               5                   10

<210> SEQ ID NO 47
<211> LENGTH: 9
<212> TYPE: PRT
<213> ORGANISM: Homo sapiens
```

<400> SEQUENCE: 47

Asn Met His Asn Leu Leu Gly Val Lys
1               5

<210> SEQ ID NO 48
<211> LENGTH: 9
<212> TYPE: PRT
<213> ORGANISM: Homo sapiens

<400> SEQUENCE: 48

Asn Leu Thr Asp Met Ser Leu Ala Arg
1               5

<210> SEQ ID NO 49
<211> LENGTH: 8
<212> TYPE: PRT
<213> ORGANISM: Homo sapiens

<400> SEQUENCE: 49

His Thr Thr Glu Asp Val Asn Arg
1               5

<210> SEQ ID NO 50
<211> LENGTH: 7
<212> TYPE: PRT
<213> ORGANISM: Homo sapiens

<400> SEQUENCE: 50

Lys Phe Phe Val Phe Ala Leu
1               5

<210> SEQ ID NO 51
<211> LENGTH: 15
<212> TYPE: PRT
<213> ORGANISM: Homo sapiens

<400> SEQUENCE: 51

Phe Val Phe Ala Leu Ile Leu Ala Leu Met Leu Ser Met Cys Gly
1               5                   10                  15

<210> SEQ ID NO 52
<211> LENGTH: 12
<212> TYPE: PRT
<213> ORGANISM: Homo sapiens

<400> SEQUENCE: 52

Thr Leu Gln Ile Phe Asn Ile Glu Met Lys Ser Lys
1               5                   10

<210> SEQ ID NO 53
<211> LENGTH: 17
<212> TYPE: PRT
<213> ORGANISM: Homo sapiens

<400> SEQUENCE: 53

Lys Asp Pro Glu Leu Trp Ala His Val Leu Glu Glu Thr Asn Thr Ser
1               5                   10                  15

Arg

<210> SEQ ID NO 54
<211> LENGTH: 12
<212> TYPE: PRT
<213> ORGANISM: Homo sapiens

<400> SEQUENCE: 54

Lys Ser Trp Glu Val Tyr Gln Gly Val Cys Gln Lys
1               5                   10

<210> SEQ ID NO 55
<211> LENGTH: 13
<212> TYPE: PRT
<213> ORGANISM: Homo sapiens

<400> SEQUENCE: 55

His Thr Ser Leu Val Gly Cys Gln Val Ile His Tyr Arg
1               5                   10

<210> SEQ ID NO 56
<211> LENGTH: 22
<212> TYPE: PRT
<213> ORGANISM: Homo sapiens

<400> SEQUENCE: 56

Cys Trp Thr Leu Ile Glu Ala Val Gly Ser Arg Ala Lys Lys Glu Ala
1               5                   10                  15

Ala Ala Glu Glu Ala Lys
            20

<210> SEQ ID NO 57
<211> LENGTH: 18
<212> TYPE: PRT
<213> ORGANISM: Homo sapiens

<400> SEQUENCE: 57

Met Leu Glu Arg Gly Ala Glu Ser Ala Ala Gly Ala Thr Asp Pro Ser
1               5                   10                  15

Pro Thr

<210> SEQ ID NO 58
<211> LENGTH: 27
<212> TYPE: PRT
<213> ORGANISM: Homo sapiens

<400> SEQUENCE: 58

Glu Ala Pro His Gln Gly Pro Pro Gln Lys Pro Ser Gln Ser Ala Pro
1               5                   10                  15

Gly Pro Thr Ala Ser Ala Gly Ser Pro Pro Arg
            20                  25

<210> SEQ ID NO 59
<211> LENGTH: 11
<212> TYPE: PRT
<213> ORGANISM: Homo sapiens

<400> SEQUENCE: 59

Arg Arg Arg Pro Pro Gln Arg Pro His Arg
1               5                   10

<210> SEQ ID NO 60
<211> LENGTH: 13
<212> TYPE: PRT
<213> ORGANISM: Homo sapiens

<400> SEQUENCE: 60

Cys Pro Asp Cys Asp Lys Ala Phe Ser Tyr Pro Ser Lys
1               5                   10

<210> SEQ ID NO 61

```
<211> LENGTH: 16
<212> TYPE: PRT
<213> ORGANISM: Homo sapiens

<400> SEQUENCE: 61

Leu Ala His Gly Gly Ala Arg Pro His Pro Cys Pro Asp Cys Pro Lys
1               5                   10                  15

<210> SEQ ID NO 62
<211> LENGTH: 19
<212> TYPE: PRT
<213> ORGANISM: Homo sapiens

<400> SEQUENCE: 62

Ser Lys Leu Ala Ala His Leu Trp Thr His Ala Pro Thr Arg Pro Tyr
1               5                   10                  15

Pro Cys Pro

<210> SEQ ID NO 63
<211> LENGTH: 17
<212> TYPE: PRT
<213> ORGANISM: Homo sapiens

<400> SEQUENCE: 63

Leu Ala Ala His Leu Trp Thr His Ala Pro Thr Arg Pro Tyr Pro Cys
1               5                   10                  15

Pro

<210> SEQ ID NO 64
<211> LENGTH: 13
<212> TYPE: PRT
<213> ORGANISM: Homo sapiens

<400> SEQUENCE: 64

Met Ala Gly Ser Gly Gly Leu Gly Gly Gly Ala Gly Gly
1               5                   10

<210> SEQ ID NO 65
<211> LENGTH: 13
<212> TYPE: PRT
<213> ORGANISM: Homo sapiens

<400> SEQUENCE: 65

Ala Ser Arg Ala Pro Met Leu Leu Val Ala Leu Val Leu
1               5                   10

<210> SEQ ID NO 66
<211> LENGTH: 13
<212> TYPE: PRT
<213> ORGANISM: Homo sapiens

<400> SEQUENCE: 66

Ala Pro Met Leu Leu Val Ala Leu Val Leu Gly Ala Tyr
1               5                   10

<210> SEQ ID NO 67
<211> LENGTH: 10
<212> TYPE: PRT
<213> ORGANISM: Homo sapiens

<400> SEQUENCE: 67

Thr Leu Asp Gly Gln Ile Thr Met Glu Lys
1               5                   10
```

```
<210> SEQ ID NO 68
<211> LENGTH: 30
<212> TYPE: PRT
<213> ORGANISM: Homo sapiens

<400> SEQUENCE: 68

Pro Thr Ser Leu His Pro Tyr Ile Pro Ala Ser Leu His Pro Tyr Ile
1               5                   10                  15

Pro Thr Ser Leu His Pro Tyr Ile Pro Ala Ser Leu His Pro
            20                  25                  30

<210> SEQ ID NO 69
<211> LENGTH: 10
<212> TYPE: PRT
<213> ORGANISM: Homo sapiens

<400> SEQUENCE: 69

Val Met Ala Asp Glu Leu Thr Asn Ser Arg
1               5                   10

<210> SEQ ID NO 70
<211> LENGTH: 11
<212> TYPE: PRT
<213> ORGANISM: Homo sapiens

<400> SEQUENCE: 70

Met Ser Ile Gln Cys Asp Val Trp Arg Ser Lys
1               5                   10

<210> SEQ ID NO 71
<211> LENGTH: 15
<212> TYPE: PRT
<213> ORGANISM: Homo sapiens

<400> SEQUENCE: 71

Gly Glu Phe Leu Gly Gln Ser Glu Gly Val Ile Glu Pro Asn Lys
1               5                   10                  15

<210> SEQ ID NO 72
<211> LENGTH: 15
<212> TYPE: PRT
<213> ORGANISM: Homo sapiens

<400> SEQUENCE: 72

Met Ala Glu Thr Val Leu Arg Ile Leu Asp Pro Val Thr Cys Lys
1               5                   10                  15

<210> SEQ ID NO 73
<211> LENGTH: 16
<212> TYPE: PRT
<213> ORGANISM: Homo sapiens

<400> SEQUENCE: 73

Leu Leu Val Ala Ser Val Gly Asp Asp Leu Gln Tyr His Phe Glu Arg
1               5                   10                  15

<210> SEQ ID NO 74
<211> LENGTH: 10
<212> TYPE: PRT
<213> ORGANISM: Homo sapiens

<400> SEQUENCE: 74

Ser Gln Gln Asn Arg Trp Ala Glu Ser Lys
1               5                   10
```

```
<210> SEQ ID NO 75
<211> LENGTH: 11
<212> TYPE: PRT
<213> ORGANISM: Homo sapiens

<400> SEQUENCE: 75

Met Asn Val Glu Lys Ala Glu Phe Cys Asn Lys
1               5                   10

<210> SEQ ID NO 76
<211> LENGTH: 16
<212> TYPE: PRT
<213> ORGANISM: Homo sapiens

<400> SEQUENCE: 76

Asn Ser Gln Gly Val Ala Trp Ile Thr Leu Asn Ser Ser Ile Gln Lys
1               5                   10                  15

<210> SEQ ID NO 77
<211> LENGTH: 17
<212> TYPE: PRT
<213> ORGANISM: Homo sapiens

<400> SEQUENCE: 77

Val Cys Thr Lys Pro Val Glu Ser Thr Ile Glu Asp Lys Ile Phe Gly
1               5                   10                  15

Lys

<210> SEQ ID NO 78
<211> LENGTH: 13
<212> TYPE: PRT
<213> ORGANISM: Homo sapiens

<400> SEQUENCE: 78

Ala Gly Leu Gln Glu Glu Ala Gln Gln Leu Arg Asp Glu
1               5                   10

<210> SEQ ID NO 79
<211> LENGTH: 11
<212> TYPE: PRT
<213> ORGANISM: Homo sapiens

<400> SEQUENCE: 79

Met Ser His Lys Gln Ile Tyr Tyr Ser Asp Lys
1               5                   10

<210> SEQ ID NO 80
<211> LENGTH: 15
<212> TYPE: PRT
<213> ORGANISM: Homo sapiens

<400> SEQUENCE: 80

Tyr Asp Asp Glu Glu Phe Glu Tyr Arg His Val Met Leu Pro Lys
1               5                   10                  15

<210> SEQ ID NO 81
<211> LENGTH: 14
<212> TYPE: PRT
<213> ORGANISM: Homo sapiens

<400> SEQUENCE: 81

Leu Val Pro Lys Thr His Leu Met Ser Glu Ser Glu Trp Arg
1               5                   10

<210> SEQ ID NO 82
```

```
<211> LENGTH: 21
<212> TYPE: PRT
<213> ORGANISM: Homo sapiens

<400> SEQUENCE: 82

Lys Ala Tyr Glu Cys Asp Ile Thr Tyr Gly Thr Asn Asn Glu Phe Gly
1               5                   10                  15

Phe Asp Tyr Leu Arg
            20

<210> SEQ ID NO 83
<211> LENGTH: 14
<212> TYPE: PRT
<213> ORGANISM: Homo sapiens

<400> SEQUENCE: 83

Thr Ile Met Ile Thr Glu Ala Gly Ile Ser Lys Ala Glu Lys
1               5                   10

<210> SEQ ID NO 84
<211> LENGTH: 13
<212> TYPE: PRT
<213> ORGANISM: Homo sapiens

<400> SEQUENCE: 84

Glu Arg Ala Val Glu Ser Asp Cys Tyr Ala Glu Gln Val
1               5                   10

<210> SEQ ID NO 85
<211> LENGTH: 17
<212> TYPE: PRT
<213> ORGANISM: Homo sapiens

<400> SEQUENCE: 85

Cys Val Ala Val Gly Gly His Ser Gly Ser Leu Leu Ile Gln His Val
1               5                   10                  15

Met

<210> SEQ ID NO 86
<211> LENGTH: 24
<212> TYPE: PRT
<213> ORGANISM: Homo sapiens

<400> SEQUENCE: 86

Ala Arg Trp Thr Phe Gly Gly Arg Asp Leu Pro Ala Glu Gln Pro Gly
1               5                   10                  15

Ser Phe Leu Tyr Asp Ala Arg Leu
            20

<210> SEQ ID NO 87
<211> LENGTH: 8
<212> TYPE: PRT
<213> ORGANISM: Homo sapiens

<400> SEQUENCE: 87

Ile Pro Gly Gly Phe Phe Lys Arg
1               5

<210> SEQ ID NO 88
<211> LENGTH: 13
<212> TYPE: PRT
<213> ORGANISM: Homo sapiens

<400> SEQUENCE: 88
```

```
Thr Val Arg Pro Leu Asn Ile Glu Val Gly Val Leu Pro
1               5                   10

<210> SEQ ID NO 89
<211> LENGTH: 13
<212> TYPE: PRT
<213> ORGANISM: Homo sapiens

<400> SEQUENCE: 89

Gly Ile Thr Glu Glu Ile Met Glu Ile Ala Leu Gly Gln
1               5                   10

<210> SEQ ID NO 90
<211> LENGTH: 13
<212> TYPE: PRT
<213> ORGANISM: Homo sapiens

<400> SEQUENCE: 90

Val Thr Asp Ile Leu Lys Glu Gly Gln Glu Val Glu Val
1               5                   10

<210> SEQ ID NO 91
<211> LENGTH: 11
<212> TYPE: PRT
<213> ORGANISM: Homo sapiens

<400> SEQUENCE: 91

Glu Thr Gln Ala Asp Pro Met Ala Phe Val Lys
1               5                   10

<210> SEQ ID NO 92
<211> LENGTH: 10
<212> TYPE: PRT
<213> ORGANISM: Homo sapiens

<400> SEQUENCE: 92

Lys Thr Ala Val Ala Pro Ile Glu Arg Val
1               5                   10

<210> SEQ ID NO 93
<211> LENGTH: 16
<212> TYPE: PRT
<213> ORGANISM: Homo sapiens

<400> SEQUENCE: 93

Ser Gly Gln Val Pro Arg Tyr Thr Gly Ile Val Asn Cys Phe Val Arg
1               5                   10                  15

<210> SEQ ID NO 94
<211> LENGTH: 11
<212> TYPE: PRT
<213> ORGANISM: Homo sapiens

<400> SEQUENCE: 94

Lys Asp Thr Ile Lys Gly Leu Phe Pro Lys Tyr
1               5                   10

<210> SEQ ID NO 95
<211> LENGTH: 21
<212> TYPE: PRT
<213> ORGANISM: Homo sapiens

<400> SEQUENCE: 95

Gly Gly Pro Met Ala Leu Tyr Gln Gly Phe Gly Val Ser Val Gln Gly
1               5                   10                  15
```

```
Ile Ile Val Tyr Arg
            20

<210> SEQ ID NO 96
<211> LENGTH: 10
<212> TYPE: PRT
<213> ORGANISM: Homo sapiens

<400> SEQUENCE: 96

Lys Gly Val Leu Phe Lys Asp Glu Arg Thr
1               5                   10

<210> SEQ ID NO 97
<211> LENGTH: 12
<212> TYPE: PRT
<213> ORGANISM: Homo sapiens

<400> SEQUENCE: 97

Val Ala Gln Gln Glu Gly Met Lys Ala Phe Phe Lys
1               5                   10

<210> SEQ ID NO 98
<211> LENGTH: 12
<212> TYPE: PRT
<213> ORGANISM: Homo sapiens

<400> SEQUENCE: 98

Phe Ile Asn Pro Asn Ala Val Ser Ser Ala Ser Glu
1               5                   10

<210> SEQ ID NO 99
<211> LENGTH: 18
<212> TYPE: PRT
<213> ORGANISM: Homo sapiens

<400> SEQUENCE: 99

Ser Val Gln Ala Leu Ile Ala Asp Phe Gln Gly Thr Pro Thr Phe Thr
1               5                   10                  15

Tyr Lys

<210> SEQ ID NO 100
<211> LENGTH: 12
<212> TYPE: PRT
<213> ORGANISM: Homo sapiens

<400> SEQUENCE: 100

Tyr Glu Thr Thr Gly Leu Ser Glu Ser Arg Glu Lys
1               5                   10

<210> SEQ ID NO 101
<211> LENGTH: 11
<212> TYPE: PRT
<213> ORGANISM: Homo sapiens

<400> SEQUENCE: 101

Ala Asn Ile Lys Asp Leu Ser His Ile Leu Lys
1               5                   10

<210> SEQ ID NO 102
<211> LENGTH: 11
<212> TYPE: PRT
<213> ORGANISM: Homo sapiens

<400> SEQUENCE: 102

Glu Arg Met Glu Pro Thr Tyr Gln Leu Ser Arg
```

```
                   1               5                  10
```

<210> SEQ ID NO 103
<211> LENGTH: 11
<212> TYPE: PRT
<213> ORGANISM: Homo sapiens

<400> SEQUENCE: 103

```
Phe Leu Asp Asp Leu Lys Thr Leu Asp Gln Lys
1               5                  10
```

<210> SEQ ID NO 104
<211> LENGTH: 13
<212> TYPE: PRT
<213> ORGANISM: Homo sapiens

<400> SEQUENCE: 104

```
Gly Pro Pro Ser Pro Pro Gly Ile Pro Gly Gln Pro
1               5                  10
```

<210> SEQ ID NO 105
<211> LENGTH: 20
<212> TYPE: PRT
<213> ORGANISM: Homo sapiens

<400> SEQUENCE: 105

```
Cys Val Thr Leu Ser Ala Gln Gly Arg Gly Thr Pro Lys Pro Gly Leu
1               5                  10                 15
Phe Gly Ala Pro
            20
```

<210> SEQ ID NO 106
<211> LENGTH: 16
<212> TYPE: PRT
<213> ORGANISM: Homo sapiens

<400> SEQUENCE: 106

```
Gln Ile Met Ala His Phe Ser Asp Val Ala Glu Ala Tyr Ile Glu Lys
1               5                  10                 15
```

<210> SEQ ID NO 107
<211> LENGTH: 19
<212> TYPE: PRT
<213> ORGANISM: Homo sapiens

<400> SEQUENCE: 107

```
Phe Tyr Ala Trp Met Ile Glu Gln Ala Pro Phe Ser Ser Leu Ala Gln
1               5                  10                 15
Glu Gly Lys
```

<210> SEQ ID NO 108
<211> LENGTH: 20
<212> TYPE: PRT
<213> ORGANISM: Homo sapiens

<400> SEQUENCE: 108

```
Asn Leu Tyr Thr Glu Ile Val Tyr Thr Pro Ile Ser Thr Pro Asp Gly
1               5                  10                 15
Thr Leu Val Lys
            20
```

<210> SEQ ID NO 109
<211> LENGTH: 22
<212> TYPE: PRT

<213> ORGANISM: Homo sapiens

<400> SEQUENCE: 109

Gly Ala Asn Asn Leu Phe Gly Leu Asp Gly Asn Val Gly Thr Thr
1               5                   10                  15
Val Glu Asn Thr Glu Arg
            20

<210> SEQ ID NO 110
<211> LENGTH: 16
<212> TYPE: PRT
<213> ORGANISM: Homo sapiens

<400> SEQUENCE: 110

Lys Phe Gln Phe Gly Gln Ser Thr Val Thr Leu Glu Thr Gly Arg Ile
1               5                   10                  15

<210> SEQ ID NO 111
<211> LENGTH: 10
<212> TYPE: PRT
<213> ORGANISM: Homo sapiens

<400> SEQUENCE: 111

Gly Ala Val Thr Ser Ser Asn Ile Ala Ala
1               5                   10

<210> SEQ ID NO 112
<211> LENGTH: 6
<212> TYPE: PRT
<213> ORGANISM: Homo sapiens

<400> SEQUENCE: 112

Asp Leu Asp Gln Ser Val
1               5

<210> SEQ ID NO 113
<211> LENGTH: 6
<212> TYPE: PRT
<213> ORGANISM: Homo sapiens

<400> SEQUENCE: 113

Glu Trp Trp Arg Leu Asp
1               5

<210> SEQ ID NO 114
<211> LENGTH: 5
<212> TYPE: PRT
<213> ORGANISM: Homo sapiens

<400> SEQUENCE: 114

Lys Asn Ser Leu Asp
1               5

<210> SEQ ID NO 115
<211> LENGTH: 8
<212> TYPE: PRT
<213> ORGANISM: Homo sapiens

<400> SEQUENCE: 115

Met His Ile Glu Ser Leu Asp Ser
1               5

<210> SEQ ID NO 116
<211> LENGTH: 5
<212> TYPE: PRT

```
<213> ORGANISM: Homo sapiens

<400> SEQUENCE: 116

Leu Glu Gln Val Glu
1               5

<210> SEQ ID NO 117
<211> LENGTH: 9
<212> TYPE: PRT
<213> ORGANISM: Homo sapiens

<400> SEQUENCE: 117

Leu His Leu Glu Ser Leu Lys Asp Ser
1               5

<210> SEQ ID NO 118
<211> LENGTH: 8
<212> TYPE: PRT
<213> ORGANISM: Homo sapiens

<400> SEQUENCE: 118

Glu Ala Val Ser Leu Lys Pro Thr
1               5

<210> SEQ ID NO 119
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 119
gcauuuugca caccaaggu                                                    19

<210> SEQ ID NO 120
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 120
gcaauaagga gaacuagaa                                                    19

<210> SEQ ID NO 121
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 121
guugucaaau ucacaaaga                                                    19

<210> SEQ ID NO 122
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 122
guuguagccu ggaccuuga                                                    19

<210> SEQ ID NO 123
<211> LENGTH: 412
```

<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (28)..(30)
<223> OTHER INFORMATION: n is a, c, g or t

<400> SEQUENCE: 123

```
taaatataag caatcccaac actttggnnn gccgaggcgg gcggatcacg aggtcaggag      60
atggagacca tcctggctaa cacagtgaaa ccctgtctct actgaaaata caaaaaagta     120
gccgggcgtg gcggcaggcg cctgtagccc cagctactca ggaggctgag gcaggagaat     180
ggcatgaacc caggaggcag agcttgcagt gagccgagat tgtgccactg cactccagcc     240
tgggcaacag agcgagactc catctcaaaa aaaaaaaaaa aatcaccccca aagcaataag    300
gagaactaga acaggacata cactccaaca ctggtgaaac taggaaaaca tatgtaaccc     360
caaaccacaa tatatacaca caaaactata cgagatgttg ggattgctta at             412
```

<210> SEQ ID NO 124
<211> LENGTH: 456
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 124

```
nnnnnngntc cggccgccat ggcggccgcg ggattcgatt aaatataagc aatcccaaca      60
ctttgggagg ccgaggcggg cggatcacga ggtcaggaga tggagaccat cctggctaac     120
acagtgaaac cctgtctcta cggaaaatac aaaaaagtag ccgggcgtgg cggcaggcgc     180
ctgtagtccc agctactcag gaggctgagg caggagaatg gcatgaaccc aggaggcaga     240
gcttgcagtg agccgagatt gtgccactgc actccagcct gggcaacaga gcgagactcc     300
atctcaaaaa aaaaaaaaaa tcaccccaaa gcaataagga gaactagaac aggacataca     360
ctccaacact ggtgaaacta ggaaaacata tgtaacccca aaccacaata tatacacaca     420
aaactatacg agatgttggg attgcttata tttaat                               456
```

<210> SEQ ID NO 125
<211> LENGTH: 587
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(9)
<223> OTHER INFORMATION: n is a, c, g or t
<220> FEATURE:
<221> NAME/KEY: misc_feature
<222> LOCATION: (11)..(15)
<223> OTHER INFORMATION: n is a, c, g or t
<220> FEATURE:
<221> NAME/KEY: misc_feature
<222> LOCATION: (17)..(18)
<223> OTHER INFORMATION: n is a, c, g or t
<220> FEATURE:
<221> NAME/KEY: misc_feature

```
<222> LOCATION: (21)..(21)
<223> OTHER INFORMATION: n is a, c, g or t

<400> SEQUENCE: 125
nnnnnnnnng nnnnngnncc ntggcggccg cgggattcga ttaaatataa gcaatcccaa      60
cactttgggg gggtgaggcg dacagatcac ttgaggtcag gggtttgaga ccagcatggc     120
caacgtggtg aaaactcaac tactcaaaat agaaaaatta gctggacatg gtggcacaca     180
cctgtgaagc cagctactca ggaggctgaa gcatgagaat tgcttgaacc ctggagatgg     240
aggttacagt gagcccacgt cgcgtccctg cacgcaagcc taggcaagaa agcaagaccc     300
tgtctcaaaa aaagaaaaga gatgctgata catgctacaa catagatgaa ccttgaggac     360
attattctaa gtgaaatgag cttgtcacaa aagaacaaat attgcatgat tccagttata     420
tgaggtgccc atagttgtca aattcacaaa gacaaaaagt ggcatggtcg ttaccaaggg     480
ctgggagaaa agaggaatgg tgagttagtg tttaattggt acagagtttc agttttgcaa     540
gatgaaaaga gttctggaga tgaatgttgg gattgcttat atttaat                   587

<210> SEQ ID NO 126
<211> LENGTH: 514
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(80)
<223> OTHER INFORMATION: n is a, c, g, or t

<400> SEQUENCE: 126
nnnnnnnngn ncnnnnanng nannncnact cactnnaggg cgaattgggc ccgacgtcgc      60
atgctcccgg ccgnnannnn ggccgcggga attcgattaa atataagcaa tcccaacact     120
ttgggaggcc gaggcgggcg gatcacgagg tcaggagatg gagaccatcc tggctaacac     180
```

```
agtgaaaccc tgtctctact gaaaatacaa aaaagtagcc gggcgtggcg gcaggcgcct    240
gtagtcccag ctactcagga ggctgaggca ggagaatggc atgaacccag gaggcagagc    300
ttgcagtgag ccgagattgt gccactgcac tccagcctgg gcaacagagc gagactccat    360
ctcaaaaaaa aaaaaaaatc accccaaagc aataaggaga actagaacag gacatacact    420
ccaacactgg tgaaactagg aaaacatatg taaccccaaa ccacaatata tacacacaaa    480
actatacgag atgttgggat tgcttatatt taat                                514

<210> SEQ ID NO 127
<211> LENGTH: 688
<212> TYPE: DNA
<213> ORGANISM: Artificial Sequence
<220> FEATURE:
<223> OTHER INFORMATION: synthetic polynucleotide

<400> SEQUENCE: 127
tcctatgctt gactattagc tcctttctt tacctattat tattatttat ttttcagatg      60
gagtctcaca ctgtcgccag gctggagtac agtggcgcca tctcggctca ctgaaccctc    120
cacctaccgg gttcaagtga ttctactgcc gcagtctcca gagtagctgg gactacaggc    180
atgcactacc acacccagct aattttttgt attttttagtt gagatggggt ttcaccatga    240
tggccaggat ggtctcgatc tcttgacctc atgatctgcc tgcctcagcc tcccaaagtg    300
ctgggattac gggcatgagc cactgtgcta ggcctaccta ttttaaaaat aacaagaatt    360
catccaatgg aacgctgaaa tgcctgtgga ggatacaaga ttaatcagca ggattatatt    420
tgcctatgac tccattaatt caattccaga ccctacttat gggtctaatg tcctttatta    480
ggcaatgtag gagattccta tactcctaat aaagtaatct ttttccattt aaatatcttt    540 gcttttatc aggcagtatg tatttccaca agttaattc aatgaaatac acctaaagct    600
gagagtctta tctcgttaat gaatgaaaaa tagaaatcaa ttattctgag atgagattct    660
tcctataatt tttattagtt gttgtgaa                                       688

<210> SEQ ID NO 128
<211> LENGTH: 19
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 128
tcctatgctt gactattag                                                  19

<210> SEQ ID NO 129
<211> LENGTH: 23
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 129
cctgacatcc ctacatcacc gca                                             23

<210> SEQ ID NO 130
<211> LENGTH: 19
<212> TYPE: DNA
<213> ORGANISM: Artificial Sequence
<220> FEATURE:
<223> OTHER INFORMATION: synthetic polynucleotide; for oligonucleotide
```

```
                                    PCR

<400> SEQUENCE: 130
atgtatatta tatatctaa                                                  19

<210> SEQ ID NO 131
<211> LENGTH: 19
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 131
ttagatatat aatatacat                                                  19

<210> SEQ ID NO 132
<211> LENGTH: 20
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 132
aaatataagc aatcccaaca                                                 20

<210> SEQ ID NO 133
<211> LENGTH: 20
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 133
tgttgggatt gcttatattt                                                 20

<210> SEQ ID NO 134
<211> LENGTH: 18
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 134
ctttattatt ttgtaaat                                                   18

<210> SEQ ID NO 135
<211> LENGTH: 18
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 135
atttacaaaa taataaag                                                   18

<210> SEQ ID NO 136
<211> LENGTH: 19
<212> TYPE: DNA
<213> ORGANISM: Artificial Sequence
<220> FEATURE:
<223> OTHER INFORMATION: synthetic polynucleotide; for oligonucleotide
      PCR
```

-continued

<400> SEQUENCE: 136
tcctatgctt gactattgc                                               19

<210> SEQ ID NO 137
<211> LENGTH: 23
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 137
cctgacatcc ctacatcacc cat                                          23

<210> SEQ ID NO 138
<211> LENGTH: 22
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 138
atgttgggat tgcttatatt ta                                           22

<210> SEQ ID NO 139
<211> LENGTH: 19
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 139
tatacgagat gttggattg                                               19

<210> SEQ ID NO 140
<211> LENGTH: 19
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 140
tatacgagat gttggattg                                               19

<210> SEQ ID NO 141
<211> LENGTH: 19
<212> TYPE: DNA
<213> ORGANISM: Artificial Sequence
<220> FEATURE:
<223> OTHER INFORMATION: synthetic polynucleotide; for oligonucleotide
      PCR

<400> SEQUENCE: 141
cattttgcac accaaggtt                                               19

<210> SEQ ID NO 142
<211> LENGTH: 735
<212> TYPE: DNA
<213> ORGANISM: Homo sapiens

<400> SEQUENCE: 142
gagtctgccc ttgcgagctc agagtgtgcc cgtgcgccgc cgccgtcgta cctgccgccg      60
ccgccaccgc caccatgccc aacttcgccg gcacctggaa gatgcgcagc agcgagaatt     120

```
tcgacgagct gctgaaggca ctgggtgtga acgccatgct gaggaaagtg gccgtagcgg    180
ctgcgtccaa gccgcacgtg gagatccgcc aggacgggga tcagttctac atcaagacat    240
ccaccaccgt gcgcaccact gagatcaact tcaaggtcgg agaaggcttt gaggaggaga    300
ccgtggacgg acgcaagtgc aggagtttag ccacttggga gaatgagaac aagatccact    360
gcacccaaac tcttcttgaa ggggacggcc caaaaccta ctggaccgt gagctggcca    420 acgatgaact tatcctgacg tttggcgccg atgacgtggt ctgcaccaga atttatgtcc    480
gggaatgaag gcagctggct tgctcctact ttcaggaagg gatgcaggtc cccgaggaat    540
atgtcatagt tctgagctgc cagtggaccg cccttttccc ctaccaatat taggtgatcc    600
cgttttcccc atgacaatgt tgtagtgtcc cccaccccca cccccctggc cttggtgcct    660
cttgtatccc tagtgctgca tagcccggca tttgcacggt ttcgaagtca ttaaactggt    720
tagacgtgtc tcaaa                                                     735

<210> SEQ ID NO 143
<211> LENGTH: 924
<212> TYPE: DNA
<213> ORGANISM: Homo sapiens

<400> SEQUENCE: 143
cctgacgacc cggcgacggc gacgtctctt ttgactaaaa gacagtgtcc agtgctccag     60
cctaggagtc tacggggacc gcctcccgcg ccgccaccat gcccaacttc tctggcaact    120
ggaaaatcat ccgatcggaa aacttcgagg aattgctcaa agtgctgggg gtgaatgtga    180
tgctgaggaa gattgctgtg gctgcagcgt ccaagccagc agtggagatc aaacaggagg    240
gagacacttt ctacatcaaa acctccacca ccgtgcgcac cacagagatt aacttcaagg    300
ttggggagga gtttgaggag cagactgtgg atgggaggcc ctgtaagagc ctggtgaaat    360
gggagagtga gaataaaatg gtctgtgagc agaagctcct gaagggagag ggccccaaga    420
cctcgtggac cagagaactg accaacgatg gggaactgat cctgaccatg acggcggatg    480
acgttgtgtg caccagggtc tacgtccgag agtgagtggc cacaggtaga accgcggccg    540
aagcccacca ctggccatgc tcaccgccct gcttcactgc cccctccgtc ccaccccctc    600
cttctaggat agcgctcccc ttaccccagt cacttctggg ggtcactggg atgcctcttg    660
cagggtcttg cttctttga cctcttctct cctcccctac accaacaaag aggaatggct    720
gcaagagccc agatcaccca ttccggggttc actccccgcc tccccaagtc agcagtccta    780
gccccaaacc agcccagagc agggtctctc taaaggggac ttgagggcct gagcaggaaa    840
gactggccct ctagcttcta ccctttgtcc ctgtagccta tacagtttag aatatttatt    900 tgttaattttt attaaaatgc ttta                                           924

<210> SEQ ID NO 144
<211> LENGTH: 1200
<212> TYPE: DNA
<213> ORGANISM: Homo sapiens

<400> SEQUENCE: 144
attcctgccg ctgccgccgc cgccgccgag gtcccgcacc agccatggcg cagatcctcc     60
ctgttcgctt tcaggagcac ttccagctcc aaaaccttgg aattaatcca gctaacattg    120
gattcagcac actgaccatg gaatctgaca agttcatatg tatccgagag aaagttggtg    180
agcaggcaca ggtcacgatc attgacatga gtgacccaat ggctccgatc cgacggccta    240
tctctgcaga gagtgccatc atgaatccag cctctaaggt gatagctctg aaagctggga    300
```

```
agacacttca gatctttaat attgagatga agagtaaaat gaaggctcat actatggcag      360
aagaagtgat tttctggaaa tgggtttctg tgaacactgt tgccttggtg accgagaccg      420
cggtctacca ctggagcatg gaaggtgact cccagcccat gaagatgttt gatagacata      480
ccagtctggt gggctgccag gtgattcact accggactga tgagtaccag aagtggctgc      540
tgctcgtagg catctcggct cagcaaaacc gtgtggttgg agcaatgcag ctctactctg      600
tggataggaa ggtttcacaa cccatagaag gccatgctgc ggcttttgca gagttcaaga      660 tggagggga tgccaagcct gccacccttt tctgctttgc tgtacgtaat cccacaggag       720
gcaagttgca catcattgaa gttggacagc ctgcagcggg aaaccaacct tttgtaaaga      780
aagcagtaga tgtgtttttt cctccagagg cacagaatga ttttccagtg gctatgcaga      840
ttggagctaa acatggtgtt atttacttga tcacaaagta tggctatctt catctgtacg      900
acctagagtc tggcgtgtgc atctgcatga accgtattag tgctgacaca atatttgtca      960
ctgctccaca caaaccaacc tctggaatta ttggtgtcaa caaaaaagga caggtactgt     1020
cagtttgtgt tgaggaagat aacattgtga attatgcaac caacgtgctt cagaatccag     1080
accttggtct gcgtttggcc gttcgtagta acctggctgg ggcagagaag ttgtttgtga     1140
gaaaattcaa taccctcttt gcacagggca gctatgctga agccgccaaa gttgcagcgt     1200
```

<210> SEQ ID NO 145
<211> LENGTH: 790
<212> TYPE: DNA
<213> ORGANISM: Homo sapiens

<400> SEQUENCE: 145

```
cgcggggagc cggcgtcggc ggggacgggc ttggcgcgga ccgcacttcc tctccgccac       60
cgggcccggc tccccgcggc tcgggtgaca gcgtcgcggc cgccggacgc agcgcggggc      120
aggcgcgggg agagccgagc gcagcggagg ctccggcgga ggcgcgggga aaatggctga      180
tgactttggc ttcttctcgt cgtcggagag cggtgccccg gaggcggcgg aggaggaccc      240
ggcggccgcc ttcctggccc agcaggagag cgagattgca ggcatagaga acgacgaggg      300
cttcggggca cctgccggca gccatgcggc ccccgcgcag ccgggcccca cgagtggggc      360
tggttctgag gacatgggga ccacagtcaa tggagatgtg tttcaggagg ccaacggtcc      420
tgctgatggc tacgcagcca ttgcccaggc tgacaggctg acccaggagc ctgagagcat      480
ccgcaagtgg cgagaggagc agaggaaacg gctgcaagag ctggatgctg catctaaggt      540
cacggaacag gaatggcggg agaaggccaa gaaggacctg gaggagtgga accagcgcca      600
gagtgaacaa gtagaagaa acaagatcaa caaccggatc gctgacaaag cattctacca      660
gcagccagat gctgatatca tcggctacgt ggcatccgag gaggctttcg tgaaggaatc      720
caaggaggag accccaggca cagagtggga aaggtggcc cagctatgtg acttcaaccc      780
caagagcagc                                                             790
```

<210> SEQ ID NO 146
<211> LENGTH: 1100
<212> TYPE: DNA
<213> ORGANISM: Homo sapiens

<400> SEQUENCE: 146

```
gaagttactg cagccgcggt gttgtgctgt ggggaaggga gaaggatttg taaaccccgg       60
agcgaggttc tgcttacccg aggccgctgc tgtgcggaga cccccgggtg aagccaccgt      120
catcatgtct gaccaggagg caaaaccttc aactgaggac ttgggggata agaaggaagg      180
```

| | |
|---|---|
| tgaatatatt aaactcaaag tcattggaca ggatagcagt gagattcact tcaaagtgaa | 240 |
| aatgacaaca catctcaaga aactcaaaga atcatactgt caaagacagg gtgttccaat | 300 |
| gaattcactc aggtttctct ttgagggtca gagaattgct gataataata ctccaaaaga | 360 |
| actgggaatg gaggaagaag atgtgattga agtttatcag gaacaaacgg ggggtcattc | 420 |
| aacagtttag atattctttt tatttttttt cttttccctc aatccttttt tattttttaaa | 480 |
| aatagttctt ttgtaatgtg gtgttcaaaa cggaattgaa aactggcacc ccatctcttt | 540 |
| gaaacatctg gtaatttgaa ttctagtgct cattattcat tattgtttgt tttcattgtg | 600 |
| ctgattttttg gtgatcaagc ctcagtcccc ttcatattac cctctccttt ttaaaaatta | 660 |
| cgtgtgcaca gagaggtcac cttttttcagg acattgcatt ttcaggcttg tggtgataaa | 720 |
| taagatcgac caatgcaagt gttcataatg actttccaat tggccctgat gttctagcat | 780 |
| gtgattactt cactcctgga ctgtgacttt cagtgggaga tggaagtttt tcagagaact | 840 |
| gaactgtgga aaaatgacct ttccttaact tgaagctact tttaaaattt gagggtctgg | 900 |
| accaaaagaa gaggaatatc aggttgaagt caagatgaca gataaggtga gagtaatgac | 960 |
| taactccaaa gatggcttca ctgaagaaaa ggcattttaa gatttttttaa aaatcttgtc | 1020 |
| agaagatccc agaaaagttc taattttcat tagcaattaa taaagctata catgcagaaa | 1080 |
| tgaatacaac agaacactgc | 1100 |

<210> SEQ ID NO 147
<211> LENGTH: 393
<212> TYPE: DNA
<213> ORGANISM: Homo sapiens

<400> SEQUENCE: 147

| | |
|---|---|
| tcgggaaggg aagtttgaag agtgagtccc tgtgagggcc gtgtgcccat gctaccctcc | 60 |
| ccgcctccct ccacagtgat cagctgttga cctctctgcc tgttggttgt gatctgtggg | 120 |
| caccagctca ttcgtgtcac cctgtctgtg agtcatttag atagaatagt cctccttggg | 180 |
| tctcccacca cccctagctt tgtgtgtagt gtagtgattt tctggctgtc actcatactc | 240 |
| actgggcacc agccttgccc tcttagcctc catccatcca gacagccctt cccacctcct | 300 |
| ggtggtgagc cagtctgcat tcccacgcca tcccaaagcc ctttcatctt ccccgtgcat | 360 |
| tgtagatgga aggagcaccc atgccattca ccc | 393 |

<210> SEQ ID NO 148
<211> LENGTH: 2220
<212> TYPE: DNA
<213> ORGANISM: Homo sapiens

<400> SEQUENCE: 148

| | |
|---|---|
| agcctgagcc gatggtaacg agtggtactg tttccgtttc ttttccatct attgcaactt | 60 |
| tctcaagcat tttcagctct gaactttaat tccagactgt attttctgtg agtcctgatc | 120 |
| aagtgataca aatgagctgc aatggtgaca taaactcttg acagagattg gaaaagtagc | 180 |
| tggaacacca tcttttcttt taacttttta tggtgcttct gttggcatag ttggggaaag | 240 |
| cacctcacaa catgagtttta tcatgaagct tcacagacac tttcaaagaa cagtcattct | 300 |
| gcttgccact ttttgtatgg tgagcattat catttctgct tactacctgt acagtggcta | 360 |
| caaacaggaa aatgaactct ctgagacggc ttcagaagtt gactgtggcg acctccaaca | 420 |
| cctaccatat caactaatgg aagtgaaagc aatgaagctt tttgatgcct caaggacaga | 480 |
| ccccacagtc ctagtatttg tagagagcca gtactcatct cttggtcaag acatcattat | 540 |

```
gattctagaa tcaagtagat tccagtatca cattgaaatt gccctggaa agggagatct      600 cccagtgctt atagacaaaa tgaaaggcaa atacattctc attatttatg agaatatttt     660
aaagtatata aatatggatt cctggaatcg aagccttcta gataaatact gtgtagaata    720
tggtgtgggt gtcattggat tccacaaaac tagtgagaag agtgtacaga gctttcagtt    780
aaaaggtttc ccttttttcca tatatgaaa tcttgcagta aaagattgtt gtattaatcc    840
tcattctcca ttgattcgtg tgaccaaatc ttccaagctt gaaaaggtt ctttacctgg     900 aactgactgg acagttttc agattaatca ttcagcctat caaccagtaa tatttgccaa     960
agtaaagacc ccagaaaacc tttctccttc catctctaaa ggtgctttt atgccactat     1020 tatacatgac ctggggcttc atgatggaat tcaaagggtt cttttttggca acaacttgaa   1080 cttttggctg cacaagctca tcttcataga tgccatctcc ttcttatcag ggaagaggct    1140
gacattgtcc ttggacaggt acattcttgt ggatattgat gatatattg tgggaaaaga    1200 gggaacaaga atgaacacca atgatgtaaa ggccctgctt gatactcaga atcttttgcg    1260
tgcacaaatc acaaatttta cattcaacct gggattttca gggaaatttt accatacagg    1320
aactgaagag gaagatgaag gagatgactg tctgttgggg tctgtggatg agttctggtg    1380
gtttcctcac atgtggagcc atatgcagcc ccacctcttc cacaatgagt catctttggt    1440
ggagcagatg attctcaaca aaaatttgc cttagagcac ggcattccaa cggacatggg    1500
ctacgctgtg gcccctcacc attcgggcgt ctaccctgta catgttcagc tttatgaggc    1560
ctggaagaag gtctggaata ttaaaatcac cagcactgaa gaatatccac atctgaagcc    1620
agctagatac cggagggggtt ttatccacaa aaacatcatg gttctcccaa gacaaacctg    1680
tgggcttttc actcacacca ttttctacaa agaaatatcca gggggtccta aagagctgga    1740
taagagtatc caaggaggag aacttttctt cactgtcgtc ctcaaccta tcagcatttt    1800 catgacccat ttgtccaact atgggaatga ccgactggga ttatatacat tgttaatct    1860 ggccaacttt gtgaagagct ggaccaacct gcgacttcag actctgcctc cagtacaact    1920
ggcccacaag tattttgagc tgttcctga tcagaaagac cctctctggc agaatccttg    1980
cgatgacaaa cgccacagag acatttggtc taaagaaaaa acttgtgatc gcttaccaaa    2040
attcttggta ataggacccc agaaaactgg taccactgct ttgtatttgt tcctggttat    2100
gcacccttcc atccttagta actccccag cccaaaaacc tttgaggagg tacagttctt    2160
taatagaaat aactaccaca ggggattga ttggtatatg gatttcttcc cagtcccatc    2220
```

`<210> SEQ ID NO 149`
`<211> LENGTH: 720`
`<212> TYPE: DNA`
`<213> ORGANISM: Homo sapiens`

`<400> SEQUENCE: 149`

```
gatcacctga ggccaggagt ttgagaccag cctggccaac atggcaaaac ccatctctcta    60 ctaaaaatac aaaaattagc ctgcgtggtg acgagtgcct gtaatcccag ctattcggga    120
ggctgaggca ggagaatcaa ttgaacccgg gaggtggagg ttgcagtgag ccaagatcgt    180
gccactgcac cccagcctgg gcaacagagc gagactctgt ctcaaaaaaa gaaaatgaaa    240
aagacatgct taaattttag cttccatttc tcatcttcta aagccatgct tctcaaacat    300
gagtgagcag acccaggaat cttgttaaaa tgcggattcc gattcaaggg gcctgggagg    360
agcctgaggt cctgcctttc aaaccagctc ccagatgggg ctgatgctga caccagtaaa    420
ctccctttgc acacaagcct gtttaggctg ggtcttctcc aatttgcaca cacagtatcc    480
```

```
cagctatgac attcagaaac atcaagcttg ttctttcctg ccccttgatg ctgcttttttg    540 ttctgtgtct tctcttgagc cccttggtgg tgcttttttgt tctgtgcctt ctcttaagcc    600
ctgccctctg cttggaatgc tctctgccac ctcttcactc ctcctccagg aaaccttcct    660
tgactgcctg ctctctgccc tgcgaggact ctcgggagca gactttgagg agcaggctcc    720
```

<210> SEQ ID NO 150
<211> LENGTH: 12
<212> TYPE: PRT
<213> ORGANISM: Homo sapiens

<400> SEQUENCE: 150

Arg Val Tyr Gly Pro Leu Thr Asn Pro Lys Pro Gln
1               5                   10

<210> SEQ ID NO 151
<211> LENGTH: 10
<212> TYPE: PRT
<213> ORGANISM: Homo sapiens

<400> SEQUENCE: 151

Cys Tyr Arg Ser Ile Leu His Thr Lys Val
1               5                   10

<210> SEQ ID NO 152
<211> LENGTH: 18
<212> TYPE: PRT
<213> ORGANISM: Homo sapiens

<400> SEQUENCE: 152

Ser Tyr Met Ser Met Phe Leu Leu Leu Met Ala Ile Ser Cys Val Leu
1               5                   10                  15

Ala Lys

<210> SEQ ID NO 153
<211> LENGTH: 24
<212> TYPE: PRT
<213> ORGANISM: Homo sapiens

<400> SEQUENCE: 153

Lys Phe Phe Val Phe Ala Leu Ile Leu Ala Leu Met Leu Ser Met Cys
1               5                   10                  15

Gly Ala Asp Ser His Ala Lys Arg
            20

<210> SEQ ID NO 154
<211> LENGTH: 22
<212> TYPE: PRT
<213> ORGANISM: Homo sapiens

<400> SEQUENCE: 154

Leu Asn Trp Ala Ala Glu Val Leu Asp Val Gln Lys Arg Arg Ile Tyr
1               5                   10                  15

Asp Ile Thr Asn Val Leu
            20

<210> SEQ ID NO 155
<211> LENGTH: 93
<212> TYPE: PRT
<213> ORGANISM: Homo sapiens

<400> SEQUENCE: 155

```
Met Phe Glu Asp Pro Thr Arg Pro Gly Lys Gln Gln Gln Leu Gly Gln
1               5                  10                  15

Glu Leu Lys Glu Leu Met Asn Thr Glu Gln Ala Leu Asp Gln Leu Ile
            20                  25                  30

Gln Ser Cys Ser Leu Ser Phe Lys His Leu Thr Glu Asp Lys Ala Asn
        35                  40                  45

Lys Arg Leu Ala Tyr Val Thr Tyr Gln Asp Ile Arg Ala Val Gly Asn
    50                  55                  60

Phe Lys Glu Gln Thr Val Ile Ala Val Lys Ala Pro Pro Gln Thr Arg
65                  70                  75                  80

Leu Glu Val Pro Asp Arg Thr Glu Asp Asn Leu Gln Ile
                85                  90
```

<210> SEQ ID NO 156
<211> LENGTH: 79
<212> TYPE: PRT
<213> ORGANISM: Homo sapiens

<400> SEQUENCE: 156

```
Ala Pro Pro Pro Ser Leu Val Pro Leu Glu Ala Thr Asp Ser Leu
1               5                  10                  15

Leu Glu Leu Pro His Pro Leu Leu Gln Gln Thr Glu Asp Gln Phe Leu
            20                  25                  30

Ser Pro Thr Leu Ala Cys Ser Ser Pro Leu Ile Ser Phe Ser Pro Ser
        35                  40                  45

Leu Asp Gln Asp Tyr Leu Trp Gly Leu Glu Ala Gly Glu Gly Ile
    50                  55                  60

Ser Asp Leu Phe Asp Ser Tyr Asp Leu Gly Asp Leu Leu Ile Asn
65                  70                  75
```

<210> SEQ ID NO 157
<211> LENGTH: 18
<212> TYPE: PRT
<213> ORGANISM: Homo sapiens

<400> SEQUENCE: 157

```
Asp Asp Tyr Leu Trp Gly Leu Glu Ala Gly Glu Gly Ile Ser Asp Leu
1               5                  10                  15

Phe Asp
```

<210> SEQ ID NO 158
<211> LENGTH: 90
<212> TYPE: PRT
<213> ORGANISM: Homo sapiens

<400> SEQUENCE: 158

```
Gly Lys Cys Ile Arg Val Asp Gly Leu Pro Ser Pro Lys Thr Pro Lys
1               5                  10                  15

Ser Pro Gly Glu Lys Thr Arg Tyr Asp Thr Ser Leu Gly Leu Leu Thr
            20                  25                  30

Lys Lys Phe Ile Tyr Leu Leu Ser Glu Ser Glu Asp Gly Val Leu Asp
        35                  40                  45

Leu Asn Trp Ala Ala Glu Val Leu Asp Val Gln Lys Arg Arg Ile Tyr
    50                  55                  60

Asp Ile Thr Asn Val Leu Glu Gly Ile Gln Leu Ile Arg Lys Lys Ala
65                  70                  75                  80

Lys Asn Asn Ile Gln Trp Val Gly Arg Gly
                85                  90
```

```
<210> SEQ ID NO 159
<211> LENGTH: 66
<212> TYPE: PRT
<213> ORGANISM: Homo sapiens

<400> SEQUENCE: 159

Arg Tyr Asp Thr Ser Leu Gly Leu Leu Thr Lys Lys Phe Ile Tyr Leu
1               5                   10                  15

Leu Ser Glu Ser Glu Asp Gly Val Leu Asp Leu Asn Trp Ala Ala Glu
            20                  25                  30

Val Leu Asp Val Gln Lys Arg Arg Ile Tyr Asp Ile Thr Asn Val Leu
        35                  40                  45

Glu Gly Ile Gln Leu Ile Arg Lys Lys Ala Lys Asn Asn Ile Gln Trp
    50                  55                  60

Val Gly
65

<210> SEQ ID NO 160
<211> LENGTH: 142
<212> TYPE: PRT
<213> ORGANISM: Homo sapiens

<400> SEQUENCE: 160

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met
    130                 135                 140

<210> SEQ ID NO 161
<211> LENGTH: 284
<212> TYPE: PRT
<213> ORGANISM: Homo sapiens

<400> SEQUENCE: 161

Leu Gln Glu Ser Ile Gly Lys Gly Arg Phe Gly Glu Val Trp Arg Gly
1               5                   10                  15

Lys Trp Arg Gly Glu Glu Val Ala Val Lys Ile Phe Ser Ser Arg Glu
            20                  25                  30

Glu Arg Ser Trp Phe Arg Glu Ala Glu Ile Tyr Gln Thr Val Met Leu
        35                  40                  45

Arg His Glu Asn Ile Leu Gly Phe Ile Ala Ala Asp Asn Lys Asp Asn
    50                  55                  60

Gly Thr Trp Thr Gln Leu Trp Leu Val Ser Asp Tyr His Glu His Gly
65                  70                  75                  80
```

Ser Leu Phe Asp Tyr Leu Asn Arg Tyr Thr Val Thr Glu Gly Met
            85                  90                  95

Ile Lys Leu Ala Leu Ser Thr Ala Ser Gly Leu Ala His Leu His Met
            100                 105                 110

Glu Ile Val Gly Thr Gln Gly Lys Pro Ala Ile Ala His Arg Asp Leu
            115                 120                 125

Lys Ser Lys Asn Ile Leu Val Lys Lys Asn Gly Thr Cys Cys Ile Ala
130                 135                 140

Asp Leu Gly Leu Ala Val Arg His Asp Ser Ala Thr Asp Thr Ile Asp
145                 150                 155                 160

Ile Ala Pro Asn His Arg Val Gly Thr Lys Arg Tyr Met Ala Pro Glu
                165                 170                 175

Val Leu Asp Asp Ser Ile Asn Met Lys His Phe Glu Ser Phe Lys Arg
            180                 185                 190

Ala Asp Ile Tyr Ala Met Gly Leu Val Phe Trp Glu Ile Ala Arg Arg
            195                 200                 205

Cys Ser Ile Gly Gly Ile His Glu Asp Tyr Gln Leu Pro Tyr Tyr Asp
210                 215                 220

Leu Val Pro Ser Asp Pro Ser Val Glu Glu Met Arg Lys Val Val Cys
225                 230                 235                 240

Glu Gln Lys Leu Arg Pro Asn Ile Pro Asn Arg Trp Gln Ser Cys Glu
                245                 250                 255

Ala Leu Arg Val Met Ala Lys Ile Met Arg Glu Cys Trp Tyr Ala Asn
            260                 265                 270

Gly Ala Ala Arg Leu Thr Ala Leu Arg Ile Lys Lys
            275                 280

<210> SEQ ID NO 162
<211> LENGTH: 737
<212> TYPE: PRT
<213> ORGANISM: Homo sapiens

<400> SEQUENCE: 162

Met Val Val Phe Asn Gly Leu Leu Lys Ile Lys Ile Cys Glu Ala Val
1               5                   10                  15

Ser Leu Lys Pro Thr Ala Trp Ser Leu Arg His Ala Val Gly Pro Arg
            20                  25                  30

Pro Gln Thr Phe Leu Leu Asp Pro Tyr Ile Ala Leu Asn Val Asp Asp
            35                  40                  45

Ser Arg Ile Gly Gln Thr Ala Thr Lys Gln Lys Thr Asn Ser Pro Ala
50                  55                  60

Trp His Asp Glu Phe Val Thr Asp Val Cys Asn Gly Arg Lys Ile Glu
65              70                  75                  80

Leu Ala Val Phe His Asp Ala Pro Ile Gly Tyr Asp Asp Phe Val Ala
                85                  90                  95

Asn Cys Thr Ile Gln Phe Glu Glu Leu Leu Gln Asn Gly Ser Arg His
            100                 105                 110

Phe Glu Asp Trp Ile Asp Leu Glu Pro Glu Gly Arg Val Tyr Val Ile
            115                 120                 125

Ile Asp Leu Ser Gly Ser Ser Gly Glu Ala Pro Lys Asp Asn Glu Glu
130                 135                 140

Arg Val Phe Arg Glu Arg Met Arg Pro Arg Lys Arg Gln Gly Ala Val
145                 150                 155                 160

Arg Arg Arg Val His Gln Val Asn Gly His Lys Phe Met Ala Thr Tyr
                165                 170                 175

```
Leu Arg Gln Pro Thr Tyr Cys Ser His Cys Arg Asp Phe Ile Trp Gly
            180                 185                 190

Val Ile Gly Lys Gln Gly Tyr Gln Cys Gln Val Cys Thr Cys Val Val
        195                 200                 205

His Lys Arg Cys His Glu Leu Ile Ile Thr Lys Cys Ala Gly Leu Lys
    210                 215                 220

Lys Gln Glu Thr Pro Asp Gln Val Gly Ser Gln Arg Phe Ser Val Asn
225                 230                 235                 240

Met Pro His Lys Phe Gly Ile His Asn Tyr Lys Val Pro Thr Phe Cys
                245                 250                 255

Asp His Cys Gly Ser Leu Leu Trp Gly Leu Leu Arg Gln Gly Leu Gln
            260                 265                 270

Cys Lys Val Cys Lys Met Asn Val His Arg Arg Cys Glu Thr Asn Val
        275                 280                 285

Ala Pro Asn Cys Gly Val Asp Ala Arg Gly Ile Ala Lys Val Leu Ala
    290                 295                 300

Asp Leu Gly Val Thr Pro Asp Lys Ile Thr Asn Ser Gly Gln Arg Arg
305                 310                 315                 320

Lys Lys Leu Ile Ala Gly Ala Glu Ser Pro Gln Pro Ala Ser Gly Ser
                325                 330                 335

Ser Pro Ser Glu Glu Asp Arg Ser Lys Ser Ala Pro Thr Ser Pro Cys
            340                 345                 350

Asp Gln Glu Ile Lys Glu Leu Glu Asn Asn Ile Arg Lys Ala Leu Ser
        355                 360                 365

Phe Asp Asn Arg Gly Glu Glu His Arg Ala Ala Ser Ser Pro Asp Gly
370                 375                 380

Gln Leu Met Ser Pro Gly Glu Asn Gly Glu Val Arg Gln Gly Gln Ala
385                 390                 395                 400

Lys Arg Leu Gly Leu Asp Glu Phe Asn Phe Ile Lys Val Leu Gly Lys
                405                 410                 415

Gly Ser Phe Gly Lys Val Met Leu Ala Glu Leu Lys Gly Lys Asp Glu
            420                 425                 430

Val Tyr Ala Val Lys Val Leu Lys Lys Asp Val Ile Leu Gln Asp Asp
        435                 440                 445

Asp Val Asp Cys Thr Met Thr Glu Lys Arg Ile Leu Ala Leu Ala Arg
450                 455                 460

Lys His Pro Tyr Leu Thr Gln Leu Tyr Cys Cys Phe Gln Thr Lys Asp
465                 470                 475                 480

Arg Leu Phe Phe Val Met Glu Tyr Val Asn Gly Gly Asp Leu Met Phe
                485                 490                 495

Gln Ile Gln Arg Ser Arg Lys Phe Asp Glu Pro Arg Ser Arg Phe Tyr
            500                 505                 510

Ala Ala Glu Val Thr Ser Ala Leu Met Phe Leu His Gln His Gly Val
        515                 520                 525

Ile Tyr Arg Asp Leu Lys Leu Asp Asn Ile Leu Leu Asp Ala Glu Gly
530                 535                 540

His Cys Lys Leu Ala Asp Phe Gly Met Cys Lys Glu Gly Ile Leu Asn
545                 550                 555                 560

Gly Val Thr Thr Thr Thr Phe Cys Gly Thr Pro Asp Tyr Ile Ala Pro
                565                 570                 575

Glu Ile Leu Gln Glu Leu Glu Tyr Gly Pro Ser Val Asp Trp Trp Ala
            580                 585                 590

Leu Gly Val Leu Met Tyr Glu Met Met Ala Gly Gln Pro Pro Phe Glu
```

```
                    595                 600                 605
Ala Asp Asn Glu Asp Leu Phe Glu Ser Ile Leu His Asp Val
610                 615                 620

Leu Tyr Pro Val Trp Leu Ser Lys Glu Ala Val Ser Ile Leu Lys Ala
625                 630                 635                 640

Phe Met Thr Lys Asn Pro His Lys Arg Leu Gly Cys Val Ala Ser Gln
            645                 650                 655

Asn Gly Glu Asp Ala Ile Lys Gln His Pro Phe Phe Lys Glu Ile Asp
                660                 665                 670

Trp Val Leu Leu Glu Gln Lys Lys Ile Lys Pro Pro Phe Lys Pro Arg
            675                 680                 685

Ile Lys Thr Lys Arg Asp Val Asn Asn Phe Asp Gln Asp Phe Thr Arg
            690                 695                 700

Glu Glu Pro Val Leu Thr Leu Val Asp Glu Ala Ile Val Lys Gln Ile
705                 710                 715                 720

Asn Gln Glu Glu Phe Lys Gly Phe Ser Tyr Phe Gly Glu Asp Leu Met
                725                 730                 735

Pro

<210> SEQ ID NO 163
      <211> LENGTH: 138
<212> TYPE: PRT
<213> ORGANISM: Homo sapiens

<400> SEQUENCE: 163

Met Pro Asn Phe Ser Gly Asn Trp Lys Ile Ile Arg Ser Glu Asn Phe
1               5                   10                  15

Glu Glu Leu Leu Lys Val Leu Gly Val Asn Val Met Leu Arg Lys Ile
            20                  25                  30

Ala Val Ala Ala Ala Ser Lys Pro Ala Val Glu Ile Lys Gln Glu Gly
        35                  40                  45

Asp Thr Phe Tyr Ile Lys Thr Ser Thr Thr Val Arg Thr Thr Glu Ile
    50                  55                  60

Asn Phe Lys Val Gly Glu Glu Phe Glu Glu Gln Thr Val Asp Gly Arg
65                  70                  75                  80

Pro Cys Lys Ser Leu Val Lys Trp Glu Ser Glu Asn Lys Met Val Cys
                85                  90                  95

Glu Gln Lys Leu Leu Lys Gly Glu Gly Pro Lys Thr Ser Trp Thr Arg
            100                 105                 110

Glu Leu Thr Asn Asp Gly Glu Leu Ile Leu Thr Met Thr Ala Asp Asp
        115                 120                 125

Val Val Cys Thr Arg Val Tyr Val Arg Glu
    130                 135

<210> SEQ ID NO 164
<211> LENGTH: 134
<212> TYPE: PRT
<213> ORGANISM: Homo sapiens

<400> SEQUENCE: 164

Met Pro Ala Asp Leu Ser Gly Thr Trp Thr Leu Leu Ser Ser Asp Asn
1               5                   10                  15

Phe Glu Gly Tyr Met Leu Ala Leu Gly Ile Asp Phe Ala Thr Arg Lys
            20                  25                  30

Ile Ala Lys Leu Leu Lys Pro Gln Lys Val Ile Glu Gln Asn Gly Asp
        35                  40                  45
```

Ser Phe Thr Ile His Thr Asn Ser Ser Leu Arg Asn Tyr Phe Val Lys
    50                  55                  60

Phe Lys Val Gly Glu Glu Phe Asp Glu Asp Asn Arg Gly Leu Asp Asn
65                  70                  75                  80

Arg Lys Cys Lys Ser Leu Val Ile Trp Asp Asn Asp Arg Leu Thr Cys
                85                  90                  95

Ile Gln Lys Gly Glu Lys Lys Asn Arg Gly Trp Thr His Trp Ile Glu
            100                 105                 110

Gly Asp Lys Leu His Leu Glu Met Phe Cys Glu Gly Gln Val Cys Lys
        115                 120                 125

Gln Thr Phe Gln Arg Ala
    130

<210> SEQ ID NO 165
<211> LENGTH: 101
<212> TYPE: PRT
<213> ORGANISM: Homo sapiens

<400> SEQUENCE: 165

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Lys
        35                  40                  45

Glu Ser Tyr Cys Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly His Ser Thr Val
            100

<210> SEQ ID NO 166
<211> LENGTH: 229
<212> TYPE: PRT
<213> ORGANISM: Homo sapiens

<400> SEQUENCE: 166

Met Ala Asp Asp Phe Gly Phe Phe Ser Ser Ser Glu Ser Gly Ala Pro
1               5                   10                  15

Glu Ala Ala Glu Glu Asp Pro Ala Ala Ala Phe Leu Ala Gln Gln Glu
            20                  25                  30

Ser Glu Ile Ala Gly Ile Glu Asn Asp Glu Gly Phe Gly Ala Pro Ala
        35                  40                  45

Gly Ser His Ala Ala Pro Ala Gln Pro Gly Pro Thr Ser Gly Ala Gly
    50                  55                  60

Ser Glu Asp Met Gly Thr Thr Val Asn Gly Asp Val Phe Gln Glu Ala
65                  70                  75                  80

Asn Gly Pro Ala Asp Gly Tyr Ala Ala Ile Ala Gln Ala Asp Arg Leu
                85                  90                  95

Thr Gln Glu Pro Glu Ser Ile Arg Lys Trp Arg Glu Glu Gln Arg Lys
            100                 105                 110

Arg Leu Gln Glu Leu Asp Ala Ala Ser Lys Val Thr Glu Gln Glu Trp
        115                 120                 125

Arg Glu Lys Ala Lys Lys Asp Leu Glu Glu Trp Asn Gln Arg Gln Ser

```
                130                 135                 140
Glu Gln Val Glu Lys Asn Lys Ile Asn Asn Arg Ile Ala Asp Lys Ala
145                 150                 155                 160

Phe Tyr Gln Gln Pro Asp Ala Asp Ile Ile Gly Tyr Val Ala Ser Glu
                165                 170                 175

Glu Ala Phe Val Lys Glu Ser Lys Glu Glu Thr Pro Gly Thr Glu Trp
                180                 185                 190

Glu Lys Val Ala Gln Leu Cys Asp Phe Asn Pro Lys Ser Ser Lys Gln
                195                 200                 205

Cys Lys Asp Val Ser Arg Leu Arg Ser Val Leu Met Ser Leu Lys Gln
                210                 215                 220

Thr Pro Leu Ser Arg
225

<210> SEQ ID NO 167
<211> LENGTH: 58
<212> TYPE: PRT
<213> ORGANISM: Homo sapiens

<400> SEQUENCE: 167

Glu Lys Pro Pro Val Asn Lys Gln Glu Asn Ala Gly Thr Leu Asn
1               5                   10                  15

Ile Leu Ser Thr Leu Ser Asn Gly Asn Ser Ser Lys Gln Lys Ile Pro
                20                  25                  30

Ala Asp Gly Val His Arg Ile Arg Val Asp Phe Lys Gln Val Gly Ile
                35                  40                  45

Asp Arg Gly Asp Ile Pro Asp Leu Ser Gln
                50                  55

<210> SEQ ID NO 168
<211> LENGTH: 73
<212> TYPE: PRT
<213> ORGANISM: Homo sapiens

<400> SEQUENCE: 168

Ser Val Lys Ser Leu Ala Gly Gly Leu Val Leu Phe Phe Phe Phe Thr
1               5                   10                  15

Ala Phe Ala Thr Leu Thr Val Ala Ile Leu Leu Ile Met Glu Gly Leu
                20                  25                  30

Ser Ala Phe Leu His Ala Leu Arg Leu His Trp Val Glu Phe Gln Asn
                35                  40                  45

Lys Phe Tyr Ser Gly Thr Gly Phe Lys Phe Leu Pro Phe Ser Phe Glu
                50                  55                  60

His Ile Arg Glu Gly Lys Phe Glu Glu
65                  70

<210> SEQ ID NO 169
<211> LENGTH: 7
<212> TYPE: PRT
<213> ORGANISM: Homo sapiens

<400> SEQUENCE: 169

Arg Arg Met Lys Trp Lys Lys
1               5

<210> SEQ ID NO 170
<211> LENGTH: 10
<212> TYPE: PRT
<213> ORGANISM: Homo sapiens
```

<400> SEQUENCE: 170

Leu Tyr Lys Asp Pro Cys Ala Phe Gln Arg
1               5                   10

<210> SEQ ID NO 171
<211> LENGTH: 446
<212> TYPE: DNA
<213> ORGANISM: Homo sapiens
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (62)..(64)
<223> OTHER INFORMATION: n is a, c, g, or t

<400> SEQUENCE: 171
gnncnngccg ccnnggcggc cgcgggaatt cgattaaata taagcaatcc caacactttg      60
gnnngccgag gcgggcggat cacgaggtca ggagatggag accatcctgg ctaacacagt     120
gaaaccctgt ctctactgaa atacaaaaa agtagccggg cgtggcggca ggcgcctgta     180
gccccagcta ctcaggaggc tgaggcagga gaatggcatg aacccaggag gcagagcttg     240
cagtgagccg agattgtgcc actgcactcc agcctgggca acagagcgag actccatctc     300
aaaaaaaaaa aaaaaatcac cccaaagcaa taaggagaac tagaacagga catacactcc     360
aacactggtg aaactaggaa aacatatgta accccaaacc acaatatata cacacaaaac     420
tatacgagat gttgggattg cttaat                                          446

<210> SEQ ID NO 172
<211> LENGTH: 450
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t

<400> SEQUENCE: 172
gntccggccg ccatggcggc cgcgggattc gattaaatat aagcaatccc aacactttgg      60
gaggccgagg cgggcggatc acgaggtcag gagatggaga ccatcctggc taacacagtg     120
aaaccctgtc tctacggaaa atacaaaaaa gtagccgggc gtggcggcag gcgcctgtag     180
tcccagctac tcaggaggct gaggcaggag aatggcatga acccaggagg cagagcttgc     240
agtgagccga gattgtgcca ctgcactcca gcctgggcaa cagagcgaga ctccatctca     300
aaaaaaaaaa aaaatcaccc caaagcaata aggagaacta gaacaggaca tacactccaa     360
cactggtgaa actaggaaaa catatgtaac cccaaaccac aatatataca cacaaaacta     420
tacgagatgt tgggattgct tatatttaat                                      450

<210> SEQ ID NO 173
<211> LENGTH: 569
<212> TYPE: DNA
<213> ORGANISM: Homo sapiens
<220> FEATURE:
<221> NAME/KEY: misc_feature

```
<222> LOCATION: (3)..(3)
<223> OTHER INFORMATION: n is a, c, g, or t

<400> SEQUENCE: 173
ccntggcggc cgcgggattc gattaaatat aagcaatccc aacactttgg gggggtgagg      60
cggacagatc acttgaggtc aggggtttga gaccagcatg gccaacgtgg tgaaaactca    120
actactcaaa atagaaaaat tagctggaca tggtggcaca cacctgtgaa gccagctact    180
caggaggctg aagcatgaga attgcttgaa ccctggagat ggaggttaca gtgagcccac    240
gtcgcgtccc tgcacgcaag cctaggcaag aaagcaagac cctgtctcaa aaaagaaaa    300
gagatgctga tacatgctac aacatagatg aaccttgagg acattattct aagtgaaatg    360
agcttgtcac aaaagaacaa atattgcatg attccagtta tatgaggtgc ccatagttgt    420
caaattcaca aagacaaaaa gtggcatggt cgttaccaag ggctgggaga aaagaggaat    480
ggtgagttag tgtttaattg gtacagagtt tcagttttgc aagatgaaaa gagttctgga    540
gatgaatgtt gggattgctt atatttaat                                       569

<210> SEQ ID NO 174
<211> LENGTH: 448
<212> TYPE: DNA
<213> ORGANISM: Homo sapiens
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (11)..(14)
<223> OTHER INFORMATION: n is a, c, g, or t

<400> SEQUENCE: 174
ccggccgnna nnnnggccgc gggaattcga ttaaatataa gcaatcccaa cactttggga      60
ggccgaggcg gcggatcac gaggtcagga gatggagacc atcctggcta acacagtgaa    120
accctgtctc tactgaaaat acaaaaaagt agccgggcgt ggcggcaggc gcctgtagtc    180
ccagctactc aggaggctga ggcaggagaa tggcatgaac ccaggaggca gcttgcag     240
tgagccgaga ttgtgccact gcactccagc ctgggcaaca gagcgagact ccatctcaaa    300
aaaaaaaaaa aatcacccca aagcaataag gagaactaga acaggacata cactccaaca    360
ctggtgaaac taggaaaaca tatgtaaccc caaaccacaa tatatacaca caaaactata    420
cgagatgttg ggattgctta tatttaat                                        448

<210> SEQ ID NO 175
<211> LENGTH: 447
<212> TYPE: DNA
<213> ORGANISM: Homo sapiens

<400> SEQUENCE: 175
ccggccgcca tggcggccgc gggattcgat taaatataag caatcccaac actttgggag      60
gccgaggcgg cggatcacg aggtcaggag atggagacca tcctggctaa cacagtgaaa    120
ccctgtctct actgaaaata caaaaaagta gccgggcgtg gcggcaggcg cctgtagtcc    180
cagctactca ggaggctgag gcaggagaat ggcatgaacc caggaggcag agcttgcagt    240
gagccgagat tgtgccactg cactccagcc tgggcaacag agcgagactc catctcaaaa    300
aaaaaaaaaa atcaccccaa agcaataagg agaactagaa caggacatac actccaacac    360
tggtgaaact aggaaaacat atgtaacccc aaaccacaat atatacacac aaaactatac    420
gagatgttgg gattgcttat atttaat                                         447
```

<210> SEQ ID NO 176
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 176
uugguaacga ccaugccac                                                19

<210> SEQ ID NO 177
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 177
uucacuuaga auaaugucc                                                19

<210> SEQ ID NO 178
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 178
ucuuugugaa uuugacaac                                                19

<210> SEQ ID NO 179
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 179
ucaaggucca ggcuacaac                                                19

<210> SEQ ID NO 180
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 180
guggcauggu cguuaccaat t                                             21

<210> SEQ ID NO 181
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 181
uugguaacga ccaugccact t                                             21

<210> SEQ ID NO 182
<211> LENGTH: 21
<212> TYPE: DNA
<213> ORGANISM: Artificial Sequence
<220> FEATURE:
<223> OTHER INFORMATION: synthetic oligonucleotide

```
<400> SEQUENCE: 182
ggacauuauu cuaagugaat t                                              21

<210> SEQ ID NO 183
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 183
uucacuuaga auaaugucct t                                              21

<210> SEQ ID NO 184
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 184
guugucaaau ucacaaagat t                                              21

<210> SEQ ID NO 185
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 185
ucuuugugaa uuugacaact t                                              21

<210> SEQ ID NO 186
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 186
guuguagccu ggaccuugat t                                              21

<210> SEQ ID NO 187
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 187
ucaaggucca ggcuacaact t                                              21

<210> SEQ ID NO 188
<211> LENGTH: 22
<212> TYPE: PRT
<213> ORGANISM: Artificial Sequence
<220> FEATURE:
<223> OTHER INFORMATION: synthetic peptide; regio leucine zipper

<400> SEQUENCE: 188
```

```
Leu Asn Trp Ala Ala Glu Val Leu Asp Val Gln Lys Thr Thr Ile Tyr
1               5                   10                  15
Asp Ile Thr Asn Val Leu
            20
```

The invention claimed is:

1. A detectable isolated complex corresponding to human Liv21 used in detecting cancer comprising:
   an isolated nucleic acid comprising the nucleotide sequence in any of SEQ ID NO: 123, SEQ ID NO: 124 and SEQ ID NO: 127 or a full complement thereof,
   an isolated nucleic acid comprising the nucleotide sequence of SEQ ID NO:120 or SEQ ID NO: 121 or a full complement thereof, and
   a protein fraction comprising at least the sequence SEQ ID NO: 1 or a sequence being at least 70% identical with said SEQ ID NO: 1.

2. The complex of human Liv21 according to claim 1, further comprising:
   an isolated nucleic acid selected from any one of:
   (a) nucleotide sequences SEQ ID NO: 119, SEQ ID NO: 120, SEQ ID NO: 122, SEQ ID NO: 125 or SEQ ID NO: 126 or a full complement thereof; or
   (b) a sequence being at least 70% identical with said sequences SEQ ID NO: 119; SEQ ID NO:120 or a full complement thereof, or
   (c) any one of SEQ ID NO: 176; SEQ ID NO: 177; SEQ ID NO: 178; or SEQ ID NO 179, or a full complement thereof;
   (d) the nucleotide sequence or a full complement thereof as listed in SEQ ID NO: 174.

3. The complex of human Liv21 according to claim 1, further comprising at least one of:
   an isolated nucleic acid having any one of nucleotide sequences SEQ ID NO: 123, SEQ ID NO: 124 and SEQ ID NO: 127 to SEQ ID NO: 149, and
   a polypeptide having any one of amino acid sequences SEQ ID NO: 1 to SEQ ID NO: 118 and SEQ ID NO: 150 to SEQ ID NO: 170, or a sequence being at least 70% identical with those sequences SEQ ID NO: 1 to SEQ ID NO: 118.

4. The complex of human Liv21 according to claim 1, wherein the protein fraction further includes any of the following proteins: E2F1, E2F4, E2F2, Histone H3, Histone H4, p130, p300, p107, Liv21 F, HDAC-1, PML, SUMO, -pKCepsilon and cellular retinoic acid protein 2 (RABP2) and retinoid binding protein 7 (CRABP4).

5. The complex of human Liv21 according to claim 1, wherein said complex interacts with at least one of its partners, said at least one of its partners are selected from the group consisting of:
   (a) any one of the following proteins: RBP2, TNFalpha, TGFBeta, CRB2, cycE/cdk2, Cdk1, CREB1, p300, p107, NFkB, cdc2A, mdm2, p21, p53, p65, pKCepsilon, or
   (b) an antibody to any of the following proteins: RBP2, E2F4, E2F1, SUMO, HDAC-1, CRB2, Int2, cmd2, cycE/cdk2, cdk1, CREB1 and p300, Rb, p 107, p130 of families of NFkB protein pockets, cdc2A, mdm2, p21, p53, p65, Ki67, CAF1, the A and cyclin D1.

6. The complex of human Liv21 according to claim 5, wherein said complex comprises an extract of proteins and peptides obtained by hanging a polyclonal antibody to the protein Liv21 and said complex has acrylamide gel electrophoretic profile including at least the following three bands: the band of 50 kD, the band of 51 kD and 52 kD band.

7. The complex of human Liv21 according to claim 6, wherein after digestion with trypsin, a pattern of MALDI mass spectrometry of the 51 kD band of said complex includes the following:

| m/z | SN | Res. | intens. |
|---|---|---|---|
| 525.380 | 75.6 | 1903 | 3408.00 |
| 545.322 | 133.8 | 1436 | 6029.00 |
| 550.930 | 142.9 | 1612 | 6438.00 |
| 568.641 | 790.8 | 2123 | 35626.00 |
| 580.777 | 26.4 | 2516 | 1190.00 |
| 587.667 | 33.3 | 2795 | 1501.00 |
| 631.470 | 66.4 | 6569 | 2991.00 |
| 659.447 | 30.9 | 6811 | 1394.00 |
| 662.431 | 67.2 | 9193 | 3027.00 |
| 667.159 | 41.0 | 10087 | 1846.00 |
| 711.153 | 34.5 | 10289 | 1553.00 |
| 713.175 | 42.7 | 11689 | 1922.00 |
| 739.151 | 20.4 | 12971 | 918.00 |
| 757.165 | 13.8 | 13762 | 707.82 |
| 790.491 | 14.4 | 12895 | 649.00 |
| 842.510 | 19.8 | 11687 | 767.71 |
| 870.537 | 8.6 | 11748 | 397.00 |
| 881.259 | 23.3 | 13598 | 829.82 |
| 921.541 | 17.0 | 12241 | 600.49 |
| 1330.770 | 6.3 | 15012 | 284.00 |
| 1341.706 | 3.3 | 7921 | 149.00 |
| 1373.739 | 21.3 | 15547 | 533.87 |
| 1439.840 | 20.1 | 14012 | 522.60 |
| 1451.764 | 15.2 | 13759 | 401.95 |
| 1467.871 | 4.5 | 15096 | 201.00 |
| 1479.823 | 10.1 | 13230 | 256.69 |
| 1486.853 | 7.0 | 21505 | 316.00 |
| 1534.956 | 17.1 | 14704 | 481.02 |
| 1537.826 | 23.5 | 14898 | 675.26 |
| 1567.775 | 37.8 | 15022 | 1065.43 |
| 1570.816 | 14.6 | 15144 | 408.22 |
| 1593.926 | 55.5 | 15098 | 4349.61 |
| 1607.944 | 3.5 | 10703 | 157.00 |
| 1639.938 | 9.4 | 11759 | 238.84 |
| 1684.943 | 21.2 | 6015 | 538.84 |
| 1694.843 | 15.6 | 8084 | 407.76 |
| 1698.906 | 16.6 | 15134 | 431.33 |
| 1721.877 | 4.6 | 17947 | 207.00 |
| 1748.844 | 4.9 | 16483 | 221.00 |
| 1783.031 | 5.0 | 12143 | 223.00 |
| 1794.832 | 17.1 | 15898 | 446.26 |
| 1836.904 | 3.6 | 15701 | 162.00 |
| 1855.950 | 4.8 | 12370 | 214.00 |
| 1873.917 | 15.9 | 17904 | 420.12 |
| 1876.979 | 15.9 | 16250 | 407.25 |
| 1880.935 | 20.1 | 11590 | 515.15 |
| 1927.967 | 6.2 | 11723 | 281.00 |
| 1928.974 | 6.2 | 14954 | 152.02 |
| 1942.020 | 4.7 | 19798 | 211.00 |
| 1944.019 | 20.0 | 15714 | 478.21 |
| 2021.003 | 137.1 | 14814 | 3500.62 |
| 2037.013 | 8.2 | 10928 | 212.04 |
| 2045.020 | 7.3 | 15747 | 330.00 |
| 2059.030 | 4.2 | 14227 | 191.00 |
| 2125.002 | 5.9 | 14783 | 264.00 |
| 2211.105 | 151.9 | 13211 | 3373.88 |
| 2225.106 | 17.2 | 14637 | 773.00 |

-continued

| m/z | SN | Res. | intens. |
|---|---|---|---|
| 2283.181 | 48.1 | 12236 | 2167.00 |
| 2311.205 | 10.0 | 15157 | 207.42 |
| 2383.261 | 73.2 | 10466 | 1204.30 |
| 2461.196 | 11.1 | 11453 | 196.62 |
| 2477.117 | 1.9 | 15432 | 85.00 |
| 2511.375 | 9.1 | 9656 | 154.80 |
| 2539.329 | 11.0 | 9640 | 180.05 |
| 2549.262 | 3.4 | 13928 | 155.00 |
| 2587.249 | 3.4 | 11702 | 153.00 |
| 2591.295 | 25.7 | 10330 | 388.23 |
| 2660.220 | 8.7 | 10510 | 132.78 |
| 2750.500 | 42.2 | 10212 | 533.12 |
| 2765.494 | 9.3 | 8850 | 133.86 |
| 2780.508 | 8.7 | 10597 | 391.00 |
| 2823.368 | 40.4 | 9128 | 513.24 |
| 2837.393 | 13.1 | 6755 | 161.25 |
| 3265.843 | 9.2 | 6905 | 58.89 |
| 3324.905 | 1.5 | 31230 | 68.00 |
| 3338.673 | 2.1 | 6212 | 94.00 |

8. The complex of human Liv21 according to claim 1, wherein said complex interacts with at least one of its partners, said at least one of its partners are selected from the group consisting of;

an antibody to any of the following proteins: pKCepsilon, RBP2, E2F4, E2F1, E2F2, TGFBeta, LIV21F, SUMO, HDAC-1, CRB2, Int2, cmd2, cycE/cdk2, cdk1CREB1and p300, Rb, p107, p130 of families of NFkB protein pockets, cdc2A, mdm2, p21, p53, p65, Ki67, CAF1, the A and cyclin D1.

9. The complex of human Liv21 according to claim 1, further comprising an isolated nucleic acid selected from any one of nucleotide sequences SEQ ID NO: 180, SEQ ID NO: 181, SEQ ID NO: 182, SEQ ID NO: 183, SEQ ID NO: 184, SEQ ID NO: 185, SEQ ID NO: 186, or SEQ ID NO: 187, or a full complement thereof.

* * * * *